(12) United States Patent
Nishimura et al.

(10) Patent No.: US 9,954,178 B2
(45) Date of Patent: Apr. 24, 2018

(54) AROMATIC AMINE DERIVATIVE AND ORGANIC ELECTROLUMINESCENT ELEMENT

(71) Applicant: Idemitsu Kosan Co., Ltd., Chiyoda-ku, Tokyo (JP)

(72) Inventors: Kazuki Nishimura, Sodegaura (JP); Mitsunori Ito, Sodegaura (JP); Tetsuya Inoue, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 295 days.

(21) Appl. No.: 14/649,436

(22) PCT Filed: Dec. 5, 2013

(86) PCT No.: PCT/JP2013/007162
§ 371 (c)(1),
(2) Date: Jun. 3, 2015

(87) PCT Pub. No.: WO2014/087657
PCT Pub. Date: Jun. 12, 2014

(65) Prior Publication Data
US 2015/0325794 A1     Nov. 12, 2015

(30) Foreign Application Priority Data

Dec. 7, 2012  (JP) ................. 2012-268553

(51) Int. Cl.
*H01L 51/00* (2006.01)
*C07D 403/10* (2006.01)
(Continued)

(52) U.S. Cl.
CPC ........ *H01L 51/0061* (2013.01); *C07D 403/04* (2013.01); *C07D 403/10* (2013.01);
(Continued)

(58) Field of Classification Search
CPC ............. H01L 51/0061; H01L 51/0067; H01L 51/0071; H01L 51/0072; H01L 51/5012;
(Continued)

(56) References Cited

U.S. PATENT DOCUMENTS

2012/0001154 A1    1/2012  Kato
2012/0211736 A1*   8/2012  Kim ................ C09K 11/06
                                                     257/40
(Continued)

FOREIGN PATENT DOCUMENTS

JP    2014-111556 A    6/2014
KR    2011-0041727 A    4/2011
(Continued)

OTHER PUBLICATIONS

Office Action issued in Japanese Patent Application No. 2014-550933 dated Feb. 14, 2017.
(Continued)

*Primary Examiner* — Ruiyun Zhang
(74) *Attorney, Agent, or Firm* — Foley & Lardner LLP

(57) ABSTRACT

An aromatic amine derivative represented by the following formula (1). In the formula, $Ar^1$ and $Ar^2$ are independently a substituted or unsubstituted aryl group including 6 to 60 ring carbon atoms; $L^1$ is a substituted or unsubstituted arylene group including 6 to 60 ring carbon atoms; $L^2$ is a single bond or a substituted or unsubstituted arylene group including 6 to 60 ring carbon atoms; $R^1$ and $R^2$ are independently a substituted or unsubstituted aryl group including 6 to 60 ring carbon atoms or the like; n is an integer of 0 to 3; m is an integer of 0 to 4; $X^1$ to $X^5$ are independently a nitrogen atom or $CR^3$; provided that at least one of $X^1$ to $X^5$ are a nitrogen atom; $R^3$ is a hydrogen atom, a substituted or unsubstituted aryl group including 6 to 60 ring carbon atom or the like.

(Continued)

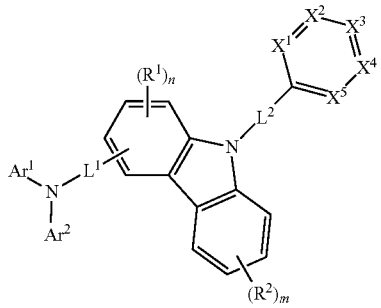

(1)

21 Claims, 1 Drawing Sheet

(51) Int. Cl.
*C07D 403/04* (2006.01)
*C09K 11/06* (2006.01)
*H05B 33/14* (2006.01)
*H01L 51/50* (2006.01)

(52) U.S. Cl.
CPC .............. *C09K 11/06* (2013.01); *H05B 33/14* (2013.01); *C09K 2211/1007* (2013.01); *C09K 2211/1011* (2013.01); *C09K 2211/1014* (2013.01); *C09K 2211/1029* (2013.01); *C09K 2211/1044* (2013.01); *C09K 2211/1059* (2013.01); *H01L 51/0067* (2013.01); *H01L 51/0072* (2013.01); *H01L 51/5012* (2013.01); *H01L 51/5016* (2013.01); *H01L 2251/308* (2013.01)

(58) Field of Classification Search
CPC . H01L 51/501; C07D 403/04; C07D 403/106; C09K 11/06; C09K 2211/1007; C09K 2211/1011; C09K 2211/1014; C09K 2211/1029; C09K 2211/1059

USPC .................. 428/690, 917; 257/40, E51.028; 544/180, 284, 212; 548/440
See application file for complete search history.

(56) References Cited

U.S. PATENT DOCUMENTS

| | | |
|---|---|---|
| 2014/0018536 A1 | 1/2014 | Kato |
| 2014/0151667 A1 | 6/2014 | Miyata |
| 2014/0158992 A1* | 6/2014 | Xia ................... H01L 51/0072 257/40 |
| 2015/0069350 A1 | 3/2015 | Kim et al. |
| 2015/0133662 A1 | 5/2015 | Ahn et al. |
| 2015/0159084 A1 | 6/2015 | Cho et al. |

FOREIGN PATENT DOCUMENTS

| | | | |
|---|---|---|---|
| KR | 20110041727 A | * | 4/2011 |
| KR | 10-1072817 B1 | | 10/2011 |
| KR | 10-1111406 B1 | | 4/2012 |
| KR | 10-1181281 B1 | | 9/2012 |
| KR | 10-2013-0139535 A | | 12/2013 |
| KR | 2013-0134426 A | | 12/2013 |
| KR | 10-2014-0012440 A | | 2/2014 |
| WO | WO 2009/061145 A1 | | 5/2009 |
| WO | WO 2009/061156 A1 | | 5/2009 |
| WO | WO 2010/110553 A2 | | 9/2010 |
| WO | WO 2012/001969 A1 | | 1/2012 |
| WO | WO 2012/043996 A2 | | 4/2012 |
| WO | WO 2013/027902 A1 | | 2/2013 |
| WO | WO 2013/187689 A1 | | 12/2013 |
| WO | WO 2013/191409 A1 | | 12/2013 |
| WO | WO-2014/014310 A1 | | 1/2014 |

OTHER PUBLICATIONS

Translation of the International Preliminary Report on Patentability dated Jun. 18, 2015 and the Written Opinion dated Feb. 25, 2014 corresponding to Application No. PCT/JP2013/007162.

* cited by examiner

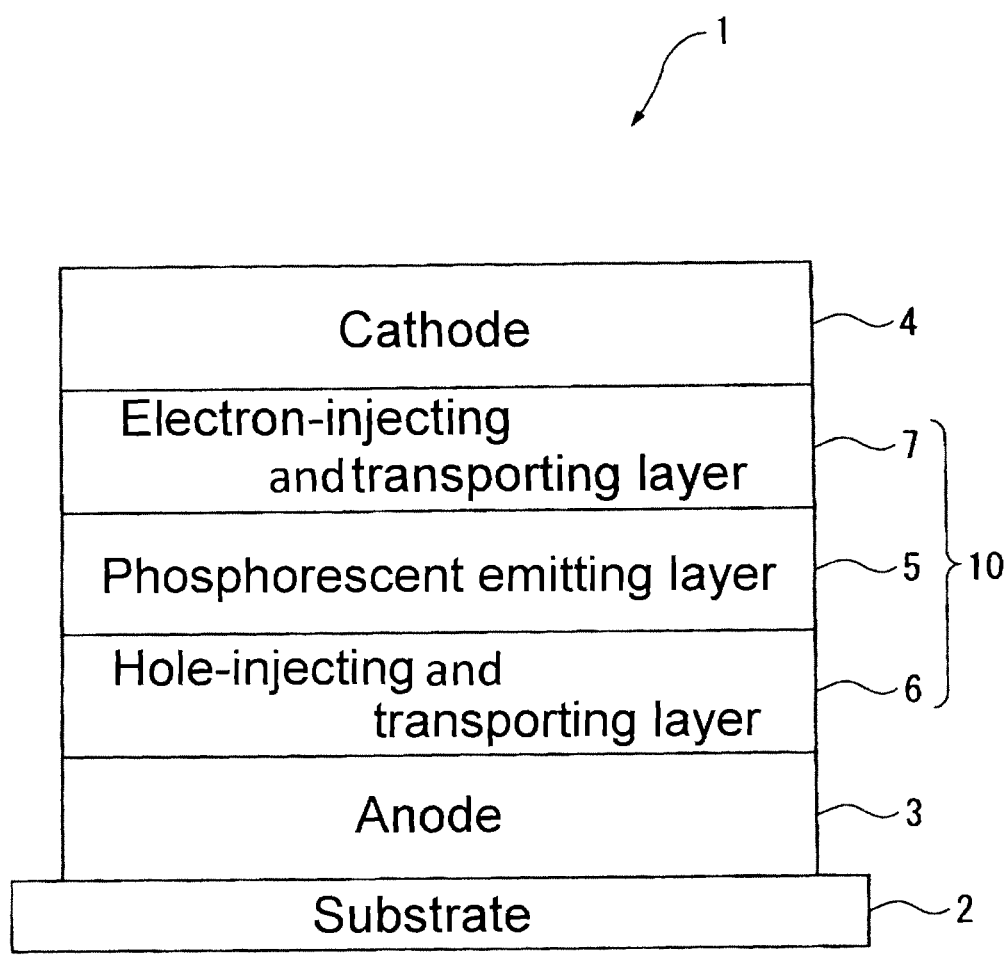

AROMATIC AMINE DERIVATIVE AND ORGANIC ELECTROLUMINESCENT ELEMENT

TECHNICAL FIELD

The invention relates to an aromatic amine derivative and an organic electroluminescence device comprising the same.

BACKGROUND ART

An organic electroluminescence (EL) device is regarded as a promising solid-emitting inexpensive large-area full color display device, and various developments have been conducted so far. In general, an organic EL device comprises an emitting layer and a pair of opposing electrodes that sandwich the emitting layer. When an electrical field is applied between the both electrodes, electrons are injected from the cathode and holes are injected from the anode. Further, these electrons are re-combined with the holes in the emitting layer, create an excited state, and energy is emitted as light when the excited state is returned to the ground state.

Organic EL devices in early stages are insufficient in respect of driving voltage, luminous efficiency and durability. In order to solve this problems, various technical improvements have been made so far.

Improvement in luminous efficiency of an EL device is an important subject that leads to lowering in power consumption of a display, and further improvement has been required.

Patent Document 1 discloses an amine compound comprising a heterocyclic ring.

RELATED ART DOCUMENTS

Patent Documents

Patent Document 1: WO2012/001969

SUMMARY OF THE INVENTION

An object of the invention is to provide an aromatic amine derivative that has an excellent luminous efficiency when used in an organic EL device.

According to the invention, the following aromatic amine derivative or the like are provided.

1. An aromatic amine derivative represented by the following formula (1):

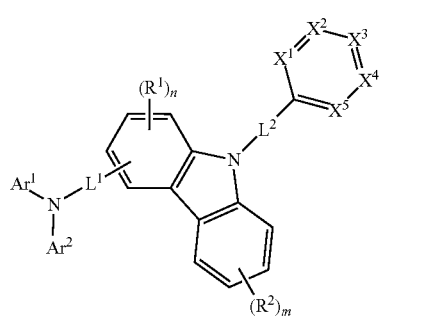

wherein in the formula (1), $Ar^1$ and $Ar^2$ are independently a substituted or unsubstituted aryl group including 6 to 60 ring carbon atoms; $L^1$ is a substituted or unsubstituted arylene group including 6 to 60 ring carbon atoms; $L^2$ is a single bond or a substituted or unsubstituted arylene group including 6 to 60 ring carbon atoms; $R^1$ and $R^2$ are independently a substituted or unsubstituted aryl group including 6 to 60 ring carbon atoms, a substituted or unsubstituted alkyl group including 1 to 50 carbon atoms, a substituted or unsubstituted heteroaryl group including 5 to 30 ring atoms, a substituted or unsubstituted alkoxy group including 1 to 50 carbon atoms, a substituted or unsubstituted aryloxy group including 6 to 60 ring carbon atoms, a halogen atom or a cyano group; n is an integer of 0 to 3; m is an integer of 0 to 4; when plural $R^1$s are present, the plural $R^1$s may be the same or different; when plural $R^2$s are present, the plural $R^2$s may be the same or different; $X^1$ to $X^5$ are independently a nitrogen atom or $CR^3$; provided that at least one of $X^1$ to $X^5$ are a nitrogen atom; $R^3$ is a hydrogen atom, a substituted or unsubstituted aryl group including 6 to 60 ring carbon atoms, a substituted or unsubstituted alkyl group including 1 to 50 carbon atoms, a substituted or unsubstituted alkoxy group including 1 to 50 carbon atoms, a substituted or unsubstituted aryloxy group including 6 to 60 ring carbon atoms, a halogen atom or a cyano group; when plural $R^3$s are present, the plural $R^3$s may be the same or different; and the plural $R^3$s may be bonded to each other to form a ring structure.

2. The aromatic amine derivative according to 1, wherein at least one of $X^1$, $X^2$ and $X^3$ is a nitrogen atom.
3. The aromatic amine derivative according to 1 or 2, wherein at least two of $X^1$ to $X^5$ are a nitrogen atom.
4. The aromatic amine derivative according to any one of 1 to 3, wherein $L^2$ is a single bond.
5. The aromatic amine derivative according to any one of 1 to 4, wherein two or three of $X^1$ to $X^5$ are a nitrogen atom.
6. The aromatic amine derivative according to any one of 1 to 5, wherein $Ar^1$ and $Ar^2$ do not comprise a fluorene structure.
7. The aromatic amine derivative according to any one of 1 to 6, that is represented by the following formula (1-1) or (1-2):

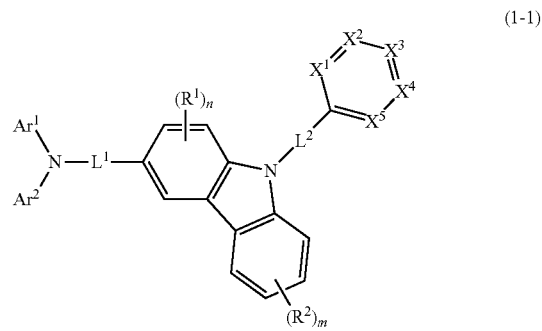

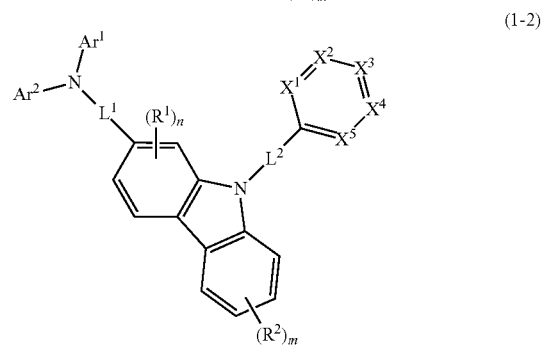

wherein in the formulas (1-1) and (1-2), $Ar^1$, $Ar^2$, $L^1$, $L^2$, $R^1$, $R^2$, n, m, $X^1$ to $X^5$ and $R^3$ are as defined in the formula (1).
8. A material for an organic electroluminescent device comprising the aromatic amine derivative according to any one of 1 to 7.
9. An organic electroluminescence device comprising:
   an anode;
   a cathode; and
   one or more organic layers including an emitting layer between the anode and the cathode,
   wherein at least one of the organic layers comprises the aromatic amine derivative according to any one of 1 to 7.
10. The organic electroluminescence device according to 9, wherein the aromatic amine derivative is contained in the emitting layer.
11. The organic electroluminescence device according to 9 or 10, wherein the emitting layer comprises a phosphorescent emitting material.

According to the invention, an aromatic amine derivative that exhibits excellent luminous efficiency when used in an organic EL device can be provided.

BRIEF DESCRIPTION OF THE DRAWINGS

FIG. 1 is a schematic cross-sectional view showing one example of the organic EL device of the invention.

MODE FOR CARRYING OUT THE INVENTION

The aromatic amine derivative according to one embodiment of the invention is represented by the following formula (1):

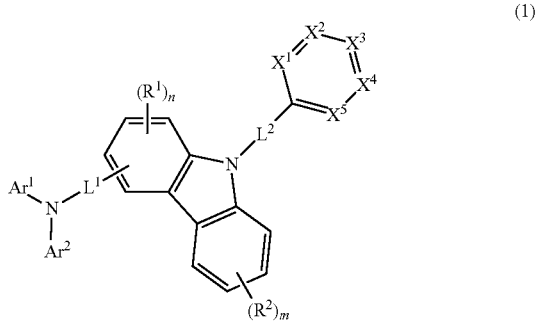

(1)

wherein in the formula (1), $Ar^1$ and $Ar^2$ are independently a substituted or unsubstituted aryl group including 6 to 60 carbon atoms that form a ring (hereinafter referred to as the "ring carbon atoms"); $L^1$ is a substituted or unsubstituted arylene group including 6 to 60 ring carbon atoms; $L^2$ is a single bond or a substituted or unsubstituted arylene group including 6 to 60 ring carbon atoms;
$R^1$ and $R^2$ are independently a substituted or unsubstituted aryl group including 6 to 60 ring carbon atoms, a substituted or unsubstituted alkyl group including 1 to 50 carbon atoms, a substituted or unsubstituted heteroaryl group including 5 to 30 atoms that form a ring (hereinafter referred to as the "ring atoms"), a substituted or unsubstituted alkoxy group including 1 to 50 carbon atoms, a substituted or unsubstituted aryloxy group including 6 to 60 ring carbon atoms, a halogen atom or a cyano group; n is an integer of 0 to 3; m is an integer of 0 to 4; when plural $R^1$s are present, the plural $R^1$s may be the same or different; when plural $R^2$s are present, the plural $R^2$s may be the same or different;
$X^1$ to $X^5$ are independently a nitrogen atom or $CR^3$, provided that at least one of $X^1$ to $X^5$ is a nitrogen atom;
$R^3$ is a hydrogen atom, a substituted or unsubstituted aryl group including 6 to 60 ring carbon atoms, a substituted or unsubstituted alkyl group including 1 to 50 carbon atoms, a substituted or unsubstituted alkoxy group including 1 to 50 carbon atoms, a substituted or unsubstituted aryloxy group including 6 to 60 ring carbon atoms, a halogen atom or a cyano group, when plural $R^3$s are present, the plural $R^3$s may be the same or different, and the plural $R^3$s may be bonded to each other to form a ring structure.

In the aromatic amine derivative according to one embodiment of the invention, a triarylamine part (-$L^1$-N($Ar^1$)($Ar^2$)) functions as a hole-transporting part and a six-membered ring (azine ring) part including $X_1$ to $X_5$ functions as an electron-transporting part. Due to a structure in which the hole-transporting unit and the electron-transporting unit are present in combination (that is, the derivative has bipolar properties), the compound of the invention is excellent in carrier balance, has a high possibility of recombination and has an excellent luminous efficiency.

In general, in order to allow a part to be a hole-transporting part (having a high resistance to holes), the part is required to be highly resistant under oxidizing conditions in which holes are generated. It is considered that, if an alkyl or a heteroaryl (carbazole or the like) is directly bonded to an amine, the electron density is increased, and the amine does not have resistance to oxidation.

It is considered that, in order to increase the resistance, an aryl group having a neutral electron density is required to be directly bonded to an amine. It is considered that, since the aromatic amine derivative according to one embodiment of the invention comprises an arylene ($L^1$) that is directly bonded to an amine (—N($Ar^1$)($Ar^2$)) as an essential component, the triarylamine part can become a hole-transporting part.

It is considered that, if an alkyl or a heteroaryl substitutes on the aryl group that is directly bonded to an amine, the electron density is not increased, and the amine has resistance.

Due to the presence of the arylene ($L^1$), the hole-transporting unit and the electron-transporting unit can be separated in respect of function, whereby bipolar properties can be exhibited.

As mentioned above, the aromatic amine derivative according to one embodiment of the invention has resistance to carriers. Therefore, it is considered that, when used in a hole-transporting layer or a hole-injecting layer, the derivative can prevent deterioration of these layers, resulting in a prolonged life of a device.

Since the aromatic amine derivative according to one embodiment of the invention can transport both of holes and electrons, it can be used not only as a material for an emitting layer of an organic EL device, but also as a hole-transporting material or an electron-transporting material, and further, as a material for a carrier-barrier layer. Due to its high carrier-transporting ability, an organic EL device can be driven at a low voltage. Due to its wide energy gap, it is possible to adjust carrier balance. As a result, an organic EL device can have a high luminous efficiency and a long life.

Further, the aromatic amine derivative according to one embodiment of the invention can be used as a phosphorescent host or the like. Since this amine derivative has excellent carrier balance, recombination possibility is improved, leading to an increase in efficiency. In addition, since emission does not tend to occur mainly in a region nearer to a hole-transporting layer, deterioration of a hole-transporting layer can be prevented, whereby the life can be prolonged.

$L^1$ is preferably a substituted or unsubstituted arylene group including 6 to 30 ring carbon atoms, more preferably a substituted or unsubstituted arylene group including 6 to 20 ring carbon atoms, and particularly preferably any one of a substituted or unsubstituted phenylene group, a substituted or unsubstituted biphenylene group and a substituted or unsubstituted fluorenylene group.

Specific examples of $L^1$ are given below, but $L^1$ is not restricted thereto.

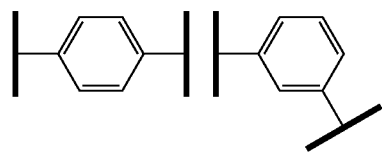

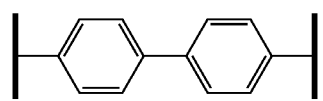

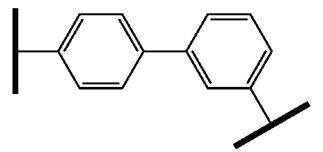

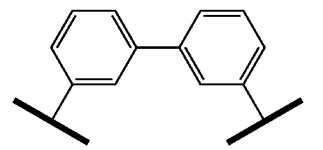

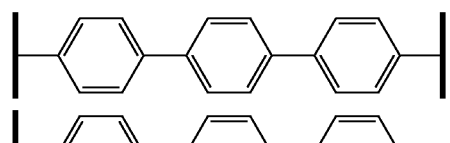

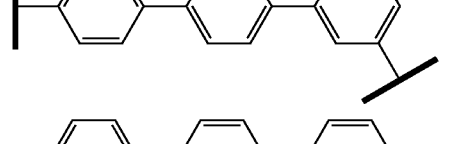

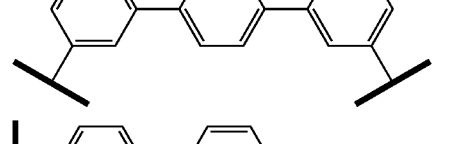

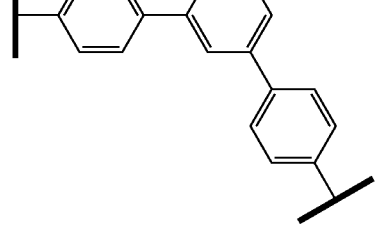

-continued

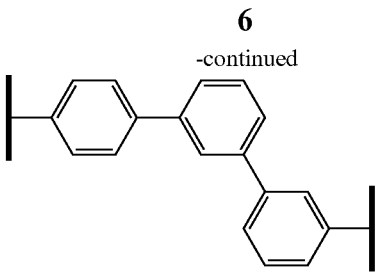

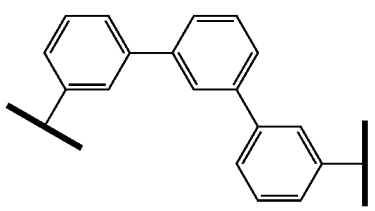

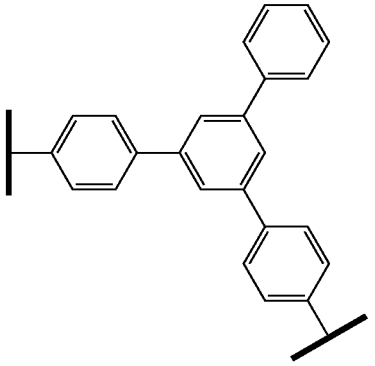

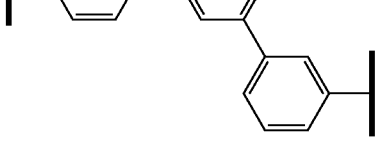

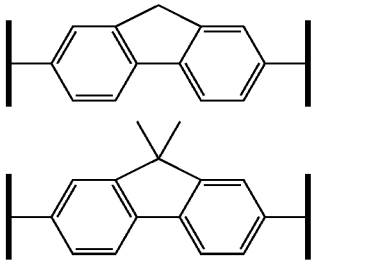

-continued

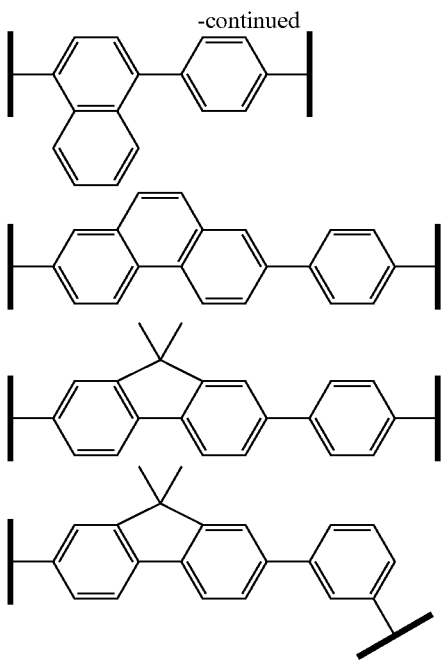

L² is preferably a single bond, or a substituted or unsubstituted arylene group including 6 to 30 ring carbon atoms, more preferably a single bond, or a substituted or unsubstituted arylene group including 6 to 20 ring carbon atoms, more preferably any of a single bond, a substituted or unsubstituted phenylene group and a substituted or unsubstituted biphenylene group and a substituted or unsubstituted fluorenylene group, particularly preferably a single bond.

However, when the compound represented by the formula (1) is used as the material of an electron-transporting zone mentioned later, L² is particularly preferably the arylene group mentioned above.

It is preferred that at least one of X² and X³ be a nitrogen atom.

In addition, it is preferred that at least two of X¹ to X⁵ be a nitrogen atom. It is more preferred that two or three of them be a nitrogen atom.

Specifically, among X¹ to X⁵, it is preferred that the following combinations be nitrogen atoms: X¹ and X³; X¹ and X⁵; or X¹, X³ and X⁵.

As for X¹ to X⁵ which is not a nitrogen atom, i.e. CR³, R³ is preferably a hydrogen atom or a substituted or unsubstituted aryl group including 6 to 60 ring carbon atoms, more preferably a substituted or unsubstituted aryl group including 6 to 20 ring carbon atoms, further preferably an aryl group including 6 to 15 ring carbon atoms, and particularly preferably a substituted or unsubstituted phenyl group, a substituted or unsubstituted naphthyl group or a substituted or unsubstituted fluorenyl group. When plural R³s are bonded to form a ring, the ring may be a saturated or unsaturated six-membered ring, and the six-membered ring may comprise one or two or more nitrogen atoms.

Ar¹ and Ar² are preferably independently a substituted or unsubstituted aryl group including 6 to 30 ring carbon atoms, more preferably independently a substituted or unsubstituted aryl group including 6 to 20 ring carbon atoms, and particularly preferably independently a substituted or unsubstituted phenyl group, a substituted or unsubstituted biphenyl group, a substituted or unsubstituted naphthyl group or a substituted or unsubstituted terphenyl group.

It is preferred that Ar¹ and Ar² do not comprise a fluorene structure.

R¹ and R² are independently preferably a substituted or unsubstituted aryl group including 6 to 60 ring carbon atoms or a substituted or unsubstituted alkyl group including 1 to 50 carbon atoms. Specifically, a substituted or unsubstituted phenyl group, a substituted or unsubstituted biphenyl group, a substituted or unsubstituted methyl group, a substituted or unsubstituted ethyl group, a substituted or unsubstituted propyl group and a substituted or unsubstituted butyl group are preferable.

It is preferred that n and m be independently 0 to 2.

The aromatic amine derivative according to one embodiment of the invention is preferably represented by the following formula (1-1) or (1-2):

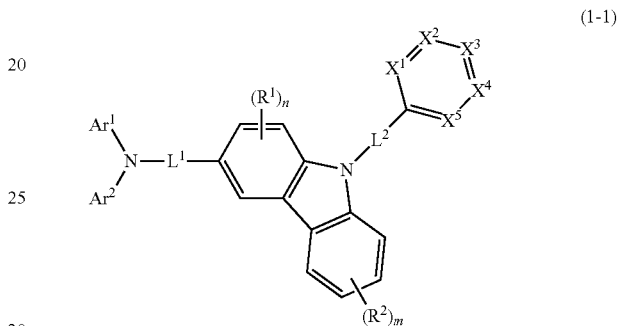

(1-1)

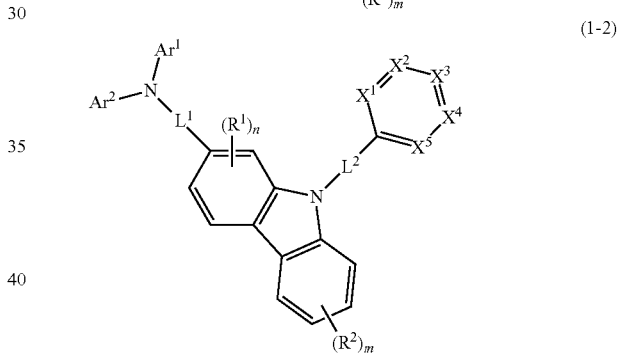

(1-2)

wherein in the formulas (1-1) and (1-2), Ar¹, Ar², L¹, L², R¹, R², n, m, X¹ to X⁵ and R³ are as defined in the formula (1).

In this specification, the "ring carbon atoms" means carbon atoms that constitute a saturated ring, an unsaturated ring or an aromatic ring. The "ring atoms" means carbon atoms and hetero atoms that constitute a ring (including a saturated ring, an unsaturated ring and an aromatic ring).

In this specification, the "a to b carbon atoms" in the "substituted or unsubstituted XX group including a to b carbon atoms" mean the number of carbon atoms when the XX group is unsubstituted, and does not include the number of carbon atoms of the substituent when the XX group is substituted.

In the invention, the hydrogen atom includes isomers differing in the number of neutrons, i.e. protium, deuterium and tritium.

Each group in the above formulas (1), (1-1) and (1-2) and substituents thereof will be explained below in detail.

As the alkyl group, a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group or the like can be mentioned.

The number of carbon atoms is preferably 1 to 10, with 1 to 6 being further preferable. Among these alkyl groups, a methyl group, an ethyl group, a propyl group, an isopropyl group, an n-butyl group, an s-butyl group, an isobutyl group, a t-butyl group, an n-pentyl group and an n-hexyl group are preferable.

As the aryl group, for example, a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a naphthacenyl group, a chrysenyl group, a benzo[c]phenanthryl group, a benzo[g]chrysenyl group, a triphenylenyl group, a 1-fluorenyl group, a 2-fluorenyl group, a 3-fluorenyl group, a 4-fluorenyl group, a 9-fluorenyl group, a benzofluorenyl group, a dibenzofluorenyl group, a 2-biphenylyl group, a 3-biphenylyl group, a 4-biphenylyl group, a terphenyl group, fluoranthenyl group or the like can be given.

As the arylene group, a divalent group corresponding to the above-mentioned aryl groups can be given.

The aryl group preferably includes 6 to 20 ring carbon atoms, more preferably 6 to 12 ring carbon atoms. Among the above-mentioned aryl groups, a phenyl group, a biphenyl group, a tolyl group, a xylyl group, and a 1-naphthyl group are particularly preferable.

As specific examples of the heteroaryl group, a pyrrole ring, an isoindole ring, a benzofuran ring, an isobenzofuran ring, a dibenzothiophene ring, an isoquinoline ring, a quinoxaline ring, a phenanthridine ring, a phenanthroline ring, a pyridine ring, a pyrazine ring, a pyrimidine ring, a pyridazine ring, a triazine ring, an indole ring, a quinoline ring, an acridine ring, a pyrrolidine ring, a dioxane ring, a piperidine ring, a morpholine ring, a piperazine ring, a furan ring, a thiophene ring, an oxazole ring, an oxadiazole ring, a benzoxazole ring, a thiazole ring, a thiadiazole ring, a benzothiazole ring, a triazole ring, an imidazole ring, a benzimidazole ring, a pyran ring, a dibenzofuran ring, a benzo[c]dibenzofuran ring, a carbazole ring and a group formed from derivatives of these rings can be given.

The alkoxy group is represented by —OY. As examples of Y, the examples of the alkyl group given above can be mentioned. The alkoxy group is a methoxy group or an ethoxy group, for example.

The aryloxy group is represented by —OZ. As examples of Z, the examples of the aryl group mentioned above or the examples of the monocyclic group or the fused ring group mentioned later can be mentioned. The aryloxy group is a phenoxy group, for example.

As the halogen atom, fluorine, chlorine, bromine, iodine or the like can be given, with a fluorine atom being preferable.

As the arbitrary substituent of the "substituted or unsubstituted", a halogen atom (fluorine, chlorine, bromine, iodine), a cyano group, an alkyl group including 1 to 20 (preferably 1 to 6) carbon atoms, a cycloalkyl group including 3 to 20 (preferably 5 to 12) carbon atoms, an alkoxy group including 1 to 20 (preferably 1 to 5) carbon atoms, a haloalkyl group including 1 to 20 (preferably 1 to 5) carbon atoms, a haloalkoxy group including 1 to 20 (preferably 1 to 5) carbon atoms, an alkylsilyl group including 1 to 10 (preferably 1 to 5) carbon atoms, an aryl group including 6 to 30 (preferably 6 to 18) ring carbon atoms, an aryloxy group including 6 to 30 (preferably 6 to 18) ring carbon atoms, an arylsilyl group including 6 to 30 (preferably 6 to 18) carbon atoms, an aralkyl group including 7 to 30 (preferably 7 to 20) carbon atoms and a heteroaryl group including 5 to 30 (preferably 5 to 18) ring atoms can be given. These substituents may further be substituted by the above-mentioned arbitrary substituent.

As the alkyl group, the aryl group, the heteroaryl group, the alkoxy group and the aryloxy group as examples of the arbitrary substituent, those mentioned above can be mentioned.

As the cycloalkyl group, those in which the examples of the alkyl group including 3 or more carbon atoms mentioned above form an aliphatic ring structure can be mentioned.

As the haloalkyl group, one in which one or more hydrogen atoms in the above-mentioned alkyl group is substituted by a halogen atom can be mentioned. As the halogen atom, fluorine is preferable. As the haloalkyl group, a trifluoromethyl group, a 2,2-trifluoroethyl group or the like can be mentioned.

As the haloalkoxy group, one in which one or more hydrogen atoms in the above-mentioned alkoxy group is substituted by a halogen atom can be mentioned. As the halogen atom, fluorine is preferable.

As the aralkyl group, one in which the hydrogen atom in the alkyl group mentioned above is substituted by the aryl group mentioned above can be given.

As the alkylsilyl group, a silyl group in which the alkyl group mentioned above is bonded can be given.

As the arylsilyl group, a silyl group in which the aryl group mentioned above is bonded can be given.

Examples of the aromatic amine derivative according to one embodiment of the invention are given below.

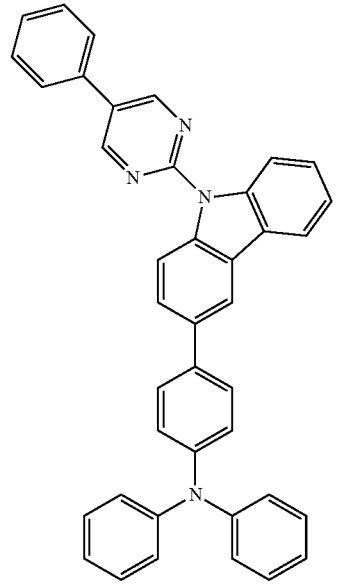

11
-continued
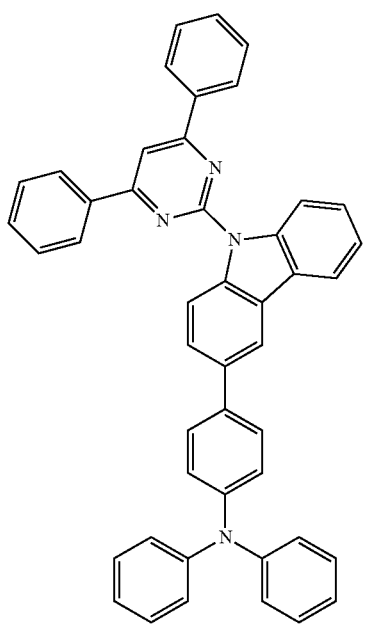
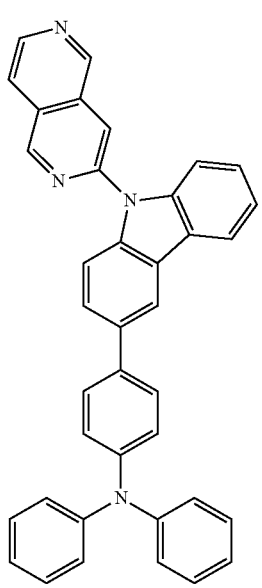
12
-continued
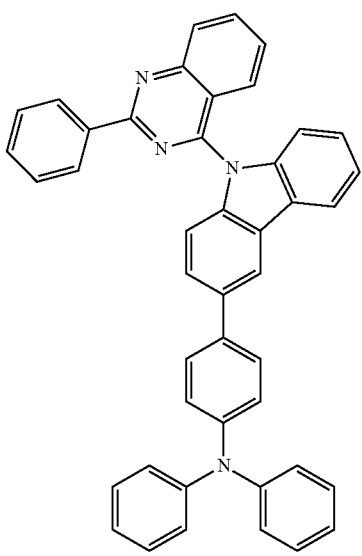
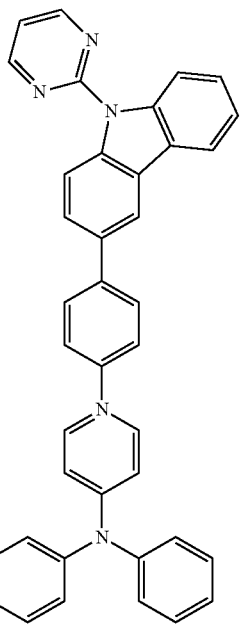

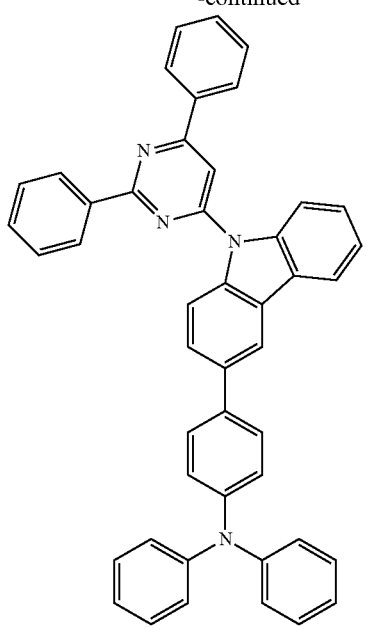
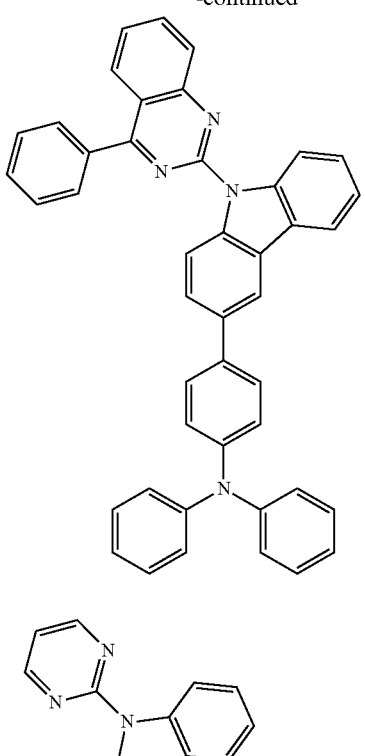
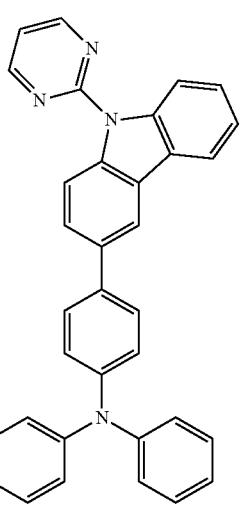
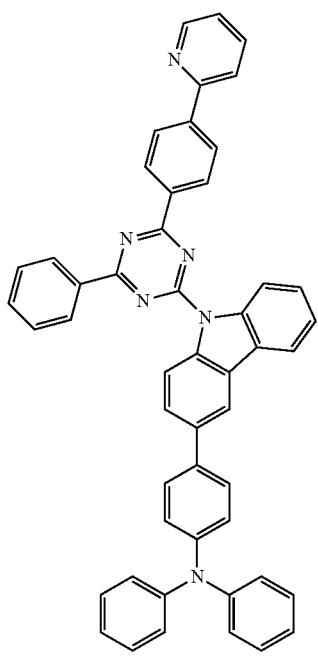
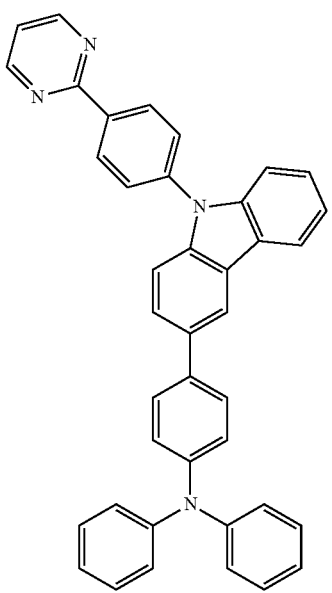

-continued
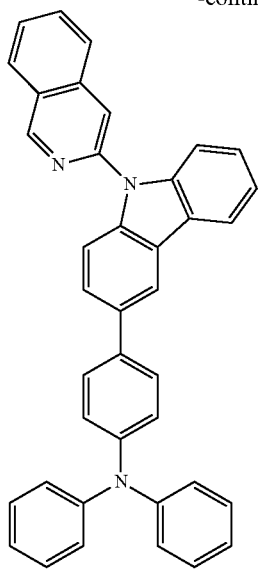
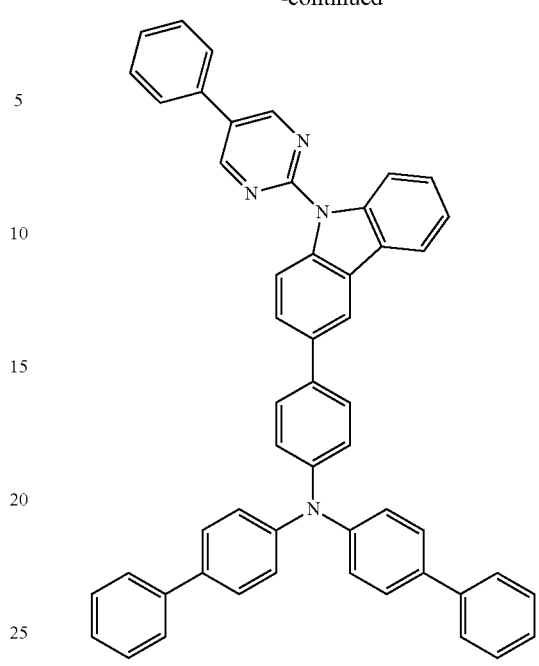
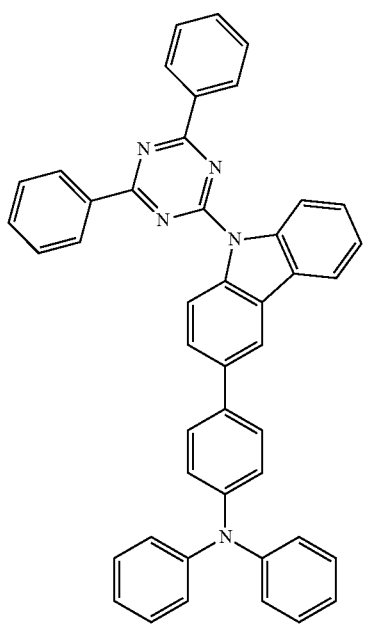
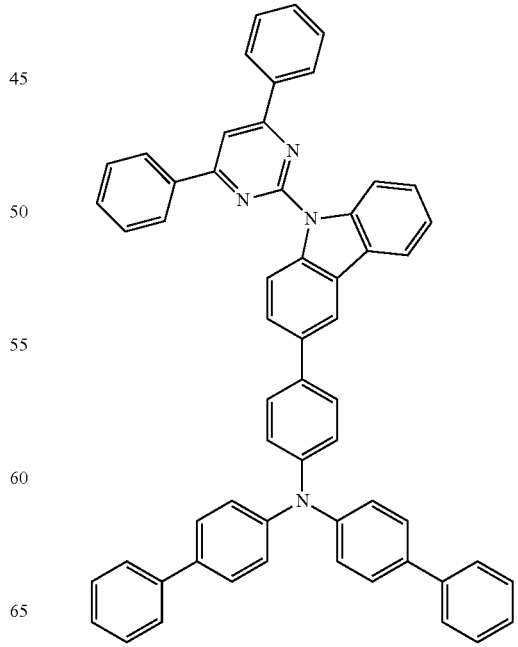

-continued
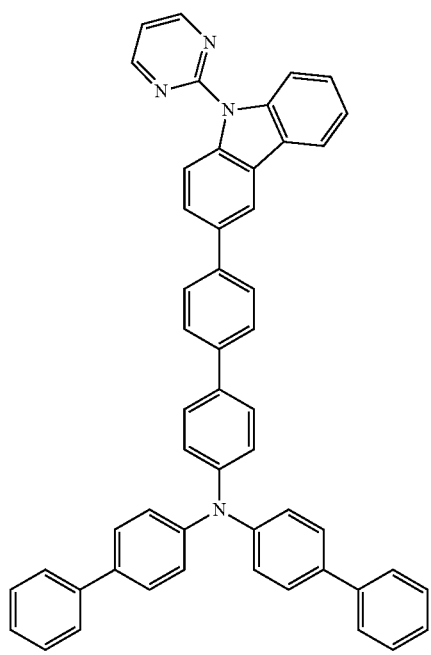
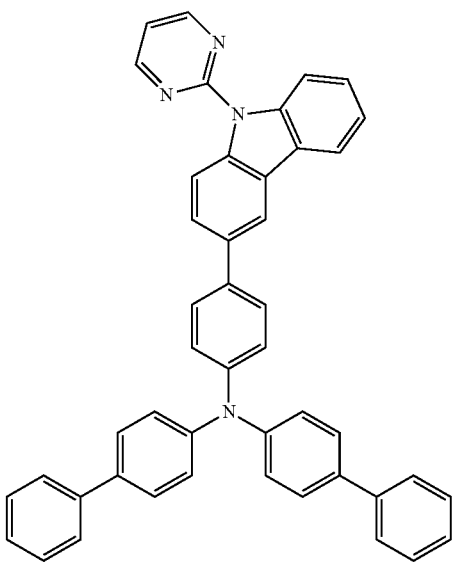
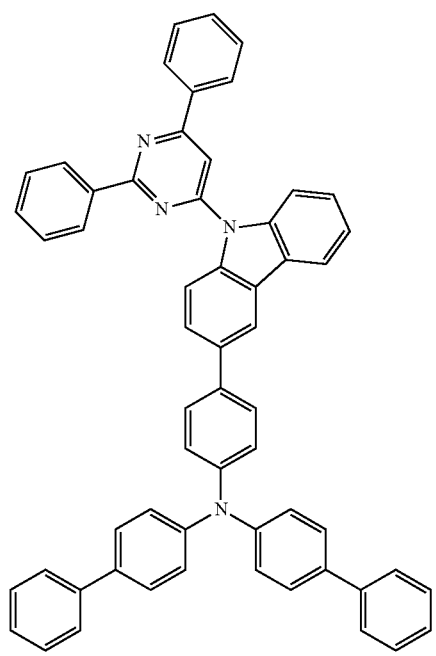
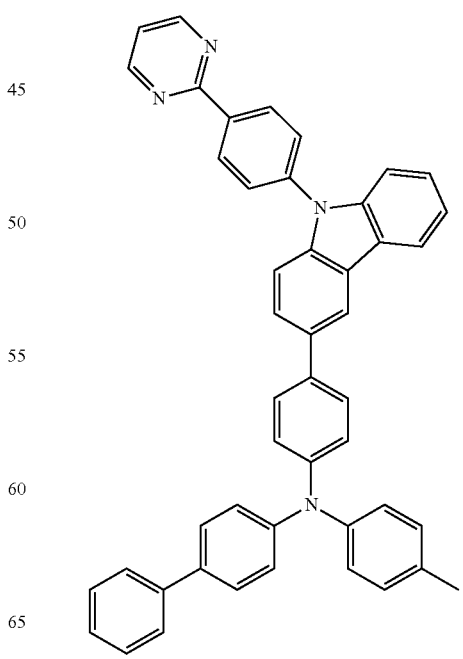

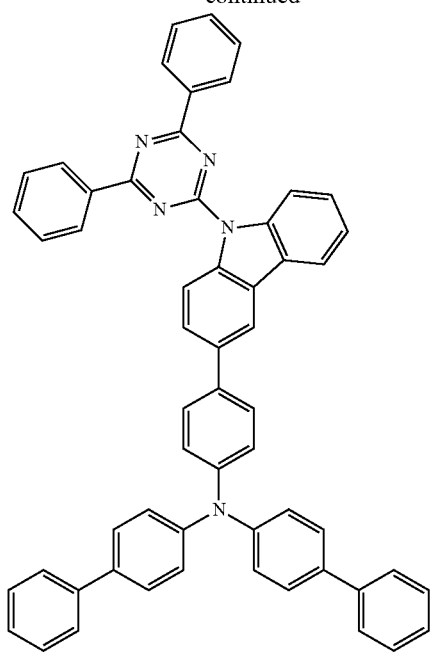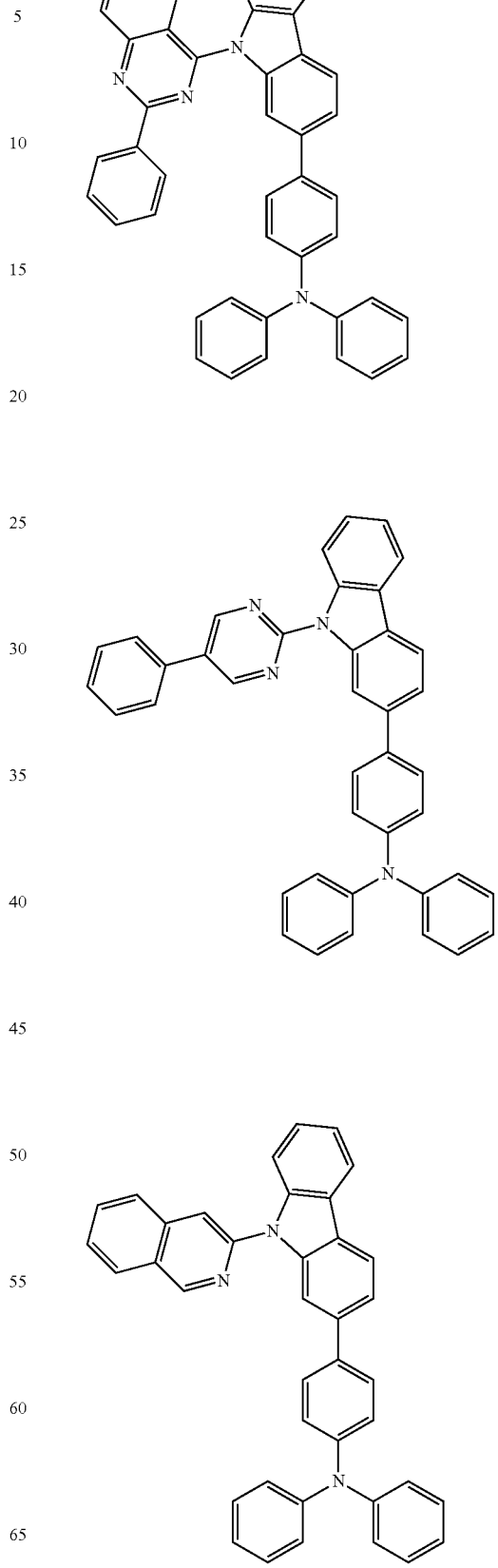

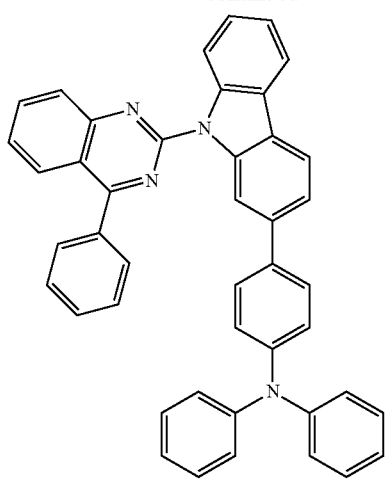
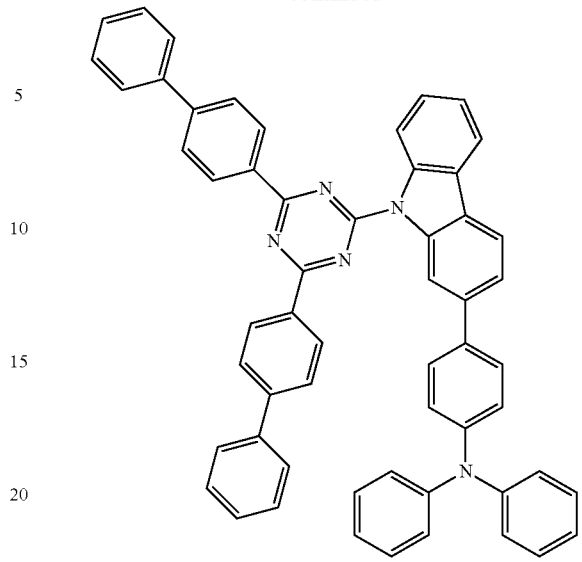
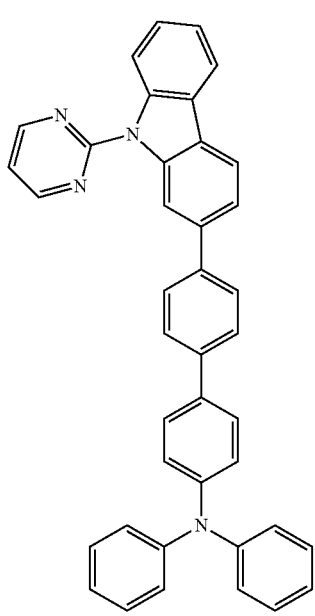
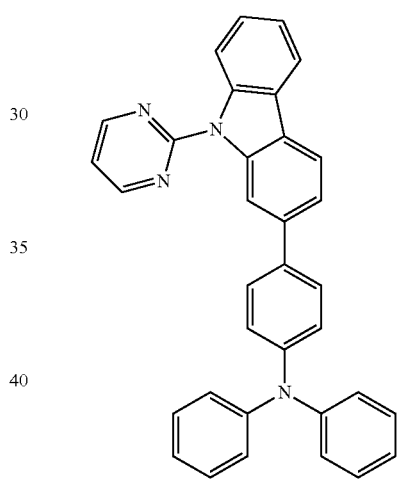
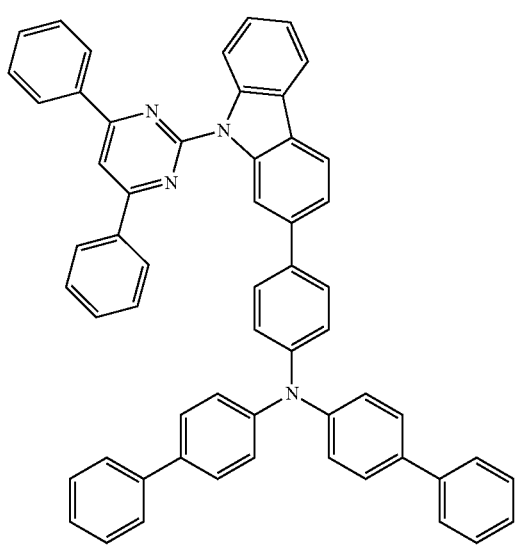
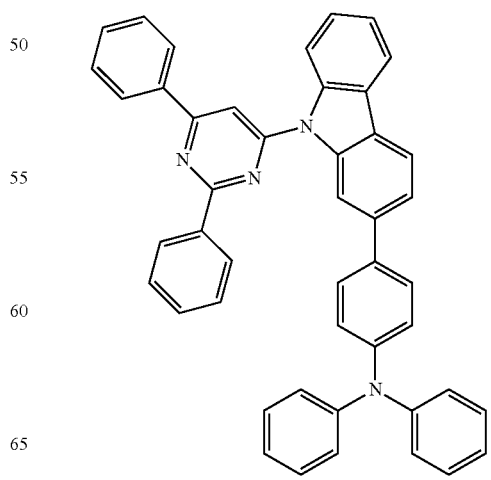

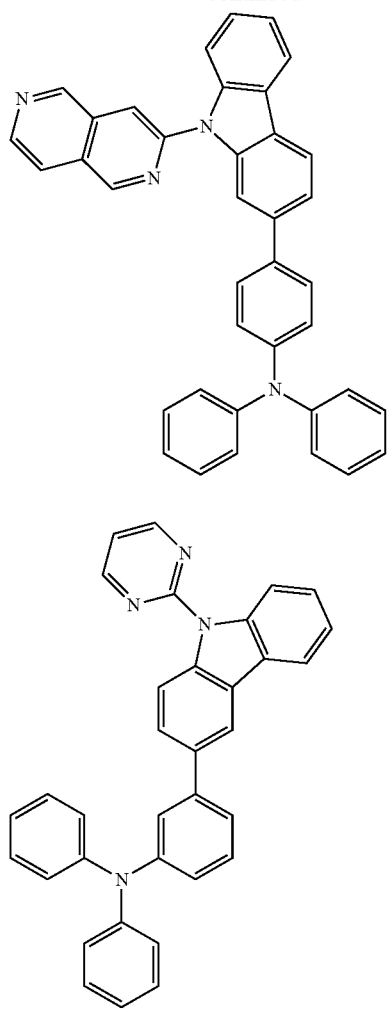
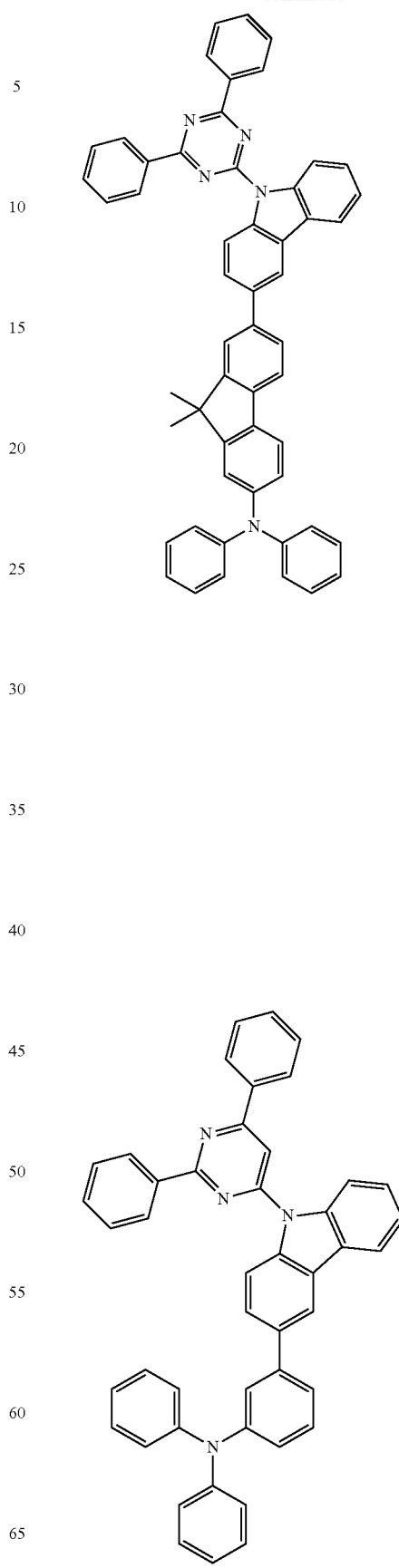

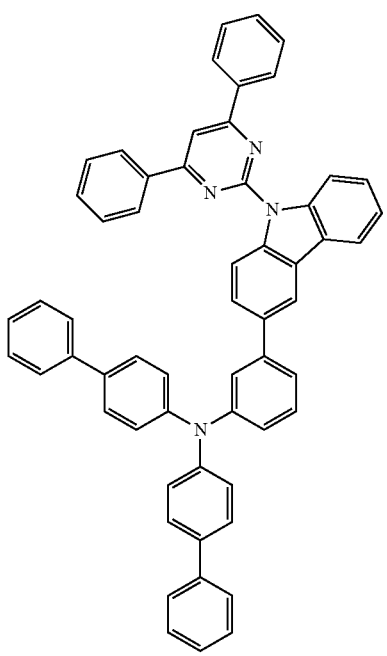
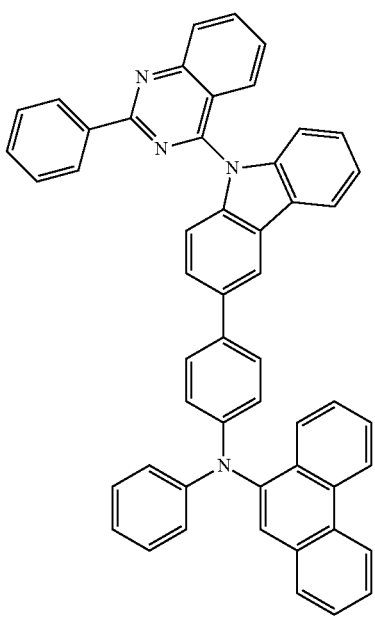
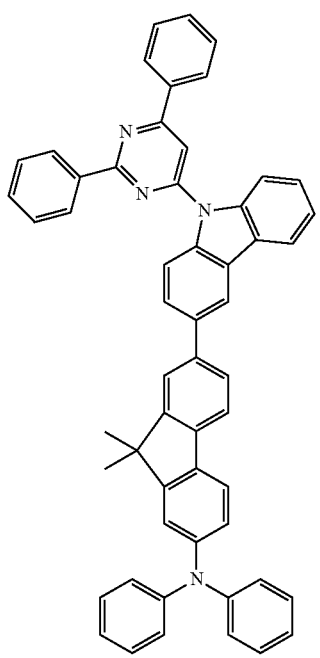
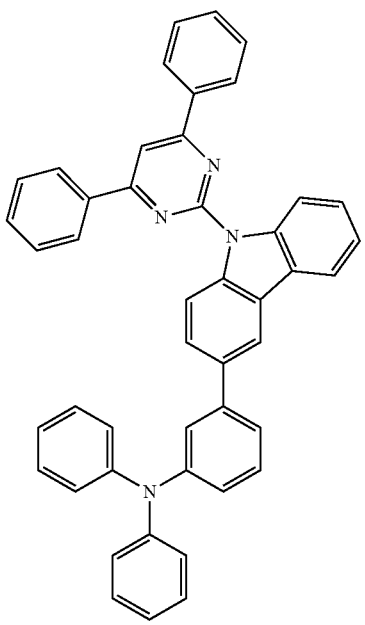

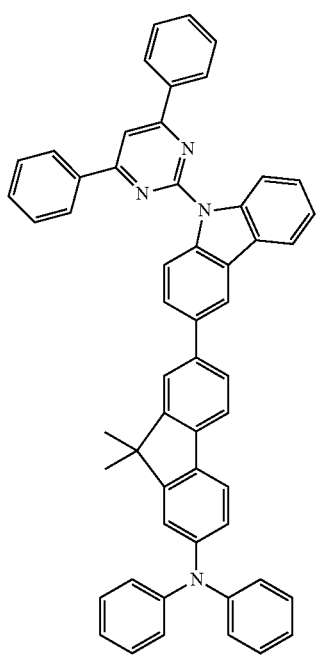
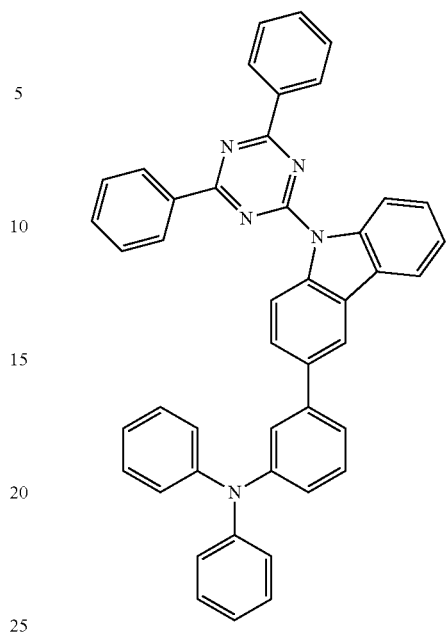
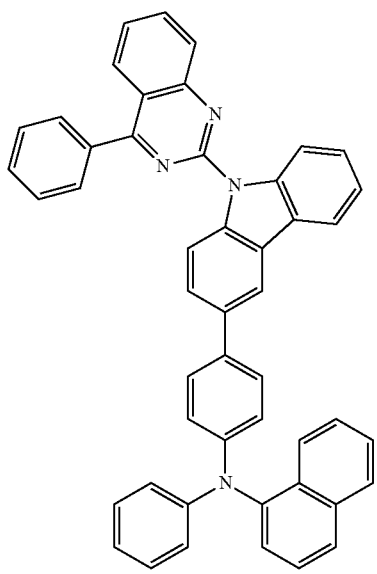
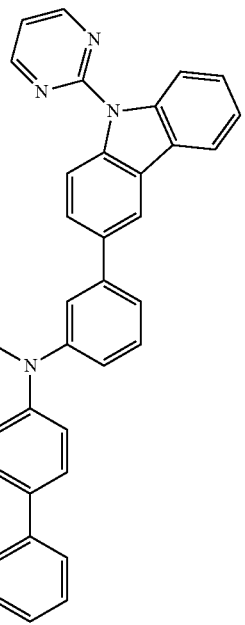

29
-continued
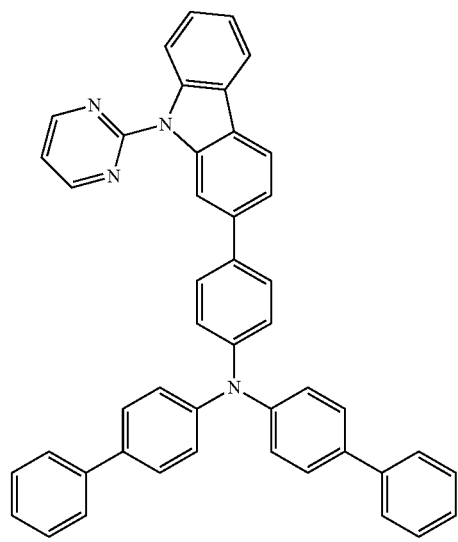
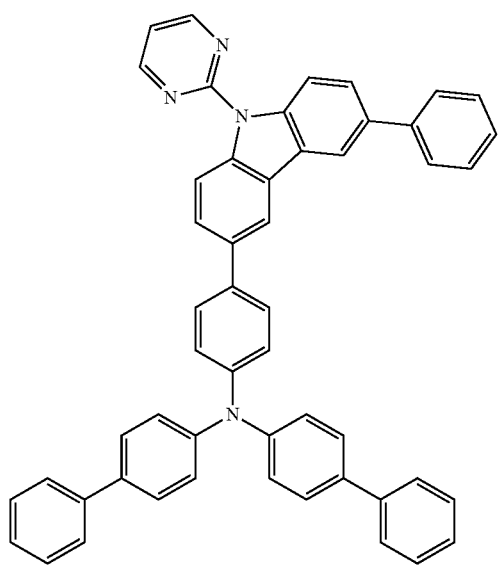
30
-continued
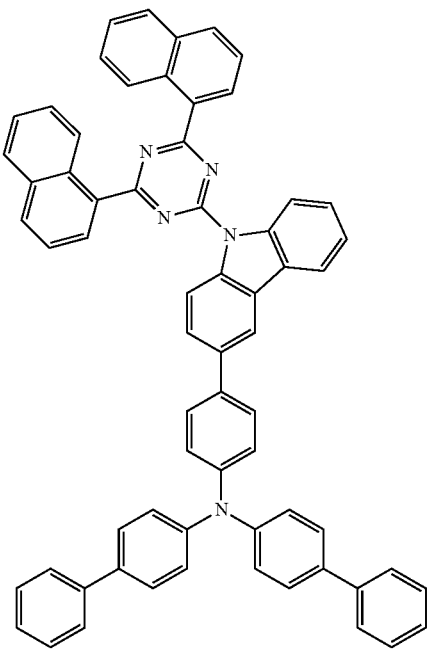
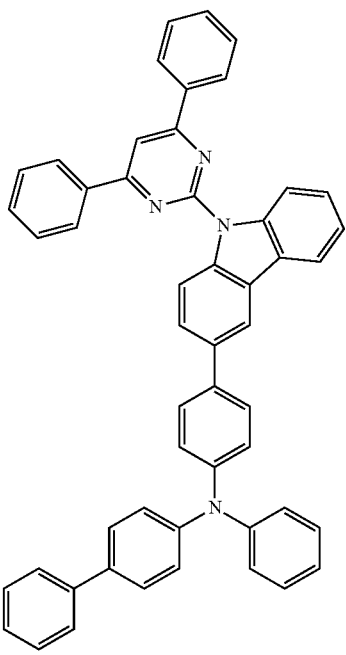

31
-continued
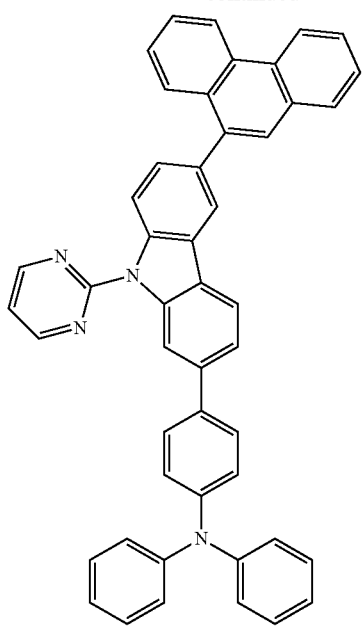
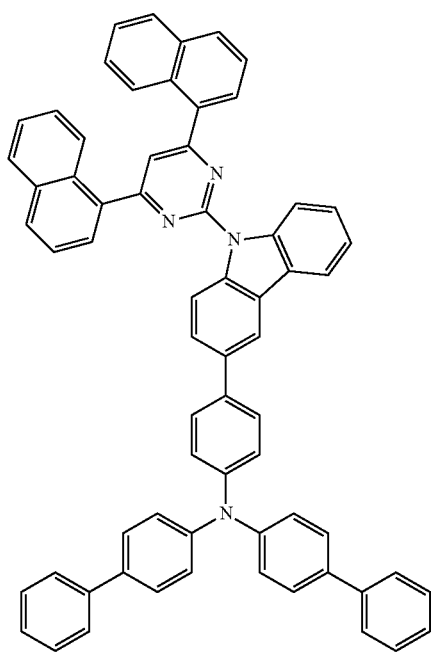
32
-continued
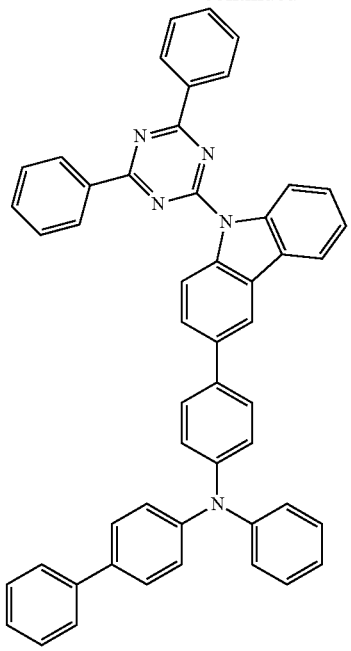
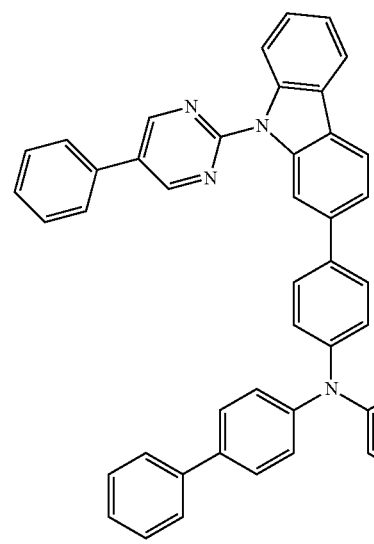

33
-continued
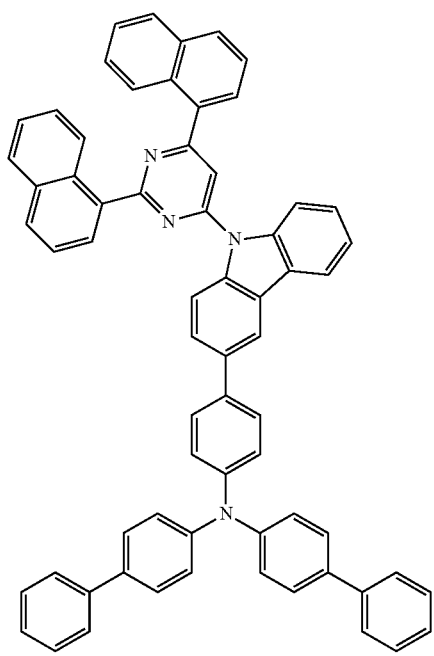
34
-continued
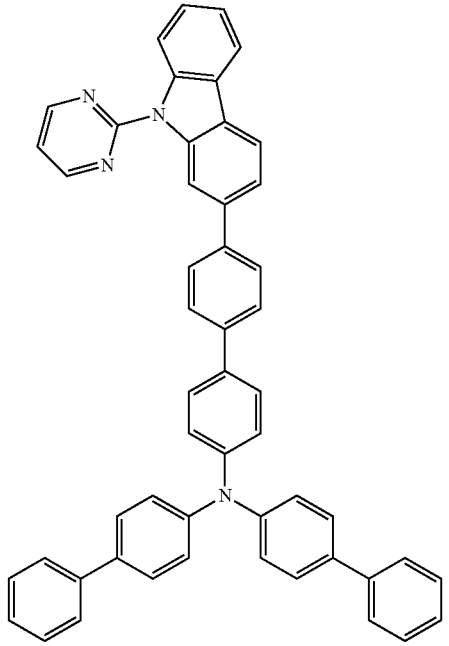
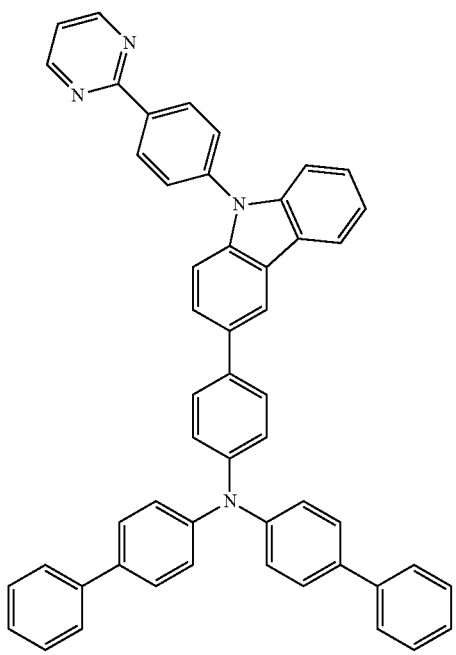
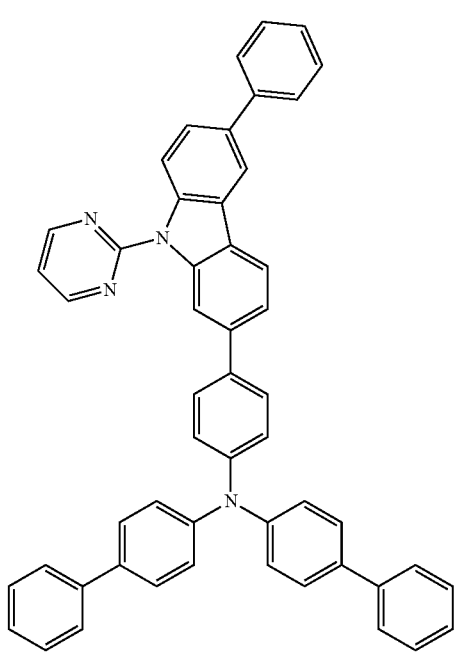

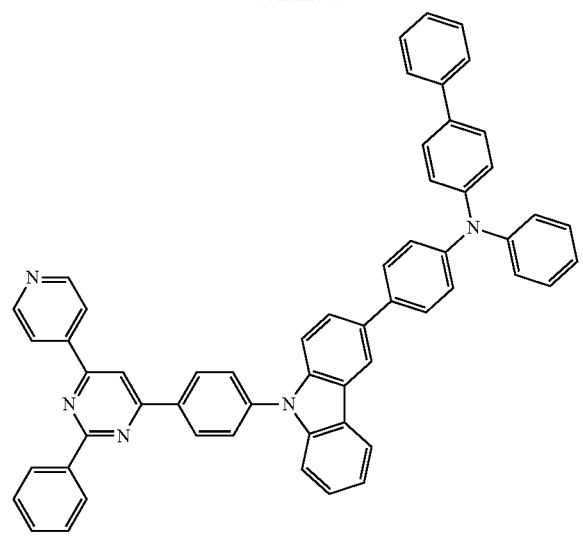
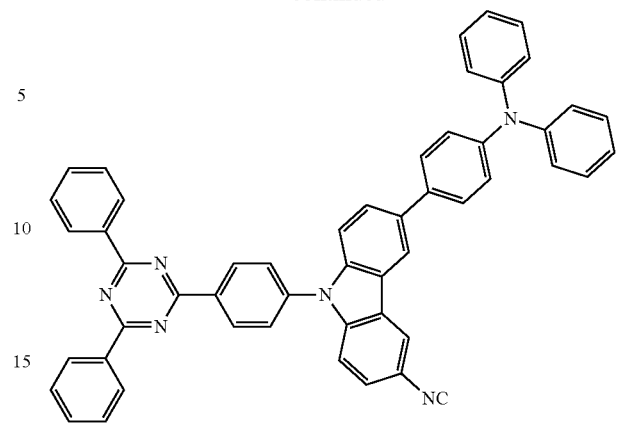
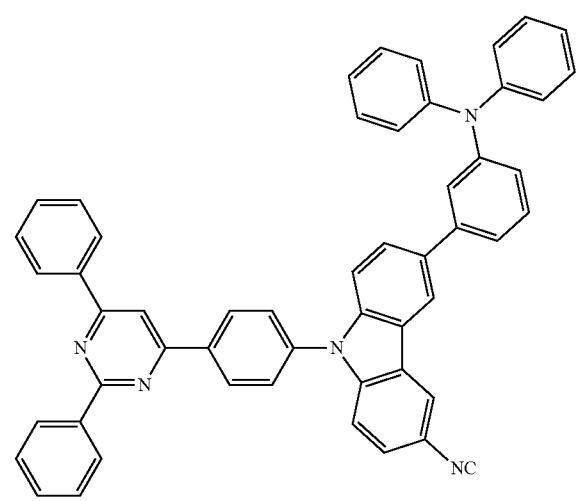
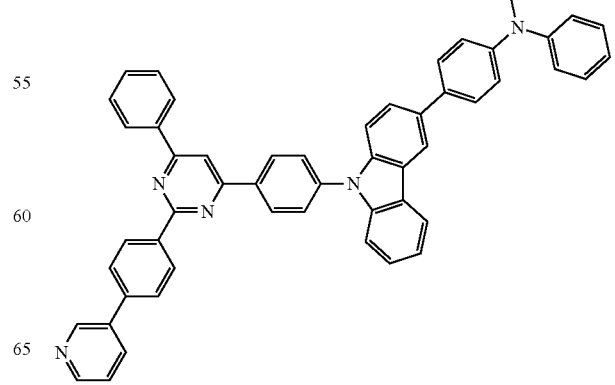
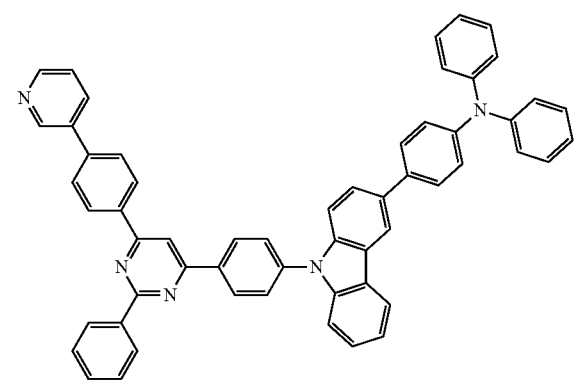

-continued
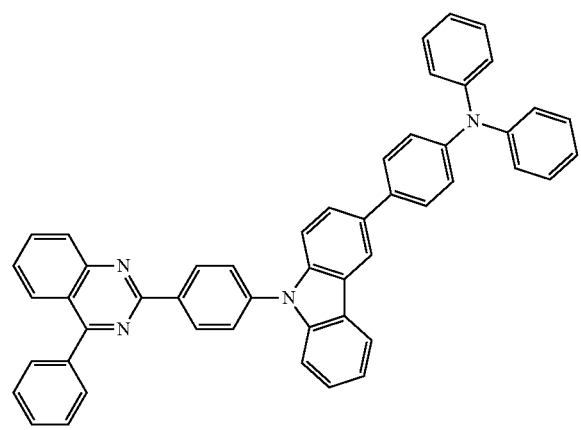
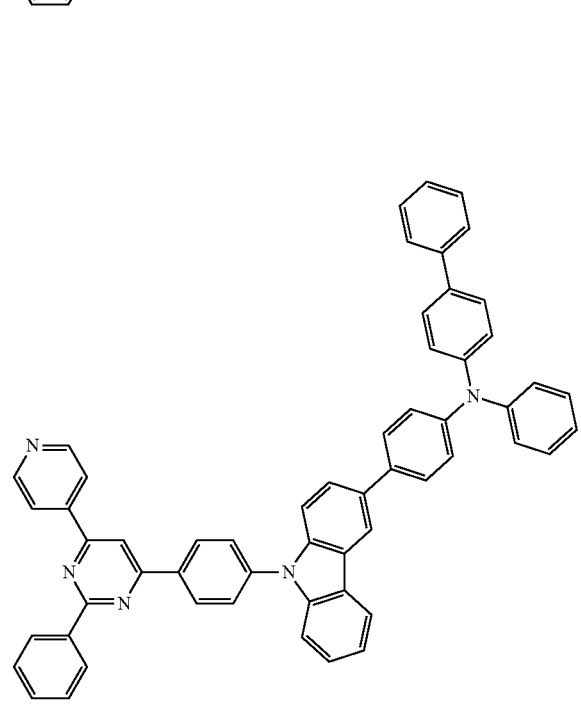
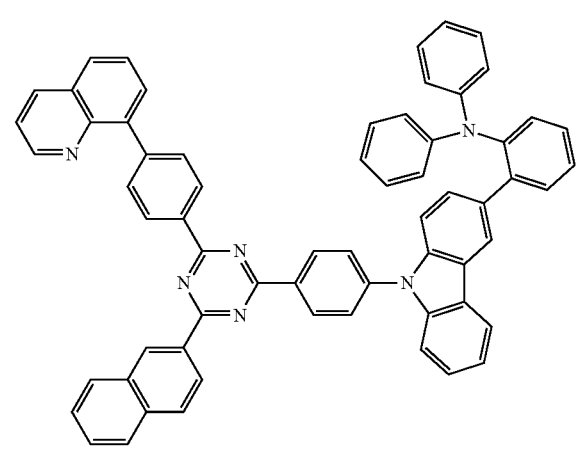
-continued
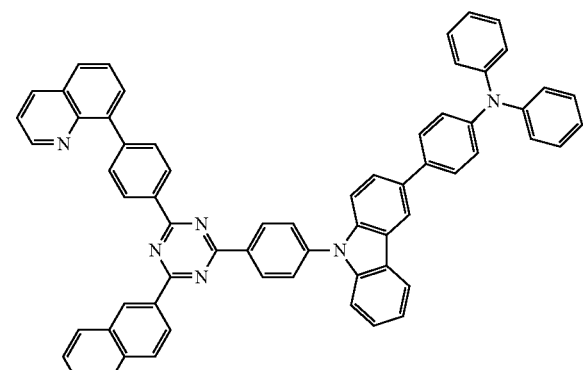
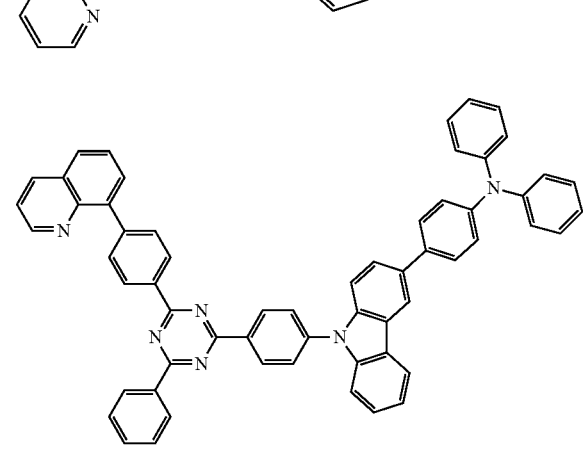
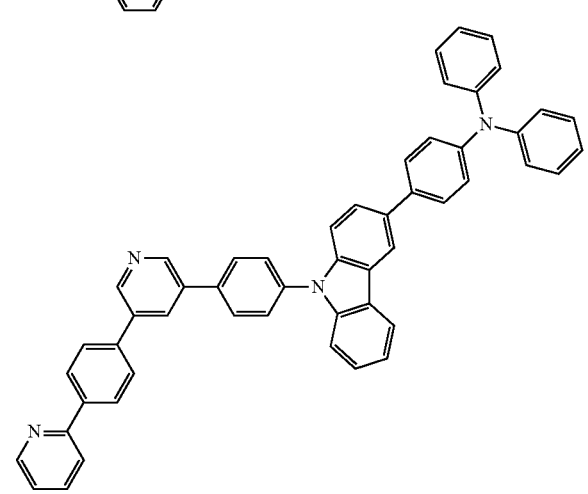

-continued

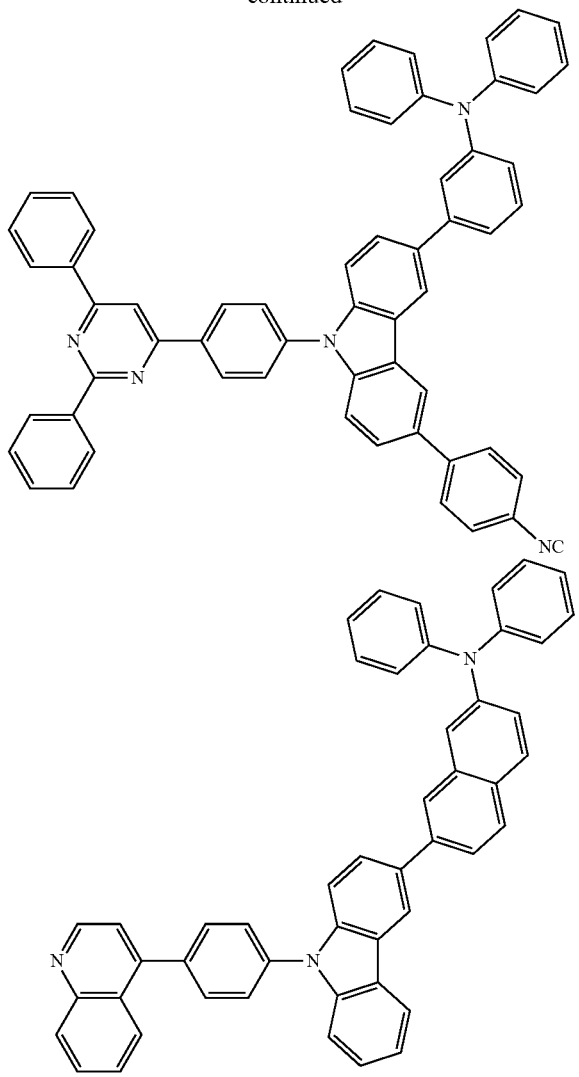

The aromatic amine derivative according to one embodiment of the invention can be used as a material for an organic electroluminescence (EL) device. For example, it can be used as a hole-transporting material, a phosphorescent host material or a carrier-transporting material.

An organic EL device as another embodiment of the invention comprises one or plural organic thin film layers including at least one emitting layer being disposed between a cathode and an anode, and at least one layer of the organic thin film layers comprises the above-mentioned aromatic amine derivative.

No specific restrictions are imposed on the device structure of the organic EL device according to one embodiment of the invention, as long as an anode, an emitting layer and a cathode are stacked in this order. The organic EL device may further comprise one or more organic layer(s) or inorganic layer(s).

The organic EL device according to one embodiment of the invention is preferably a phosphorescent emitting device having the above-mentioned aromatic amine derivative in the emitting layer.

In addition to the above-mentioned aromatic amine derivative, it is preferred that the emitting layer comprise a phosphorescent dopant (metal complex) mentioned later. It is further preferred that the emitting layer comprise an iridium complex.

The organic EL device according to one embodiment of the invention may have a configuration in which the organic thin film layer mentioned above includes a hole-transporting layer and/or a hole-injecting layer and the aromatic amine derivative is contained in at least one of the hole-transporting layer and the hole-injecting layer.

The hole-transporting layer and/or the hole-injecting layer may essentially consist of the aromatic amine derivative (i.e. comprise the aromatic amine derivative as main components) or may consist only of the aromatic amine derivative.

Further, the organic EL device according to one embodiment of the invention may have a configuration in which the organic thin film layer includes an electron-transporting zone and the aromatic amine derivative mentioned above is contained in the electron-transporting zone.

Layers constituting the electron-transporting zone may essentially consist of an aromatic amine derivative (i.e. comprise the aromatic amine derivative as main components) or may consist only of the aromatic amine derivative.

The electron-transporting zone mentioned above is a part that is sandwiched between the cathode and the emitting layer and includes, for example, an electron-transporting layer, an electron-injecting layer, a hole-barrier layer, a triplet barrier layer, or the like.

As the device configuration of the organic EL device, the following configurations can be given, for example. In such device configurations, the emitting layer may be a stacked body of plural emitting layers. Further, it is preferred that a hole-transporting zone be provided between the cathode and the emitting layer.

Here, the "emitting unit" means the minimum unit that includes one or more organic thin film layers, one of which organic thin film layers being an emitting layer, and is capable of emitting light by recombination of holes and electrons injected.

(1) Anode/Emitting Unit/Cathode

The emitting unit mentioned above may be a stacked type emitting unit having plural phosphorescent emitting layers or plural fluorescent emitting layers. In this case, between the emitting layers, a spacing layer may be provided in order to prevent diffusion of excitons generated in the phosphorescent emitting layer to the fluorescent emitting layer. Representative device configuration of the emitting unit are shown below.

(a) Hole-transporting layer/emitting layer (/electron-transporting layer)
(b) Hole-transporting layer/first phosphorescent emitting layer/second phosphorescent emitting layer (/electron-transporting layer)
(c) Hole-transporting layer/phosphorescent emitting layer/ spacing layer/fluorescent emitting layer (/electron-transporting layer)
(d) Hole-transporting layer/first phosphorescent emitting layer/second phosphorescent emitting layer/spacing layer/fluorescent emitting layer (/electron-transporting layer)
(e) Hole-transporting layer/first phosphorescent emitting layer/spacing layer/second phosphorescent emitting layer/spacing layer/fluorescent emitting layer (/electron-transporting layer)
(f) Hole-transporting layer/phosphorescent emitting layer/ spacing layer/first fluorescent emitting layer/second fluorescent emitting layer (/electron-transporting layer)

(g) Hole-transporting layer/electron-barrier layer/emitting layer (/electron-transporting layer)
(h) Hole-transporting layer/emitting layer/hole-barrier layer (/electron-transporting layer)
(i) Hole-transporting layer/fluorescent emitting layer/triplet barrier layer (/electron-transporting layer)

The phosphorescent emitting layer or the fluorescent emitting layer may be layers that emit different colors of light. Specifically, in the stacked emitting layer (d), a layer configuration of a hole-transporting layer/first phosphorescent emitting layer (red emission)/second phosphorescent emitting layer (green emission)/spacing layer/fluorescent emitting layer (blue emission)/electron-transporting layer, or other configurations can be mentioned.

Between each emitting layer and the hole-transporting layer or the spacing layer, an electron-barrier layer may appropriately be provided. Between each emitting layer and the electron-transporting layer, a hole-barrier layer may appropriately be provided. Due to the provision of an electron-barrier layer or the hole-barrier layer, electrons or holes may be confined within the emitting layer, whereby recombination possibility of carriers in the emitting layer can be improved, leading to prolongation in lifetime.

As the representative device configuration of a tandem organic EL device, the following device configuration can be mentioned.

(2) Anode/First Emitting Unit/Intermediate Layer/Second Emitting Unit/Cathode

As for the first emitting unit and the second emitting unit, the same emitting unit as that mentioned above can be selected, for example.

The intermediate layer is generally called as an intermediate electrode, an intermediate conductive layer, a carrier-generating layer, an electron-withdrawing layer, a connecting layer and an intermediate insulating layer, and, as for the materials, known material configurations that enable to serve to supply electrons to the first emitting unit and enable to supply holes to the second emitting unit can be used.

FIG. 1 shows a schematic configuration of one example of the organic EL device according to one embodiment of the invention. An organic EL device 1 comprises a substrate 2, an anode 3, a cathode 4, and an emitting unit 10 disposed between the anode 3 and the cathode 4. The emitting unit 10 comprises an emitting layer 5 that comprises at least one phosphorescent emitting layer that comprises a phosphorescent host material and a phosphorescent dopant. Between the emitting layer 5 and the anode 3, hole-injecting and transporting layer 6, or the like, and between the emitting layer 5 and the cathode 4, an electron-injecting and transporting layer 7, or the like, may be formed. Further, an electron-barrier layer may be provided on the side of the emitting layer 5 nearer to the anode 3 and a hole-barrier layer may be provided on the side of the emitting layer 5 nearer to the cathode 4. As a result, it is possible to confine electrons or holes in the emitting layer 5, whereby the possibility of generation of excitons in the emitting layer 5 can be enhanced.

In the specification, a host combined with a fluorescent dopant is referred to as a fluorescent host and a host combined with a phosphorescent dopant is referred to as a phosphorescent host. A fluorescent host and a phosphorescent host are not distinguished only by the molecular structure. That is, the phosphorescent host means a material that constitutes a phosphorescent emitting layer that contains a phosphorescent dopant, and does not mean a material that cannot be used as a material constituting a fluorescent emitting layer. The same can be applied to a fluorescent host.

(Substrate)

The organic EL device according to the invention is formed on a transparent substrate. The transparent substrate serves to support the organic EL device, and is preferably a smooth substrate having a transmittance of 50% or more for light rays within visible ranges of 400 nm to 700 nm. Specific examples thereof include glass plates and polymer plates. Examples of the glass plate include those obtained by using soda-lime glass, barium/strontium-containing glass, lead glass, aluminosilicate glass, borosilicate glass, barium borosilicate glass, or quartz as a material. Examples of the polymer plate include those obtained by using, as raw materials, polycarbonate, acrylic, polyethylene terephthalate, polyethersulfide, or polysulfone.

(Anode)

The anode of the organic EL device plays a role for injecting holes into the hole-transporting layer or the emitting layer. It is effective to use one having a work function of 4.5 eV or more as the anode. As specific examples of the anode material, indium tin oxide alloy (ITO), tin oxide (NESA), indium zinc oxide alloy, gold, silver, platinum, copper, and the like can be given. The anode can be formed by forming these electrode materials into a thin film by vapor deposition, sputtering or the like. In the case where emission from the emitting layer is outcoupled through the anode, the transmittance of the anode for the emission is preferably more than 10%. The sheet resistance of the anode is preferably several hundreds $\Omega/\square$ or less. The film thickness of the anode, which varies depending upon the material thereof, is usually from 10 nm to 1 μm, preferably from 10 nm to 200 nm.

(Cathode)

The cathode serves to inject electrons to the electron-injecting layer, the electron-transporting layer or the emitting layer and preferably is formed of a material having a small work function. Although no specific restrictions are imposed on the cathode material, as specific examples, indium, aluminum, magnesium, magnesium-indium alloys, magnesium-aluminum alloys, aluminum-lithium alloys, aluminum-scandium-lithium alloys, magnesium-silver alloys or the like can be used. As in the case of the anode, the cathode can be produced by forming a thin film by a method such as a deposition method and a sputtering method. In addition, according to need, emission may be outcoupled from the cathode side.

(Emitting Layer)

The emitting layer is an organic layer having an emitting function, and where a doping system is used, it comprises a host material and a dopant material. The host material has a function of accelerating recombination of electrons and holes and confining excitons within the emitting layer. The dopant material has a function of emitting efficiently excitons obtained by recombination.

In the case of a phosphorescent device, the host material mainly has a function of confining excitons generated by a dopant within the emitting layer.

Here, in the emitting layer, a double host (also referred to as a host/cohost) that adjusts the carrier balance in the emitting layer may be used by combining an electron-transporting host and a hole-transporting host or by other methods. It is preferred that the emitting layer comprise a first host material and a second host material and that first host material be the material for the organic EL device according to one embodiment of the invention.

Double dopant may be used in which two or more types of dopant materials having a high quantum yield are incorporated, and each dopant emits light. Specifically, by allowing a host, a red dopant and a green dopant to be co-deposited, the emitting layers are allowed to be the common emitting layer, whereby yellow emission is realized.

As for the emitting layer, by allowing it to be a stacked body in which plural emitting layers are stacked, electrons and holes are accumulated in the interface of the emitting layers, whereby the recombination region is concentrated in the interface of the emitting layers, thereby to improve the quantum efficiency.

Easiness in injection of holes to the emitting layer and easiness in injection of electrons to the emitting layer may differ. Further, the hole-transporting performance and the electron-transporting performance indicated by the mobility of holes and electrons in the emitting layer may differ from each other.

The emitting layer can be formed by a known method such as a deposition method, a spin coating method, a LB method (Langmuir Blodgett method) or the like, for example. The emitting layer can also be formed by forming a solution obtained by dissolving a binder such as a resin and material compounds in a solvent into a thin film by a spin coating method and the like.

The emitting layer is preferably a molecular deposited film. The "molecular deposited film" means a thin film formed by deposition of a raw material compound in a vapor phase or a film formed by solidification of a raw material compound in a solution state or a liquid phase state. Normally, this molecular deposited film differs from a thin film (molecular accumulated film) formed by a LB method in aggregation structure or high-order structure, or differ in function derived from such difference in structure.

The dopant material is selected from a known fluorescent dopant showing fluorescent emission or a known phosphorescent dopant showing phosphorescent emission.

The fluorescent dopant is selected from a fluoranthene derivative, a pyrene derivative, an aryl acetylene derivative, a fluorene derivative, a boron complex, a perylene derivative, an oxadiazole derivative, an anthracene derivative, a chrysene derivative or the like. A fluoranthene derivative, a pyrene derivative and a boron complex can preferably be given.

A phosphorescent dopant that forms the emitting layer is a compound that can emit light from triplet excited state. The phosphorescent dopant is not limited as long as it can emit from triplet excited state. The phosphorescent dopant is preferably an organic metal complex containing at least one metal selected from Ir, Pt, Os, Au, Cu, Re and Ru and a ligand. It is preferred that the ligand have an ortho-metalated bond. In respect of a high phosphorescent quantum yield and capability of improving external quantum yield of an emitting device, the phosphorescent dopant is preferably a compound having a metal atom selected from Ir, Os and Pt. Further preferable are a metal complex such as an iridium complex, an osmium complex and a platinum complex, with an ortho-metalated complex being more preferable. Among them, an iridium complex and a platinum complex are more preferable, and an ortho-metalated iridium complex is particularly preferable.

The content of the phosphorescent dopant in the emitting layer is not particularly restricted, and it may be appropriately selected depending on the purpose. For example, the content is preferably 0.1 to 70 mass %, with 1 to 30 mass % being more preferable. When the content of the phosphorescent compound is 0.1 mass % or more, sufficient emission can be obtained. By allowing the content to be 70 mass % or less, it is possible to suppress a phenomenon called concentration quenching.

Specific examples of the organic metal complex that is preferable as the phosphorescent dopant are shown below.

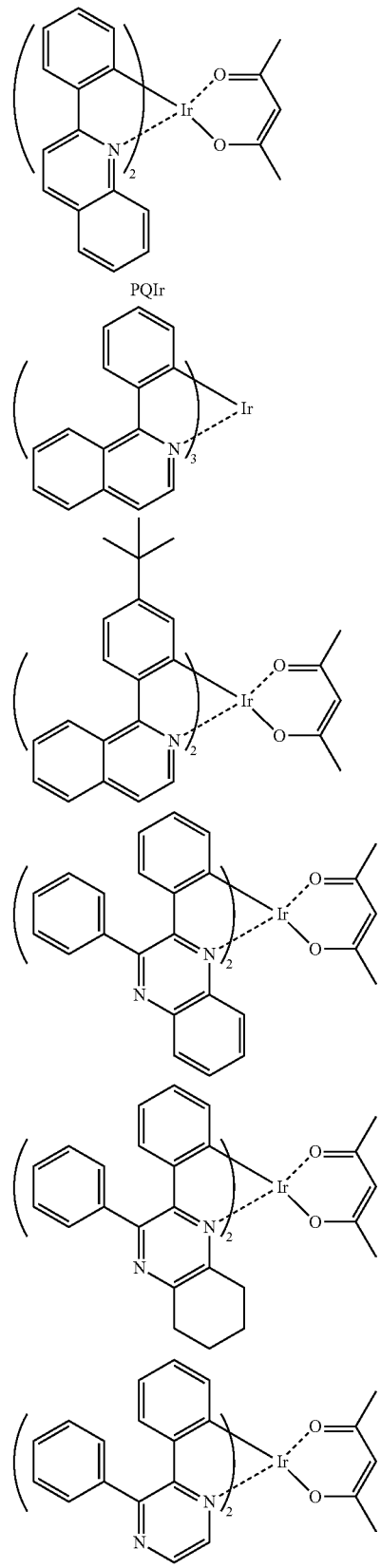

PQIr

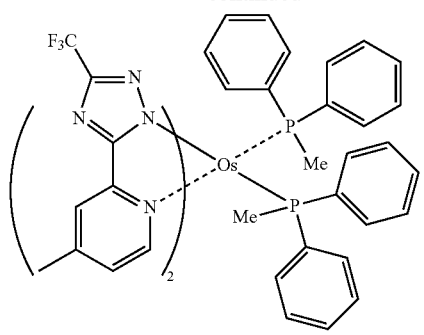
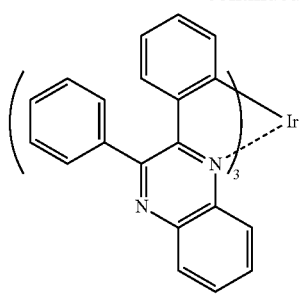
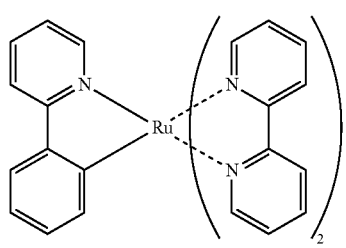
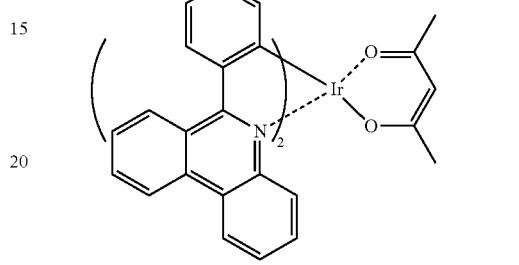
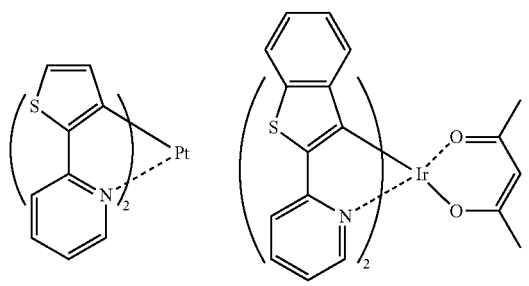
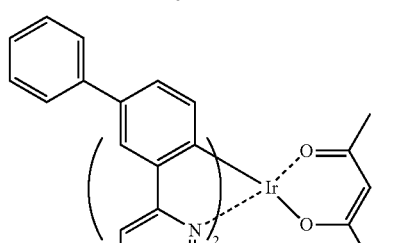
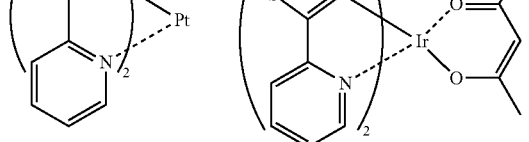
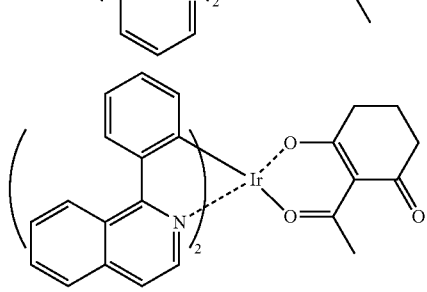
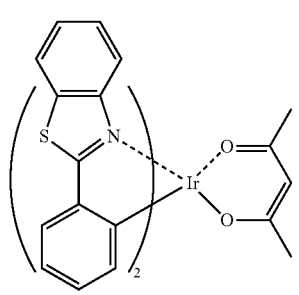
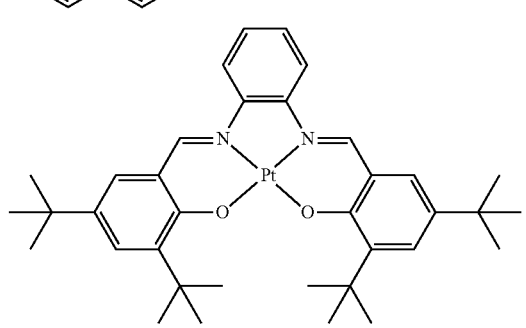
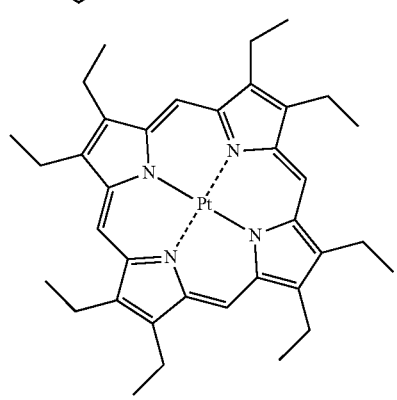
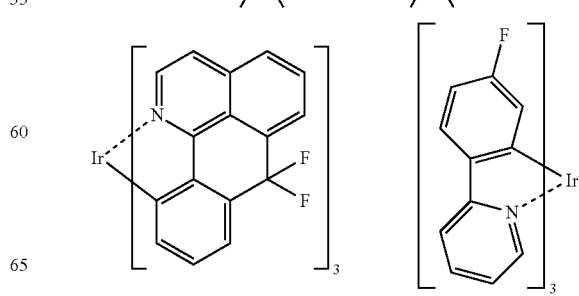

-continued
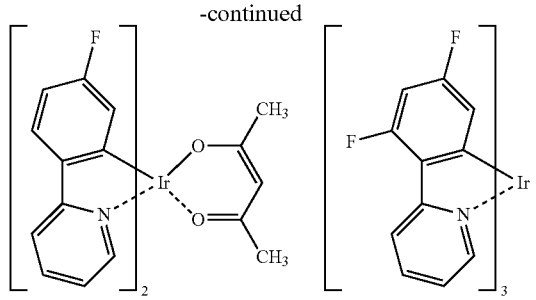
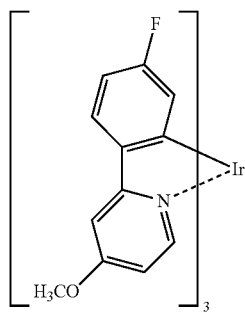
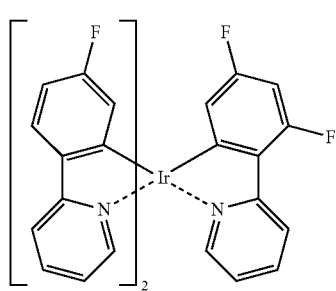
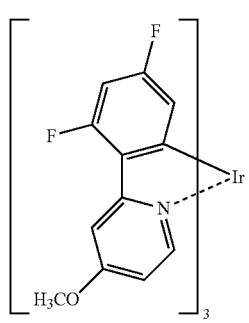
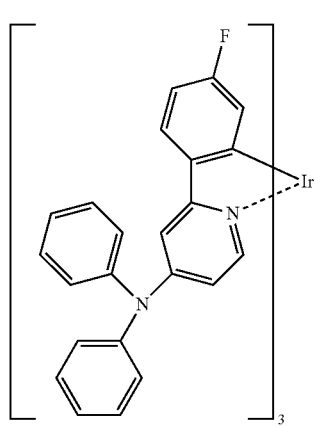
-continued
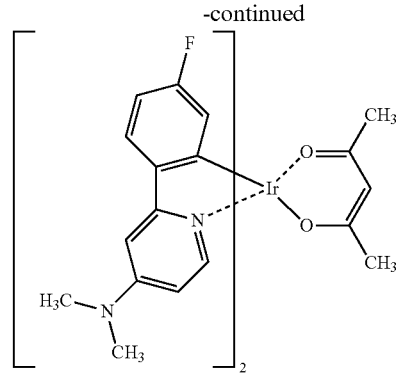
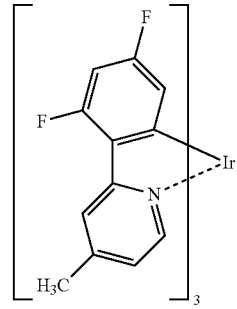
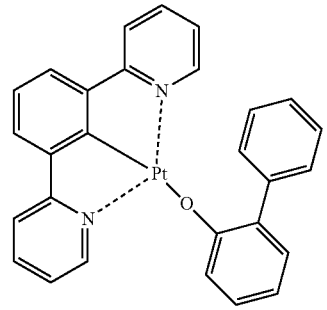
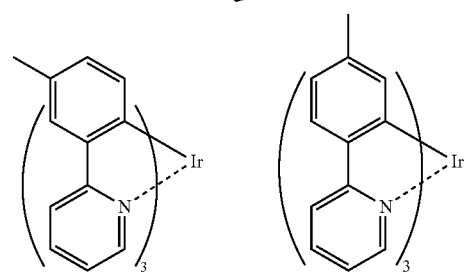
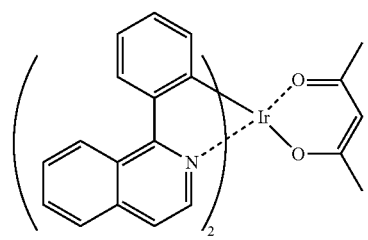
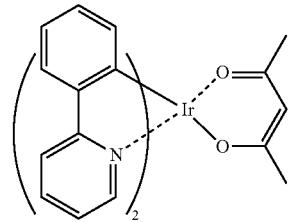

49
-continued
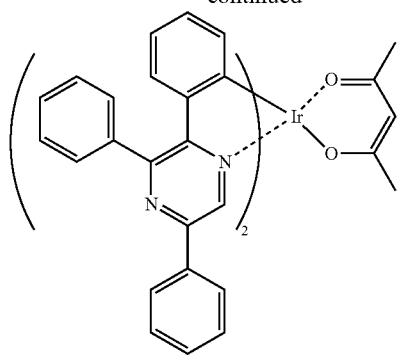
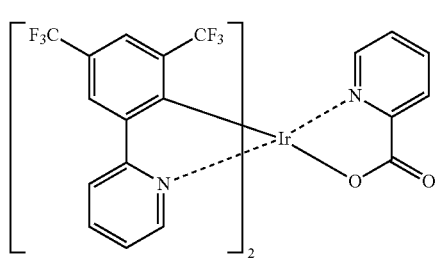
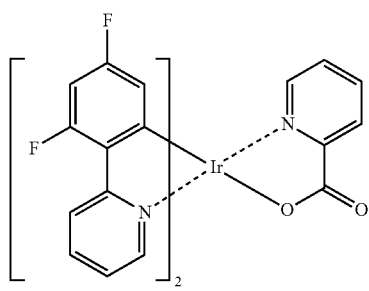
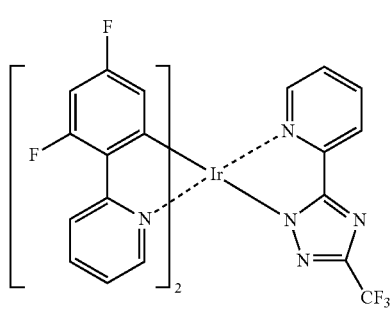
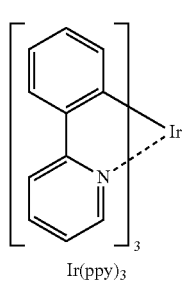
Ir(ppy)₃
50
-continued
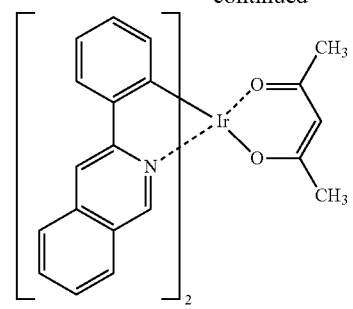
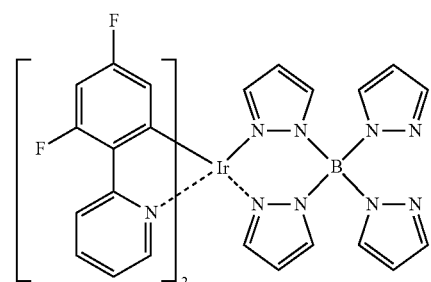
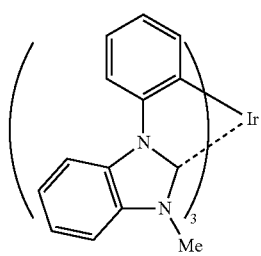
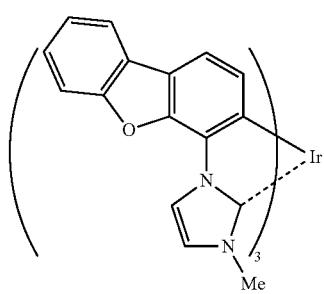
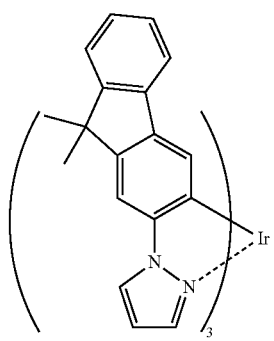

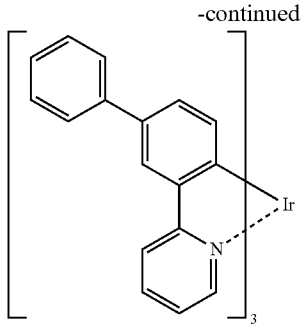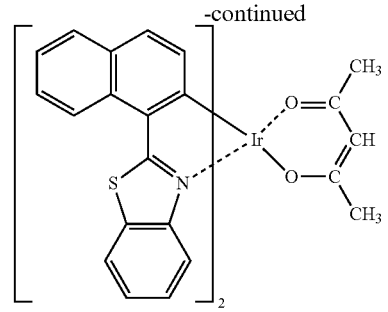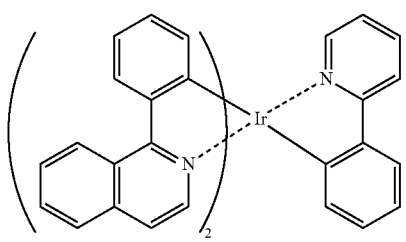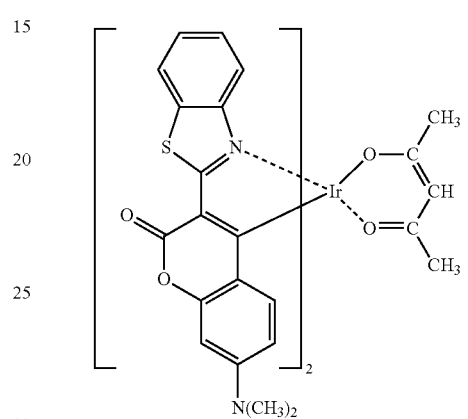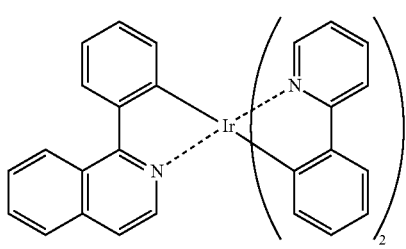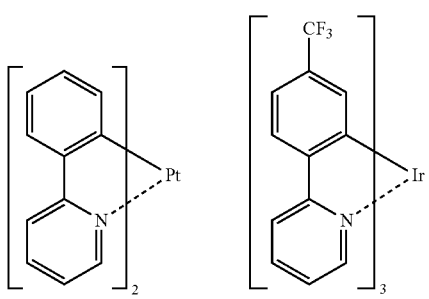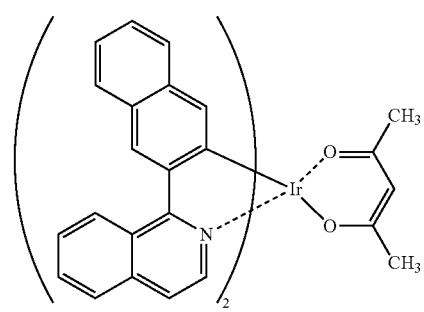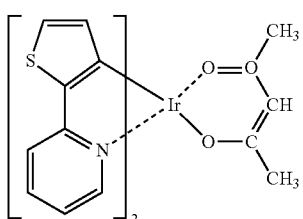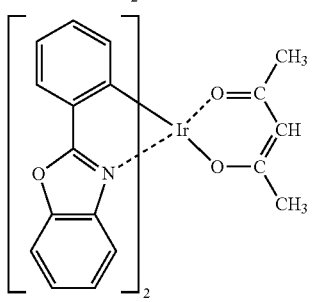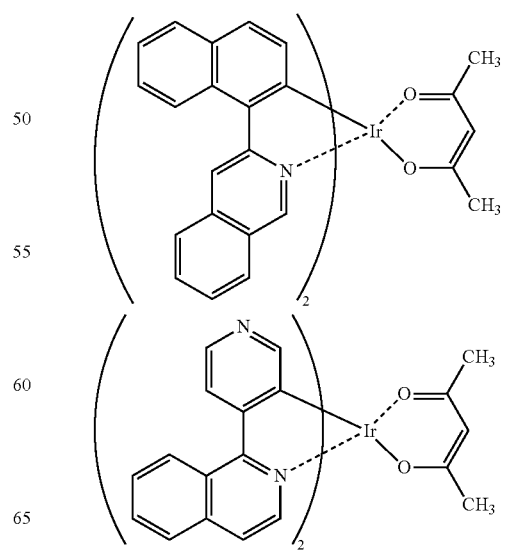

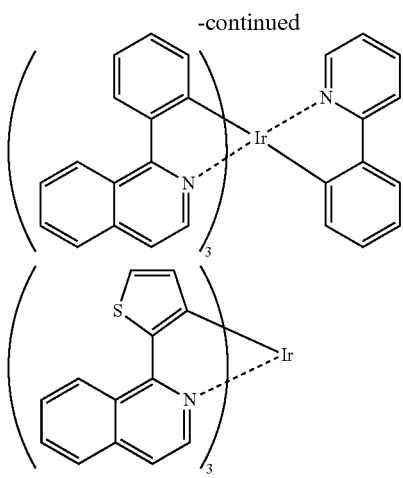

The phosphorescent host is a compound having a function of allowing a phosphorescent dopant to emit light efficiently by efficiently confining the triplet energy of the phosphorescent dopant in the emitting layer.

The material for an organic EL device according to one embodiment of the invention is preferable as the phosphorescent host. The emitting layer may preferably comprise one kind of the material for an organic EL device according to one embodiment of the invention or may preferably comprise two or more kinds of the material for an organic EL device according to one embodiment of the invention.

When the material for an organic EL device according to one embodiment of the invention is used as a host material of the emitting layer, the emission wavelength of the phosphorescent dopant contained in the emitting layer is not particularly restricted. It is preferred that at least one kind of the phosphorescent dopant materials contained in the emitting layer have a peak of an emission wavelength of 490 nm or more and 700 nm or less, more preferably 490 nm or more and 650 nm or less. As for the emission color of the emitting layer, red, yellow and green are preferable, for example. By using the compound according to one embodiment of the invention as the host material and by forming an emitting layer by doping the phosphorescent dopant having such an emission wavelength, it is possible to obtain a long-lived organic EL device.

In the organic EL device according to one embodiment of the invention, other compounds than the material for an organic EL device according to one embodiment of the invention can appropriately be selected as the phosphorescent host according to the above-mentioned purpose.

The material for an organic EL device according to one embodiment of the invention and other compounds may be used in combination as the phosphorescent host material in the same emitting layer. When plural emitting layers are present, as the phosphorescent host material for one of these emitting layers, the material for an organic EL device according to one embodiment of the invention is used, and as the phosphorescent host material for one of other emitting layers, other compounds than the material for an organic EL device according to one embodiment of the invention may be used. The material for an organic EL device according to one embodiment of the invention can be used in an organic layer other than the emitting layer. In that case, as the phosphorescent host of the emitting layer, other compounds than the material for an organic EL device according to one embodiment of the invention may be used.

As for the compound other than the material for an organic EL device according to one embodiment of the invention, as specific examples of the compound that is preferable as the phosphorescent host, a carbazole derivative, a triazole derivative, an oxazole derivative, an oxadiazole derivative, an imidazole derivative, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidene-based compounds, porphyrin-based compounds, anthraquinodimethane derivatives, anthrone derivatives, diphenylquinone derivatives, thiopyrandioxide derivatives, carbodiimide derivatives, fluorenylidene methane derivatives, distyrylpyrazine derivatives and heterocyclic tetracarboxylic anhydrides of naphthalene, perylene or the like, metal complexes of phthalocyanine derivatives and 8-quinolinol derivatives, various metal complex polysilane compounds represented by metal complexes having metal phthalocyanine, benzoxazole or benzothiazole as a ligand, poly (N-vinylcarbazole) derivatives; aniline-based copolymers, conductive high polymer oligomers such as thiophene oligomers and polythiophene, and polymer compounds such as polythiophene derivatives, polyphenylene derivatives, polyphenylene vinylene derivatives and polyfluorene derivatives can be given. The phosphorescent host may be used alone or in combination of two or more. As specific examples, the following compounds can be given.

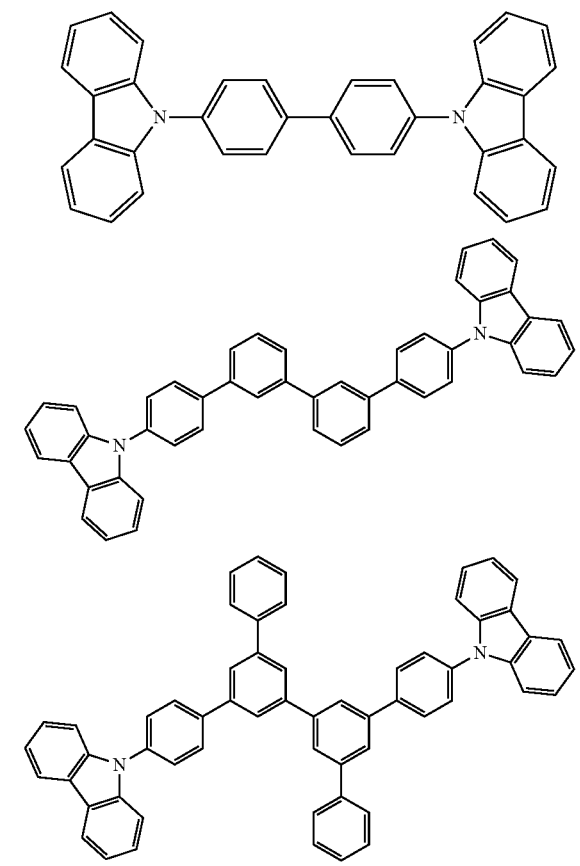

If the emitting layer comprises the first host material and the second host material, the material for an organic EL device according to one embodiment of the invention may be used as the first host material and other compounds than the material for an organic EL device according to one embodiment of the invention may be used as the second host material. The "first host material" and the "second host material" as referred to herein mean that the plural host materials contained in the emitting layer differ from each other in structure, and does not mean the content of the host material in the emitting layer.

The second host material is not particularly restricted, and compounds other than the material for an organic EL device according to one embodiment of the invention and the same compound mentioned above as being preferable as the phosphorescent host can be given. As the second host material, a compound having no cyano group is preferable. As the second host, a carbazole derivative, an arylamine derivative, a fluorenone derivative and an aromatic tertiary amine compound are preferable.

The thickness of the emitting layer is preferably 5 to 50 nm, more preferably 7 to 50 nm, and further preferably 10 to 50 nm. If the thickness is 5 nm or more, the formation of the emitting layer is facilitated. If the thickness is 50 nm or less, an increase in driving voltage can be avoided.

(Electron-Donating Dopant)

In the organic EL device according to one embodiment of the invention, it is preferred that an electron-donating dopant be contained in the interfacial region between the cathode and the emitting unit. Due to such a configuration, the organic EL device can have an increased luminance or a long life. Here, the electron-donating dopant means one having a metal with a work function of 3.8 eV or less. As specific examples thereof, at least one selected from an alkali metal, an alkali metal complex, an alkali metal compound, an alkaline earth metal, an alkaline earth metal complex, an alkaline earth metal compound, a rare earth metal, a rare each metal complex and a rare earth metal compound or the like can be mentioned.

As the alkali metal, Na (work function: 2.36 eV), K (work function: 2.28 eV), Rb (work function: 2.16 eV), Cs (work function: 1.95 eV) and the like can be given. One having a work function of 2.9 eV or less is particularly preferable. Among them, K, Rb and Cs are preferable. Rb or Cs is further preferable. Cs is most preferable. As the alkaline-earth metal, Ca (work function: 2.9 eV), Sr (work function: 2.0 eV to 2.5 eV), Ba (work function: 2.52 eV) and the like can be given. One having a work function of 2.9 eV or less is particularly preferable. As the rare-earth metal, Sc, Y, Ce, Tb, Yb and the like can be given. One having a work function of 2.9 eV or less is particularly preferable.

Examples of the alkali metal compound include an alkali oxide such as $Li_2O$, $Cs_2O$ or $K_2O$, and an alkali halide such as LiF, NaF, CsF and KF. Among them, LiF, $Li_2O$ and NaF are preferable. Examples of the alkaline-earth metal compound include BaO, SrO, CaO, and mixtures thereof such as $Ba_xSr_{1-x}O$ (0<x<1) and $Ba_xCa_{1-x}O$ (0<x<1). Among them, BaO, SrO and CaO are preferred. Examples of the rare-earth metal compound include $YbF_3$, $ScF_3$, $ScO_3$, $Y_2O_3$, $Ce_2O_3$, $GdF_3$ and $TbF_3$. Among these, $YbF_3$, $ScF_3$ and $TbF_3$ are preferable.

The alkali metal complexes, the alkaline-earth metal complexes and the rare earth metal complexes are not particularly limited as long as they contain, as a metal ion, at least one of alkali metal ions, alkaline-earth metal ions, and rare-earth metal ions. Meanwhile, preferred examples of the ligand include, but are not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfluborane, bipyridyl, phenanthroline, phthalocyanine, porphyrin, cyclopentadiene, β-diketones, azomethines, and derivatives thereof.

Regarding the addition form of the electron-donating dopant, it is preferred that the electron-donating dopant be formed in a shape of a layer or an island in the interfacial region. A preferred method for the formation is a method in which an organic substance (a light emitting material or an electron-injecting material) for forming the interfacial region is deposited simultaneously with deposition of the electron-donating dopant by a resistant heating deposition method, thereby dispersing the electron-donating dopant in the organic compound. The dispersion concentration of the organic compound:the electron-donating dopant (molar ratio) is 100:1 to 1:100, preferably 5:1 to 1:5.

In a case where the electron-donating dopant is formed into the shape of a layer, the light-emitting material or electron-injecting material which serves as an organic layer in the interface is formed into the shape of a layer. After that, the reductive dopant is solely deposited by the resistant heating deposition method to form a layer preferably having a thickness of 0.1 nm or more and 15 nm or less. In a case where the electron-donating dopant is formed into the shape of an island, the emitting material or the electron-injecting material which serves as an organic layer in the interface is formed into the shape of an island. After that, the electron-donating dopant is solely deposited by the resistant heating deposition method to form an island preferably having a thickness of 0.05 nm or more and 1 nm or less.

The ratio of the main component and the electron-donating dopant in the organic EL device according to one embodiment of the invention is main component electron-donating dopant=5:1 to 1:5 in terms of molar ratio, more preferably 2:1 to 1:2.

(Electron-Transporting Layer)

The electron-transporting layer is an organic layer that is formed between the emitting layer and the cathode and has a function of transporting electrons from the cathode to the emitting layer. When the electron-transporting layer is formed of plural layers, an organic layer that is nearer to the cathode is often defined as the electron-injecting layer. The electron-injecting layer has a function of injection electrons from the cathode efficiently to the organic layer unit.

As the electron-transporting material used in the electron-transporting layer, an aromatic heterocyclic compound having one or more hetero atoms in the molecule may preferably be used. In particular, a nitrogen-containing derivative is preferable. As the nitrogen-containing ring derivative, an aromatic ring having a nitrogen-containing six-membered or five-membered ring skeleton or a fused aromatic ring compound having a nitrogen-containing six-membered or five-membered ring skeleton is preferable.

As the nitrogen-containing ring derivative, a nitrogen-containing ring metal chelate complex represented by the following formula (A) is preferable, for example.

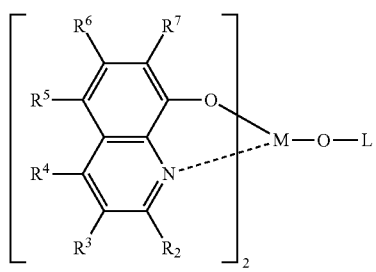

(A)

$R^2$ to $R^7$ in the formula (A), that is a nitrogen-containing ring metal chelate complex are independently a hydrogen atom, a heavy hydrogen atom, a hydrogen atom, a hydroxyl group, an amino group, a hydrocarbon group including 1 to 40 carbon atoms, an alkoxy group including 1 to 40 carbon atoms, an aryloxy group including 6 to 50 carbon atoms, an alkoxycarbonyl group or an aromatic heterocyclic group including 5 to 50 ring carbon atoms. They may be substituted.

As the halogen atom, fluorine, chlorine, bromine, iodine or the like can be given, for example.

As examples of the amino group that may be substituted, an alkylamino group, an arylamino group and an aralkylamino group can be given.

The alkylamino group and the aralkylamino group are represented by $-NQ^1Q^2$. $Q^1$ and $Q^2$ are independently an alkyl group including 1 to 20 carbon atoms or an aralkyl group including 1 to 20 carbon atoms. One of $Q^1$ and $Q^2$ may be a hydrogen atom or a heavy hydrogen atom.

The arylamino group is represented by $-NAr^1Ar^2$, and $Ar^1$ and $Ar^2$ are independently a non-fused aromatic hydrocarbon group or fused aromatic hydrocarbon group including 6 to 50 carbon atoms. One of $Ar^1$ and $Ar^2$ may be either a hydrogen atom or a heavy hydrogen atom.

The hydrocarbon group including 1 to 40 carbon atoms includes an alkyl group, an alkenyl group, a cycloalkyl group, an aryl group and an aralkyl group.

The alkoxycarbonyl group is represented by $-COOY'$ and Y' is an alkyl group including 1 to 20 carbon atoms.

M is aluminum (Al), gallium (Ga) or indium (In), and M is preferably In.

L is a group represented by the following formula (A') or (A").

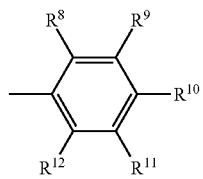

(A')

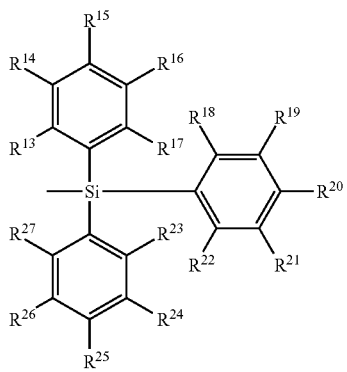

(A")

In the formula (A'), $R^8$ to $R^{12}$ are independently a hydrogen atom, a heavy hydrogen atom or a substituted or unsubstituted hydrocarbon group including 1 to 40 carbon atoms, and adjacent groups may form a ring structure. In the formula (A"), $R^{13}$ to $R^{27}$ are independently a hydrogen atom, a heavy hydrogen atom or a substituted or unsubstituted hydrocarbon group including 1 to 40 carbon atoms, and adjacent groups may form a ring structure.

The hydrocarbon group including 1 to 40 carbon atoms represented by $R^8$ to $R^{12}$ and $R^{13}$ to $R^{27}$ in the formulas (A') and (A") is the same as the hydrocarbon group represented by $R^2$ to $R^7$ in the formula (A) that is a nitrogen-containing ring metal chelate complex. As the divalent group formed when the adjacent groups of $R^8$ to $R^{12}$ and $R^{13}$ to $R^{27}$ form a ring structure, a tetramethylene group, a pentamethylene group, a hexamethylene group, a diphenylmethane-2,2'-diyl group, a diphenylethane-3,3'-diyl group, a diphenylpropane-4,4'-diyl group or the like can be mentioned.

As the electron-transmitting material used in the electron-transmitting layer, a metal complex of 8-hydroxyquinoline or a derivative thereof, an oxadiazole derivative and a nitrogen-containing heterocyclic derivative are preferable. Specific examples of the metal complex of the 8-hydroxyquinoline or the derivative thereof include metal chelate oxynoid compounds containing a chelate of oxine (generally, 8-quinolinol or 8-hydroxyquinoline). For example, tris(8-quinolinol)aluminum can be used. As the oxadiazole derivative, the following can be given, for example.

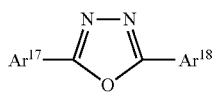

$Ar^{20}$, $Ar^{23}$ and $Ar^{24}$ are independently a substituted or unsubstituted divalent aromatic hydrocarbon group or fused aromatic hydrocarbon group including 6 to 50 carbon atoms, and $Ar^{23}$ and $Ar^{24}$ may be the same as or different from each other. As the divalent aromatic hydrocarbon group or the fused aromatic hydrocarbon group, a phenylene group, a naphthylene group, a biphenylene group, an anthranylene group, a perylenylene group, a pyrenylene group or the like can be given. As the substituent of these, an alkyl group including 1 to 10 carbon atoms, an alkoxy group including 1 to 10 carbon atoms, a cyano group or the like can be given.

As these electron-transmitting compounds, those having excellent thin film-forming capability can be preferably used. As specific examples of these electron-transmitting compounds, the following can be given.

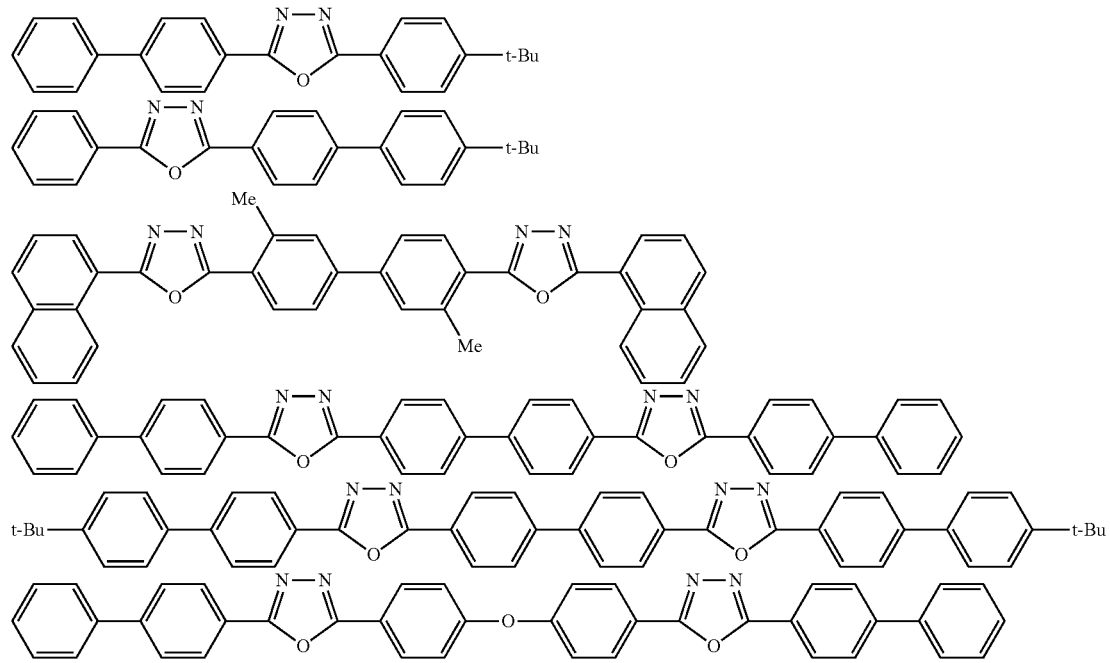

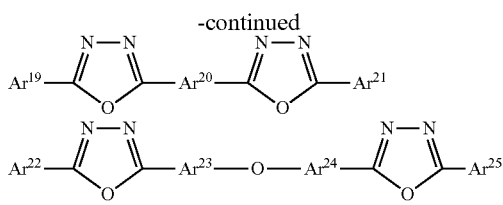

In the formula, $Ar^{17}$, $Ar^{18}$, $Ar^{19}$, $Ar^{21}$, $Ar^{22}$ and $Ar^{25}$ are independently a substituted or unsubstituted aromatic hydrocarbon group or fused aromatic hydrocarbon group including 6 to 50 carbon atoms. $Ar^{17}$ and $Ar^{18}$, $Ar^{19}$ and $Ar^{21}$ and $Ar^{22}$ and $Ar^{25}$ may be the same as or different from each other. As the aromatic hydrocarbon group or the fused aromatic hydrocarbon group, a phenyl group, a naphthyl group, a biphenyl group, an anthranyl group, a peryleny group, a pyrenyl group or the like can be mentioned. As the substituent of these groups, an alkyl group including 1 to 10 carbon atoms, an alkoxy group including 1 to 10 carbon atoms, a cyano group or the like can be given.

The nitrogen-containing heterocyclic derivative as the electron-transmitting compound is a nitrogen-containing heterocyclic derivative that comprises an organic compound represented by the following formula and is not a metal complex can be given. For example, a five-membered ring or a six-membered ring having a skeleton represented by the following formula (B) or one having a structure represented by the following formula (C) can be mentioned.

 (B)

 (C)

In the formula (C), X is a carbon atom or a nitrogen atom. $Z_1$ and $Z_2$ are independently a group of atoms capable of forming a nitrogen-containing heterocyclic ring.

The nitrogen-containing heterocyclic ring derivative is further preferably an organic compound having a nitrogen-containing aromatic polycyclic ring group composed of a five-membered ring or a six-membered ring. Further, in the case of the nitrogen-containing aromatic polycyclic ring group, a nitrogen-containing polycyclic organic compound having a skeleton obtained by combining the above formulas (B) and (C) or the above formula (B) and the following formula (D) is preferable.

The nitrogen-containing group in the nitrogen-containing aromatic polycyclic organic compound can be selected from the nitrogen-containing heterocyclic groups represented by the following formulas, for example.

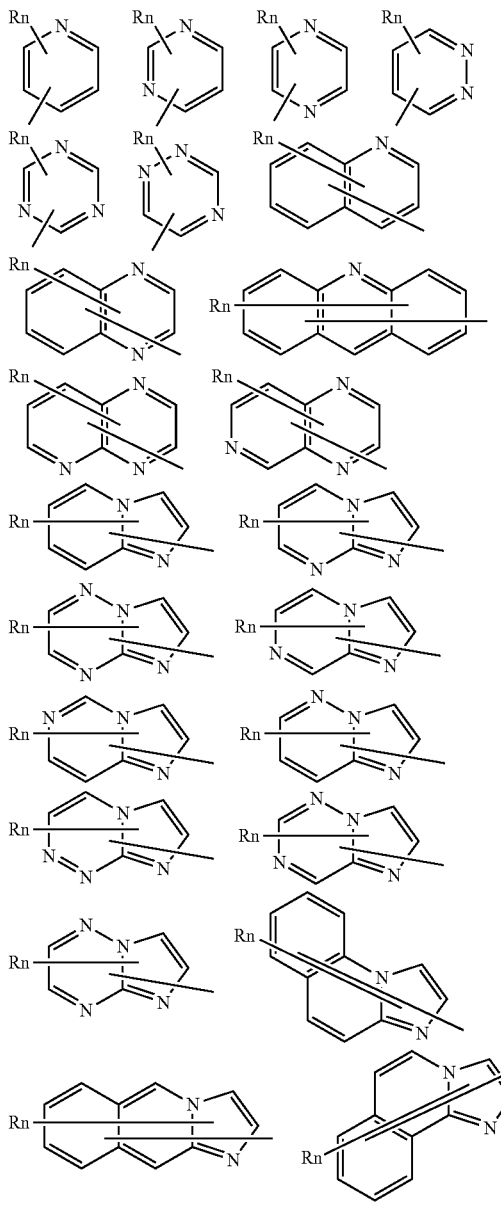

In each of the above formulas, R is an aromatic hydrocarbon group or fused aromatic hydrocarbon group including 6 to 40 carbon atoms, an aromatic heterocyclic group or fused aromatic heterocyclic group including 3 to 40 carbon atoms, an alkyl group including 1 to 20 carbon atoms or an alkoxy group including 1 to 20 carbon atoms. n is an integer of 0 to 5, and when n is an integer of 2 or more, plural Rs may be the same or different.

As further preferable specific compounds, a nitrogen-containing heterocyclic derivative represented by the following formula (D1) can be mentioned.

In the formula (D1), HAr is a substituted or unsubstituted nitrogen-containing heterocyclic ring group including 3 to 40 carbon atoms, $L^1$ is a single bond, a substituted or unsubstituted aromatic hydrocarbon group or fused aromatic hydrocarbon group including 6 to 40 carbon atoms or a substituted or unsubstituted aromatic heterocyclic group or fused aromatic heterocyclic group including 3 to 40 carbon atoms, $Ar^1$ is a substituted or unsubstituted divalent aromatic hydrocarbon group including 6 to 40 carbon atoms, and $Ar^2$ is a substituted or unsubstituted aromatic hydrocarbon group or fused aromatic hydrocarbon group including 6 to 40 carbon atoms or a substituted or unsubstituted aromatic heterocyclic group or fused aromatic heterocyclic group including 3 to 40 carbon atoms.

HAr is selected from the following group, for example.

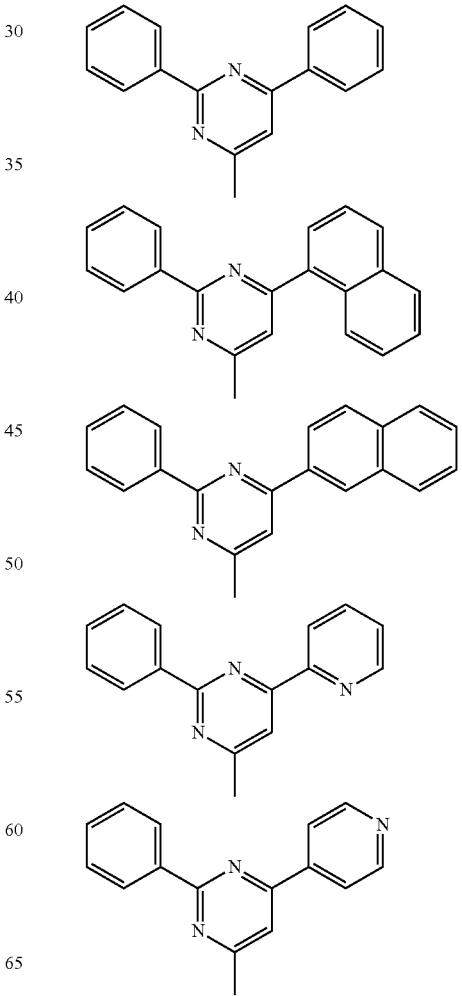

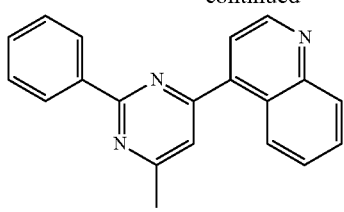
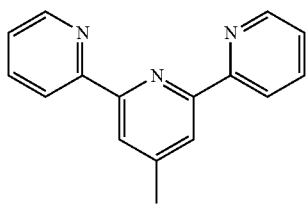
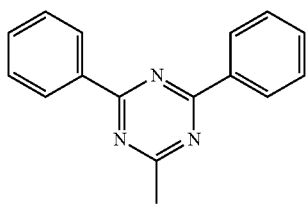
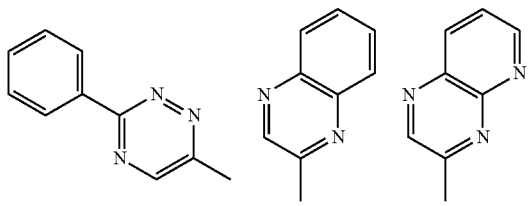
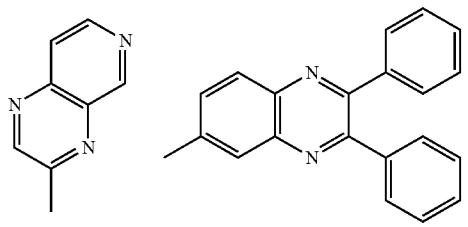
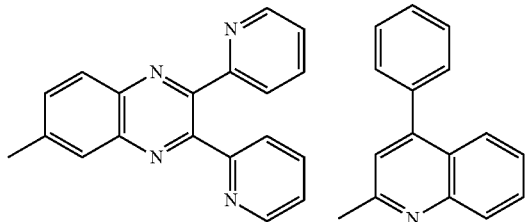
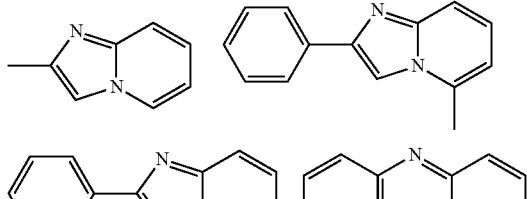
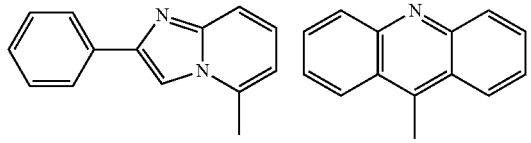

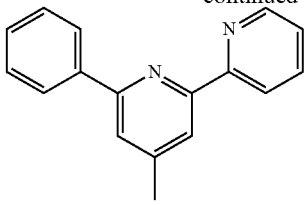

$L^1$ in the above formula (D1) is selected from the following group, for example.

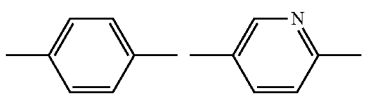

$Ar^1$ in the formula (D1) is selected from the arylanthranyl group in the following formulas (D2) and (D3).

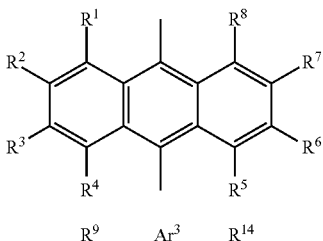
(D2)

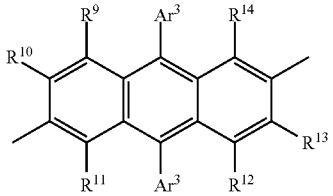
(D3)

In the formulas (D2) and (D3), $R^1$ to $R^{14}$ are independently a hydrogen atom, a heavy hydrogen atom, a halogen atom, an alkyl group including 1 to 20 carbon atoms, an alkoxy group including 1 to 20 carbon atoms, an aryloxy group including 6 to 40 carbon atoms, a substituted or unsubstituted aromatic hydrocarbon group or fused aromatic hydrocarbon group including 6 to 40 carbon atoms or a substituted or unsubstituted aromatic heterocyclic group or fused aromatic heterocyclic group including 3 to 40 carbon atoms; $Ar^a$ is a substituted or unsubstituted aromatic hydrocarbon group or fused aromatic hydrocarbon group including 6 to 40 carbon atoms or a substituted or unsubstituted aromatic heterocyclic group or fused aromatic heterocyclic group including 3 to 40 carbon atoms. The nitrogen-containing heterocyclic derivative may be one in which any of $R^1$ to $R^8$ are a hydrogen atom or a heavy hydrogen atom.

$Ar^2$ in the formula (D1) is selected from the following group, for example.

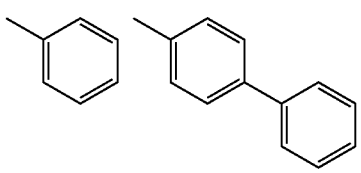

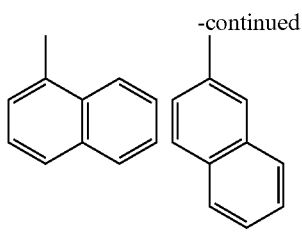

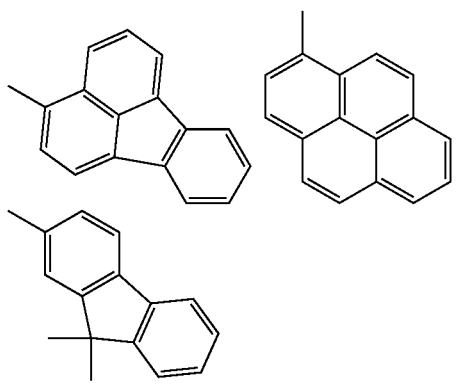

As the nitrogen-containing aromatic polycyclic organic compound as the electron-transmitting compound, in addition to those mentioned above, the following compounds can preferably be used.

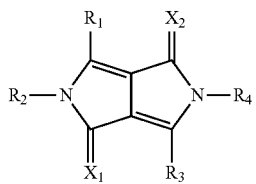
(D4)

In the formula (D4), $R_1$ to $R_4$ are independently a hydrogen atom, a heavy hydrogen atom, a substituted or unsubstituted aliphatic group including 1 to 20 carbon atoms, a substituted or unsubstituted alicyclic group including 3 to 20 carbon atoms, a substituted or unsubstituted aromatic ring group including 6 to 50 carbon atoms or a substituted or unsubstituted heterocyclic group including 3 to 50 carbon atoms; and $X_1$ and $X_2$ are independently an oxygen atom, a sulfur atom or a dicyanomethylene group.

As the electron-transmitting compound, the following compound is preferably used.

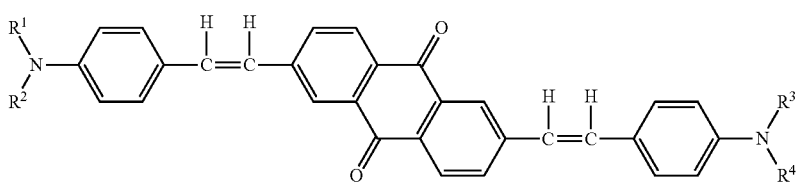
(D5)

In the formula (D5), $R^1$, $R^2$, $R^3$ and $R^4$ are groups that are the same as or different from each other, and is an aromatic hydrocarbon group or a fused aromatic hydrocarbon group represented by the following formula (D6).

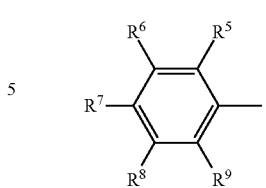
(D6)

In the formula (D6), $R^5$, $R^6$, $R^7$, $R^8$ and $R^9$ are groups that are the same as or different from each other, and is a hydrogen atom, a heavy hydrogen atom, a saturated or unsaturated alkoxyl group including 1 to 20 carbon atoms, a saturated or unsaturated alkyl group including 1 to 20 carbon atoms, an amino group or an alkylamino group including 1 to 20 carbon atoms. At least one of $R^5$, $R^6$, $R^7$, $R^8$ and $R^9$ is a group other than a hydrogen atom or a heavy hydrogen atom.

Further, the electron-transmitting compound may be a high molecular compound that comprises the nitrogen-containing heterocyclic group or the nitrogen-containing heterocyclic derivative.

It is particularly preferred that the electron-transporting layer of the organic EL device according to one embodiment of the invention contain at least one of the nitrogen-containing heterocyclic derivatives represented by the following formulas (E) to (G):

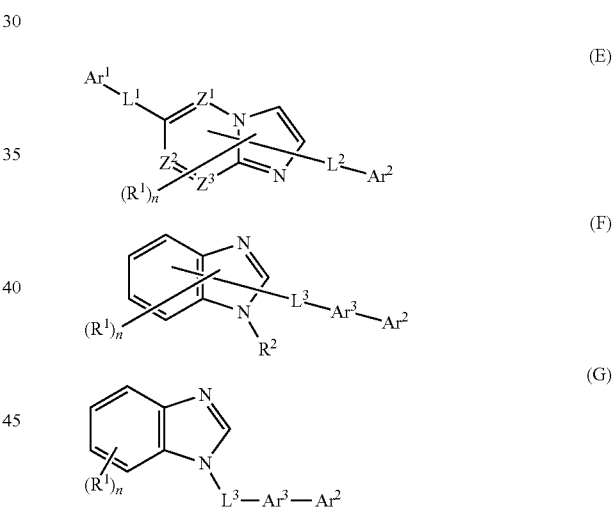

In the formulas (E) to (G), $Z^1$, $Z^2$ and $Z^3$ are independently a nitrogen atom or a carbon atom.

$R^1$ and $R^2$ are independently a substituted or unsubstituted aryl group including 6 to 50 ring carbon atoms, a substituted or unsubstituted heteroaryl group including 5 to 50 ring atoms, a substituted or unsubstituted alkyl group including 1 to 20 carbon atoms, a substituted or unsubstituted haloalkyl group including 1 to 20 carbon atoms or a substituted or unsubstituted alkoxy group including 1 to 20 carbon atoms.

n is an integer of 0 to 5. When n is an integer of 2 or more, plural $R^1$s may be the same or different. The two adjacent $R^1$s may be bonded to each other to form a substituted or unsubstituted hydrocarbon ring.

$Ar^1$ is a substituted or unsubstituted aryl group including 6 to 50 ring carbon atoms or a substituted or unsubstituted heteroaryl group including 5 to 50 ring atoms.

$Ar^2$ is a hydrogen atom, a substituted or unsubstituted alkyl group including 1 to 20 carbon atoms, a substituted or unsubstituted haloalkyl group including 1 to 20 carbon atoms, a substituted or unsubstituted alkoxy group including 1 to 20 carbon atoms, a substituted or unsubstituted aryl group including 6 to 50 ring carbon atoms or a substituted or unsubstituted heteroaryl group including 5 to 50 ring atoms.

Any one of $Ar^1$ and $Ar^2$ is a substituted or unsubstituted fused aromatic hydrocarbon ring group including 10 to 50 ring carbon atoms or a substituted or unsubstituted fused aromatic heterocyclic ring group including 9 to 50 ring atoms.

$Ar^3$ is a substituted or unsubstituted arylene group including 6 to 50 ring carbon atoms or a substituted or unsubstituted heteroarylene group including 5 to 50 ring atoms.

$L^1$, $L^2$ and $L^3$ are independently a single bond, a substituted or unsubstituted arylene group including 6 to 50 ring carbon atoms or a substituted or unsubstituted divalent fused aromatic heterocyclic ring group including 9 to 50 ring atoms.

As the aryl group including 6 to 50 ring carbon atoms, a phenyl group, a naphthyl group, an anthryl group, a phenanthryl group, a naphthacenyl group, a chrysenyl group, a pyrenyl group, a biphenyl group, a terphenyl group, a tolyl group, a fluoranthenyl group and a fluorenyl group can be mentioned.

As the heteroaryl group including 5 to 50 ring atoms, a pyrrolyl group, a furyl group, a thienyl group, a silolyl group, a pyridyl group, a quinolyl group, an isoquinolyl group, a benzofuryl group, an imidazolyl group, a pyrimidyl group, a carbazolyl group, a selenophenyl group, an oxadiazolyl group, a triazolyl group, a pyrazinyl group, a pyridazinyl group, a triazinyl group, a quinoxalinyl group, an acridinyl group, an imidazo[1,2-a]pyridinyl group, an imidazo[1,2-a]pyrimidinyl group or the like can be given.

As the alkyl group including 1 to 20 carbon atoms, a methyl group, an ethyl group, a propyl group, a butyl group, a pentyl group, a hexyl group or the like can be given.

As the haloalkyl group including 1 to 20 carbon atoms, a group obtained by substituting one or two or more hydrogen atoms in the alkyl group with at least one halogen atom selected from fluorine, chlorine, iodine and bromine.

As the alkoxy group including 1 to 20 carbon atoms, a group having the alkyl group as an alkyl part can be given.

As the arylene group including 6 to 50 ring carbon atoms, a group obtained by removing one hydrogen atom from the aryl group can be given.

As the divalent fused aromatic heterocyclic ring group including 9 to 50 ring atoms, a group obtained by removing one hydrogen atom from the fused aromatic heterocyclic ring group mentioned above as the heteroaryl group can be given.

The film thickness of the electron-transporting layer is not particularly restricted, but is preferably 1 nm to 100 nm.

As the constituting elements of the electron-injecting layer that can be provided in adjacent to the electron-transporting layer, in addition to the nitrogen-containing ring derivative, as an inorganic compound, it is preferable to use an insulator or a semiconductor. If the electron-insulating layer is formed of an insulator or a semiconductor, current leakage can be effectively prevented, whereby electron-injecting properties can be improved.

As such an insulator, it is preferable to use at least one metal compound selected from the group consisting of an alkali metal chalcogenide, an alkaline earth metal chalcogenide, a halide of an alkali metal and a halide of an alkaline earth metal. It is preferred that the electron-injecting layer be formed of these alkali metal chalcogenides or the like, since the electron-injecting property can be further improved. Specifically, as preferable alkali metal chalcogenides, $Li_2O$, $K_2O$, $Na_2S$, $Na_2Se$ and $Na_2O$ can be given. As preferable alkaline earth metal chalcogenides, CaO, BaO, SrO, BeO, BaS and CaSe can be given, for example. As preferable halides of an alkali metal, LiF, NaF, KF, LiCl, KCl, NaCl or the like can be given, for example. As preferable halides of an alkaline earth metal, a fluoride such as $CaF_2$, $BaF_2$, $SrF_2$, $MgF_2$ and $BeF_2$ and a halide other than a fluoride can be given, for example.

As the semiconductor constituting the electron-injecting layer, an oxide, a nitride or a nitric oxide containing at least one element selected from Ba, Ca, Sr, Yb, Al, Ga, In, Li, Na, Cd, Mg, Si, Ta, Sb and Zn, or the like can be given, for example. They can be used singly or in combination of two or more. Further, it is preferred that an inorganic compound constituting the electron-injecting layer be a finely-crystallized or amorphous insulating thin film. If the electron-injecting layer is formed of these insulting thin films, more homogenous thin film is formed, and hence, pixel defects such as dark spots can be decreased. As such an inorganic compound, alkali metal chalcogenide, alkaline earth metal chalcogenide, a halide of an alkali metal and a halide of an alkaline earth metal or the like can be given, for example.

If such an insulator or a semiconductor is used, the preferable thickness of the layer is about 0.1 nm to 15 nm. The electron-injecting layer in the invention may comprise the above-mentioned electron-donating dopant.

(Hole-Transporting Layer)

The hole-transporting layer is an organic layer that is formed between the emitting layer and the anode, and has a function of transporting holes from the anode to the emitting layer. If the hole-transporting layer is formed of plural layers, an organic layer that is nearer to the anode may often be defined as the hole-injecting layer. The hole-injecting layer has a function of injecting holes efficiently to the organic layer unit from the anode.

As other materials that form the hole-transporting layer, an aromatic amine compound, for example, an aromatic amine derivative represented by the following formula (H) can preferably be used.

(H)

In the formula (H), $Ar^1$ to $Ar^4$ are a substituted or unsubstituted aromatic hydrocarbon group or fused aromatic hydrocarbon group including 6 to 50 ring carbon atoms, a substituted or unsubstituted aromatic heterocyclic group or fused aromatic heterocyclic group including 5 to 50 ring atoms, or a group formed by bonding of these aromatic hydrocarbon group or the fused aromatic hydrocarbon group and an aromatic heterocyclic group or a fused aromatic heterocyclic group.

In the formula (H), L is a substituted or unsubstituted aromatic hydrocarbon group or fused aromatic hydrocarbon group including 6 to 50 ring carbon atoms or a substituted or unsubstituted aromatic heterocyclic group or fused aromatic heterocyclic group including 5 to 50 ring atoms.

Specific examples of the compound represented by the formula (H) are shown below.

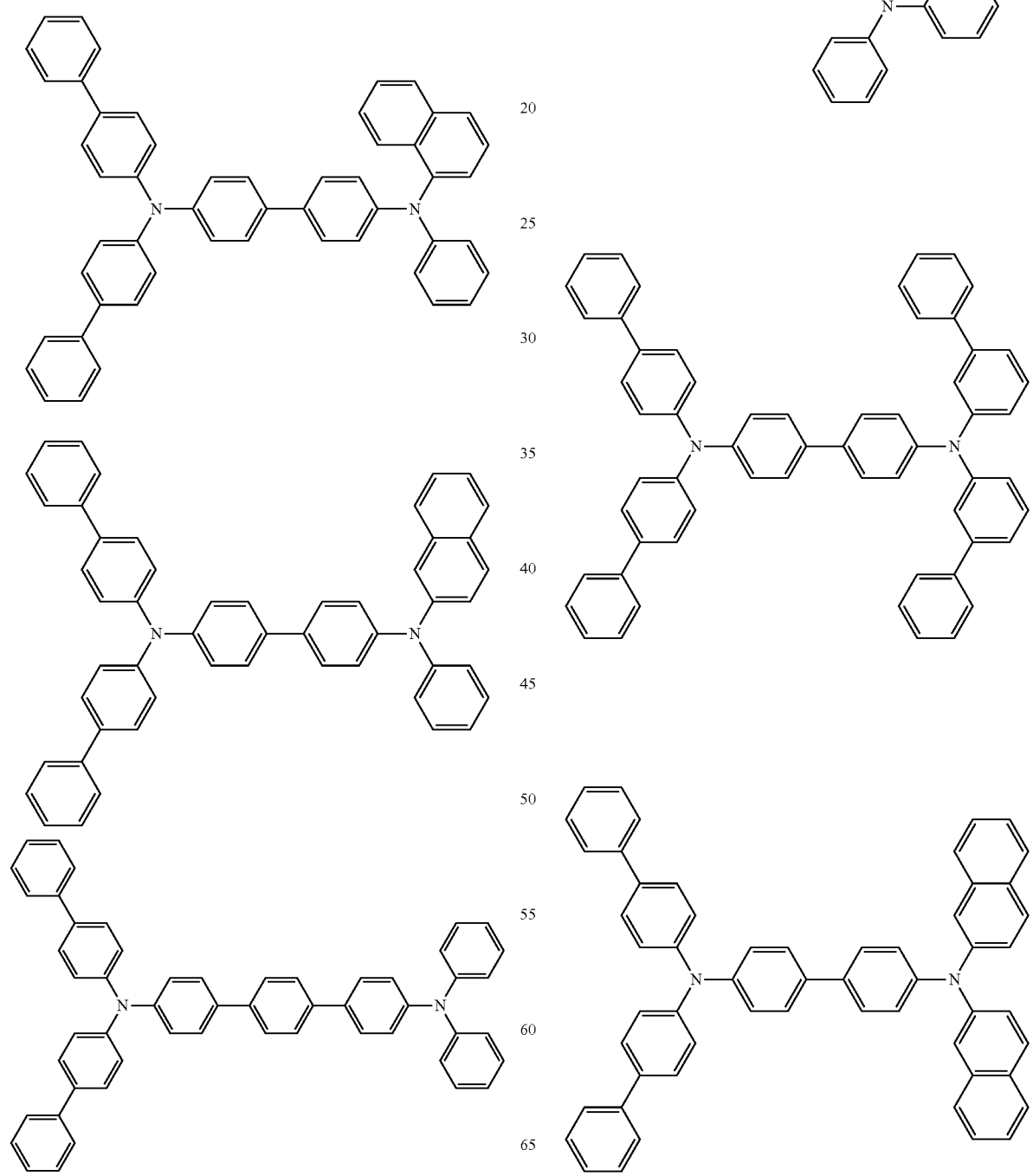

71
-continued
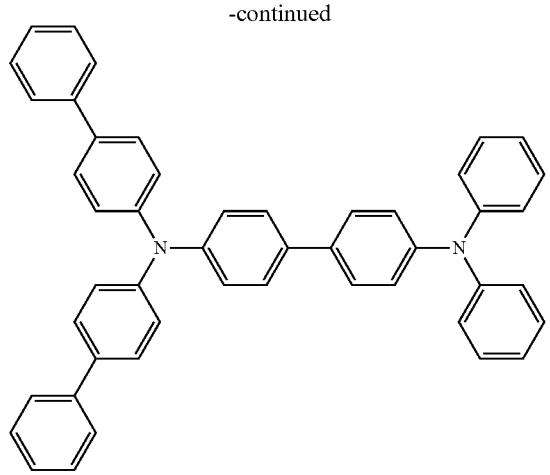
72
-continued
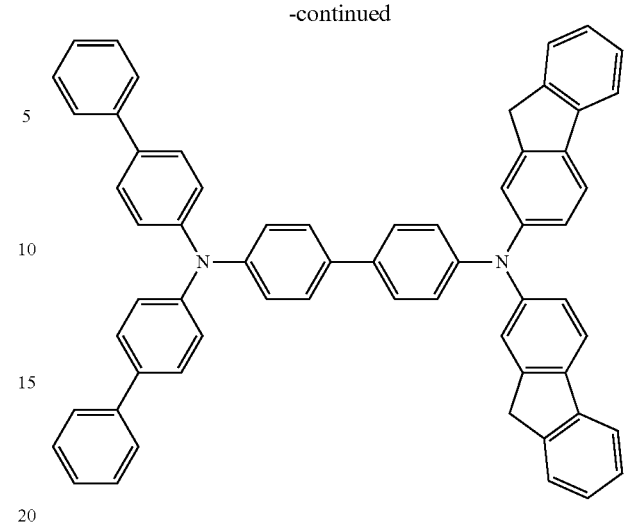
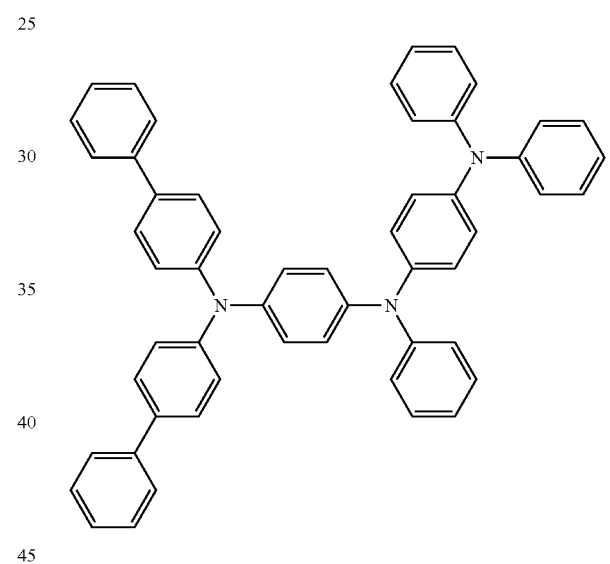
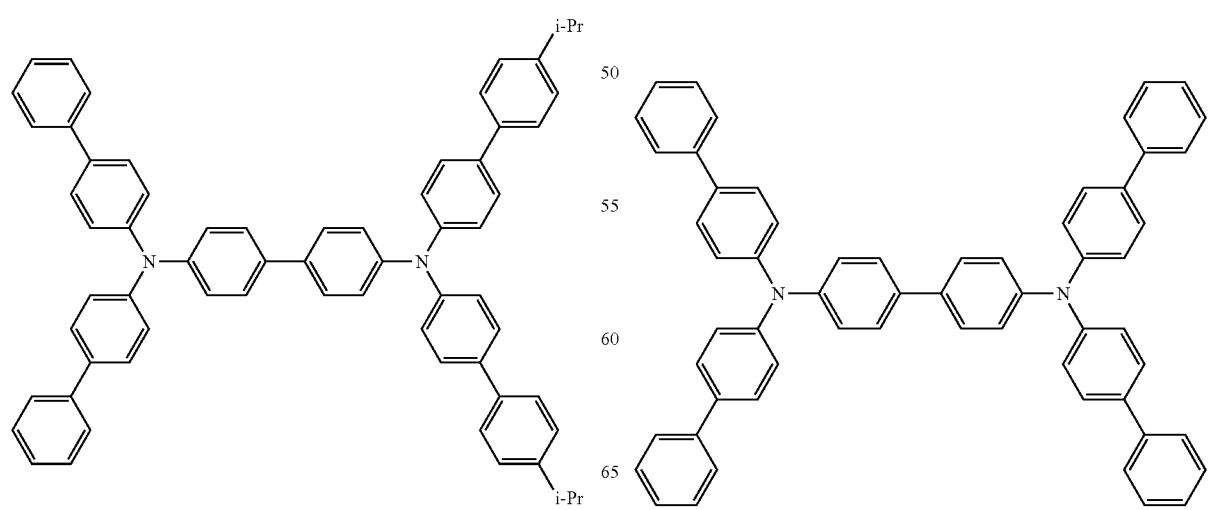

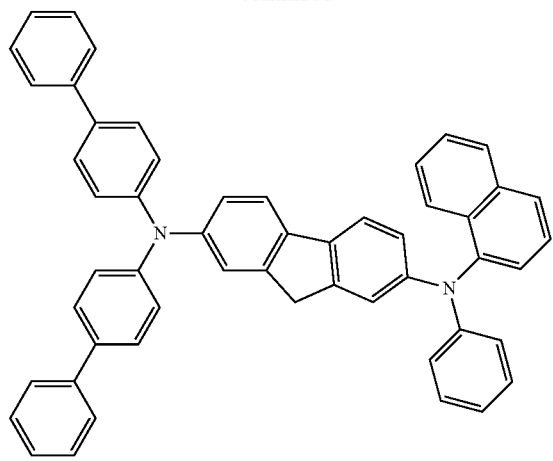
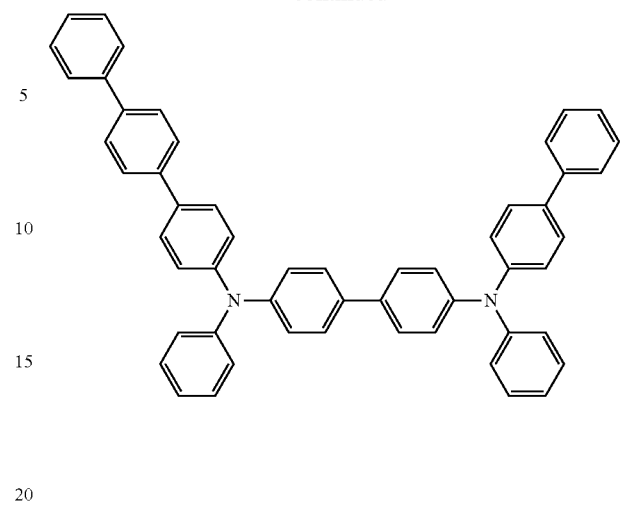
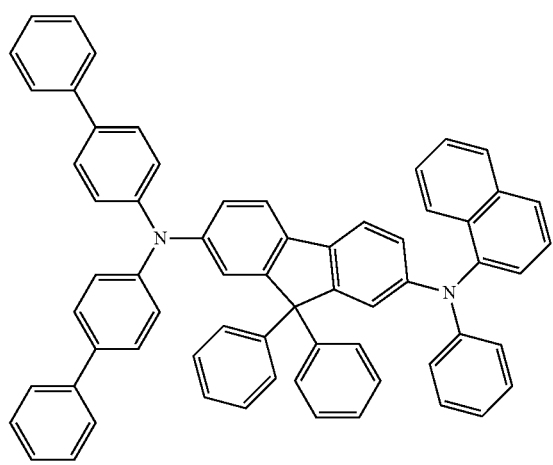
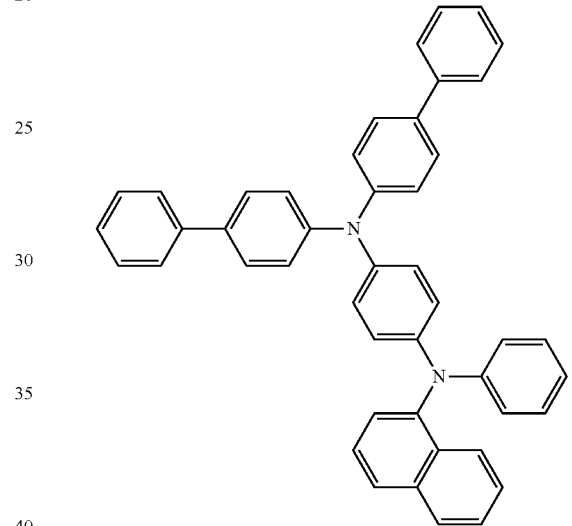
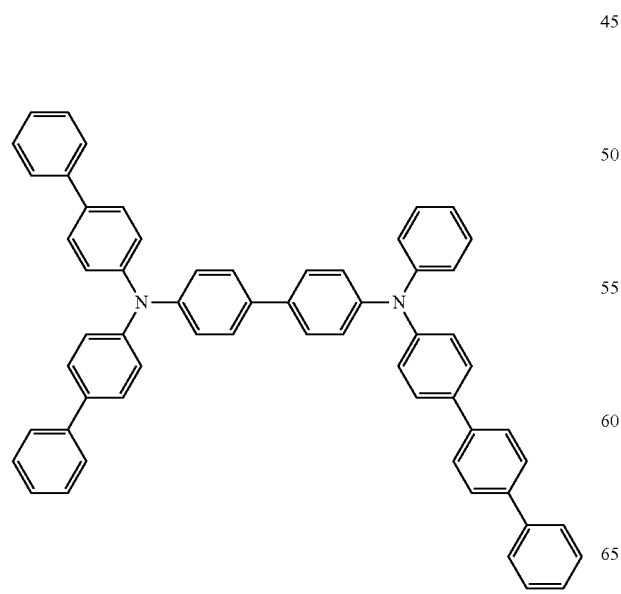
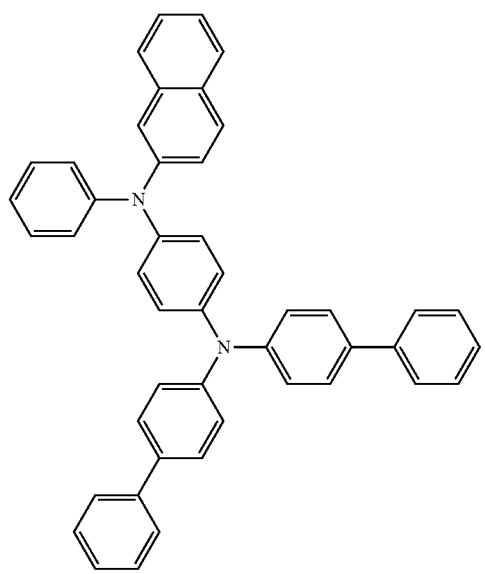

75
-continued
76
-continued
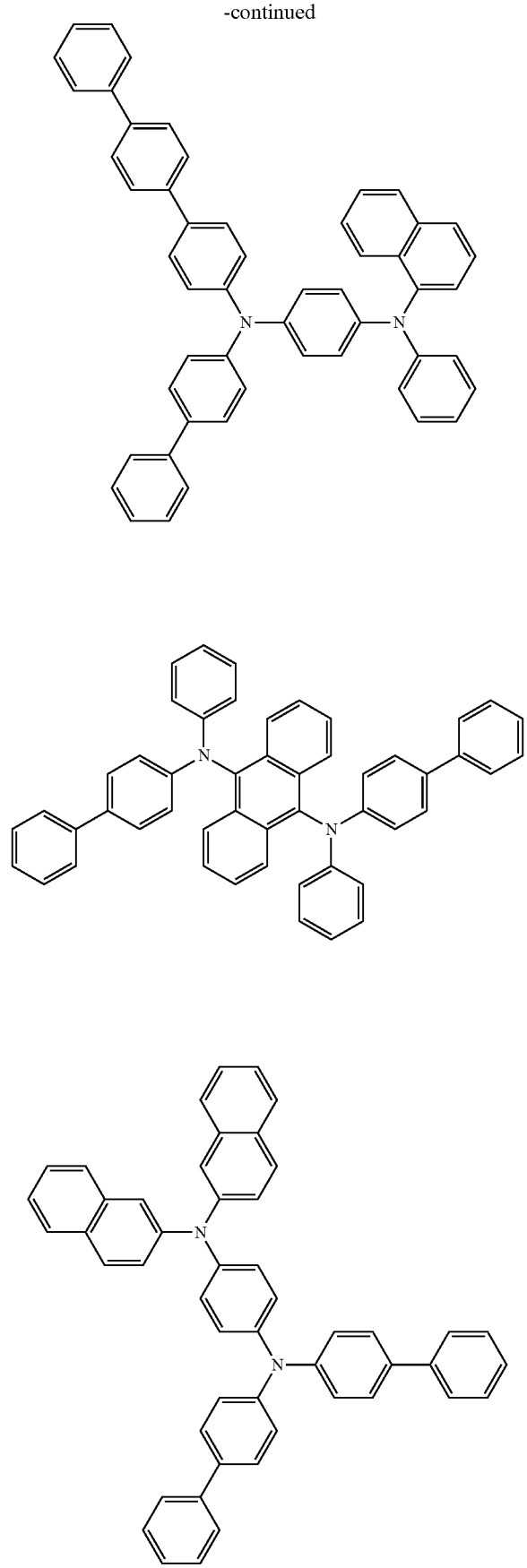
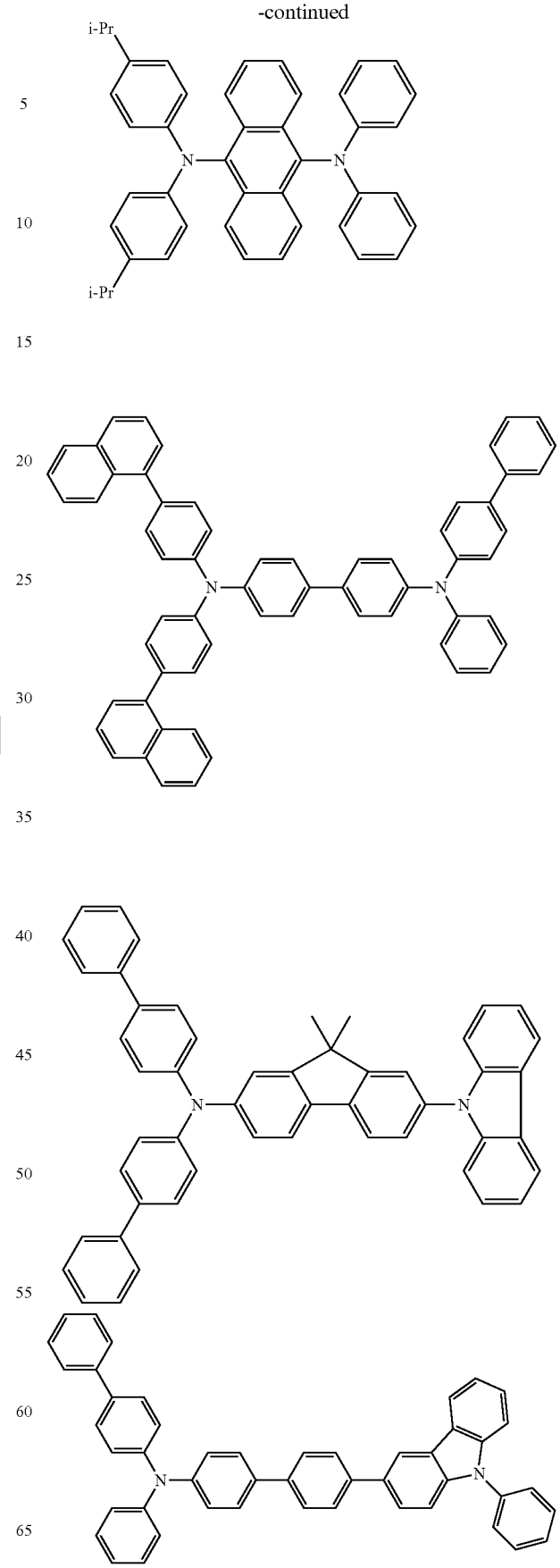

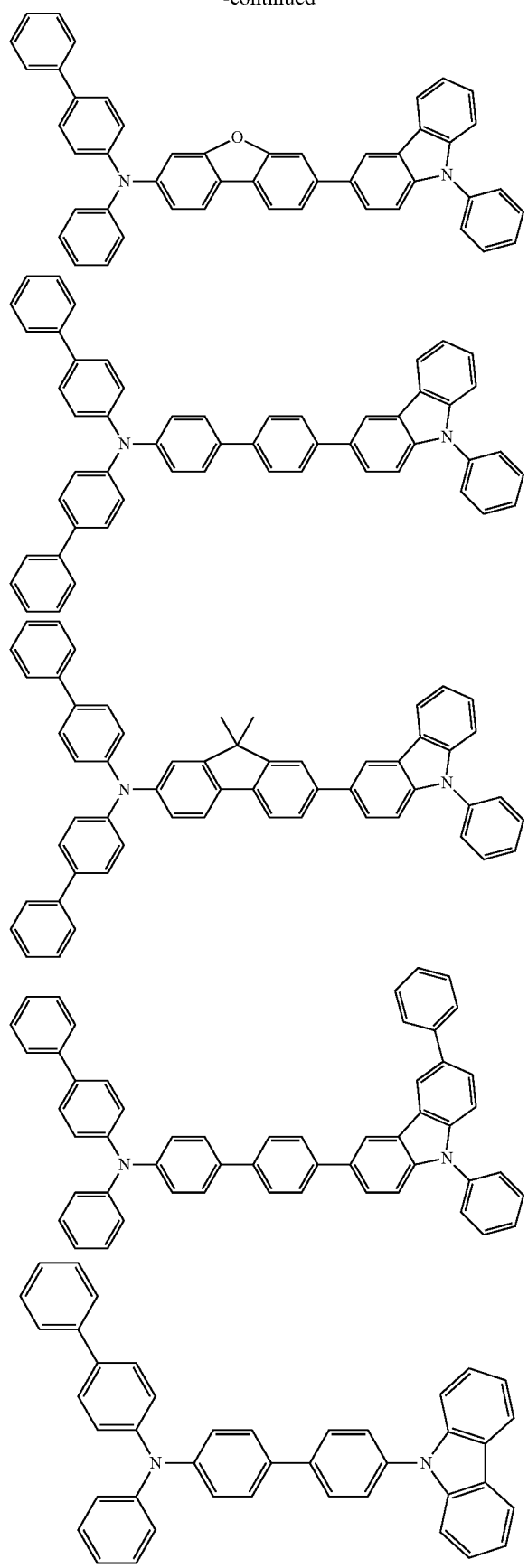
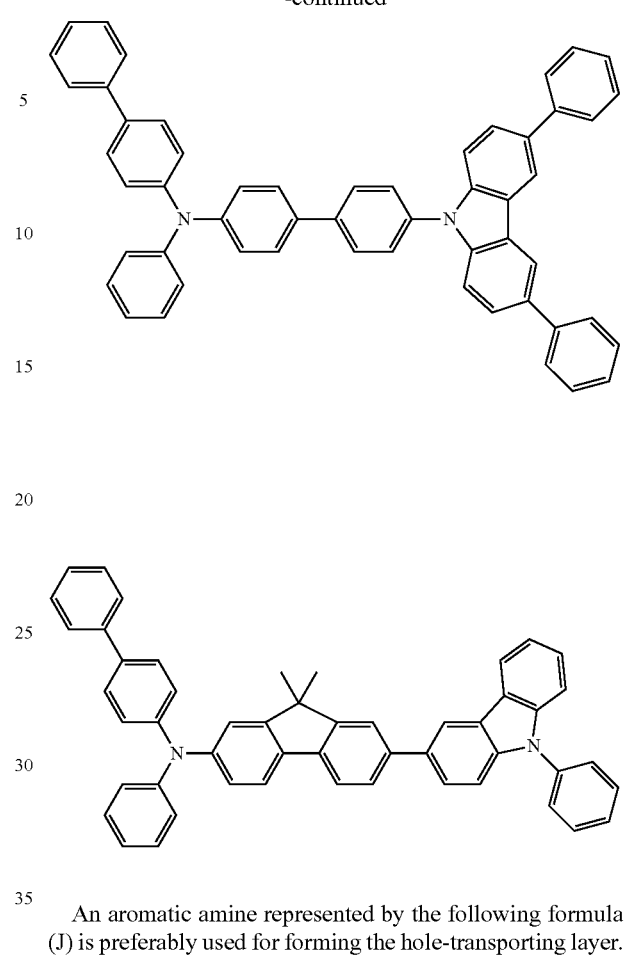
An aromatic amine represented by the following formula (J) is preferably used for forming the hole-transporting layer.
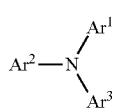
(J)
In the formula (J), $Ar^1$ to $Ar^a$ are as defined for $Ar^1$ to $Ar^4$ in the formula (H). Specific examples of the compound represented by the formula (J) will be shown below. The compound represented by the formula (J) is not limited to these.
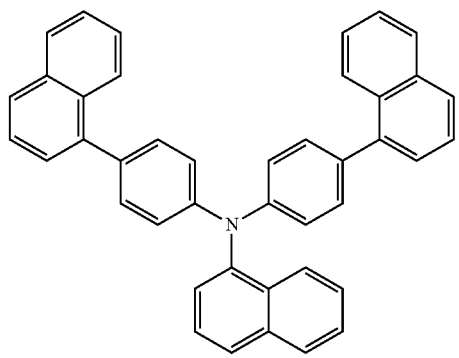

-continued
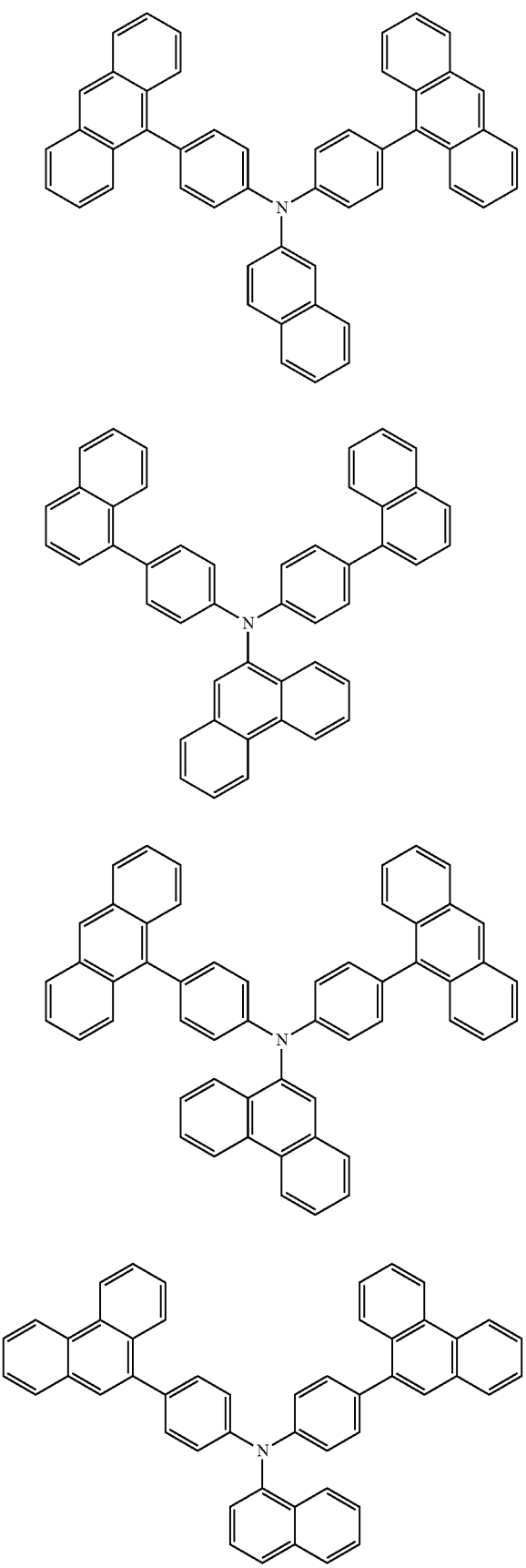
-continued
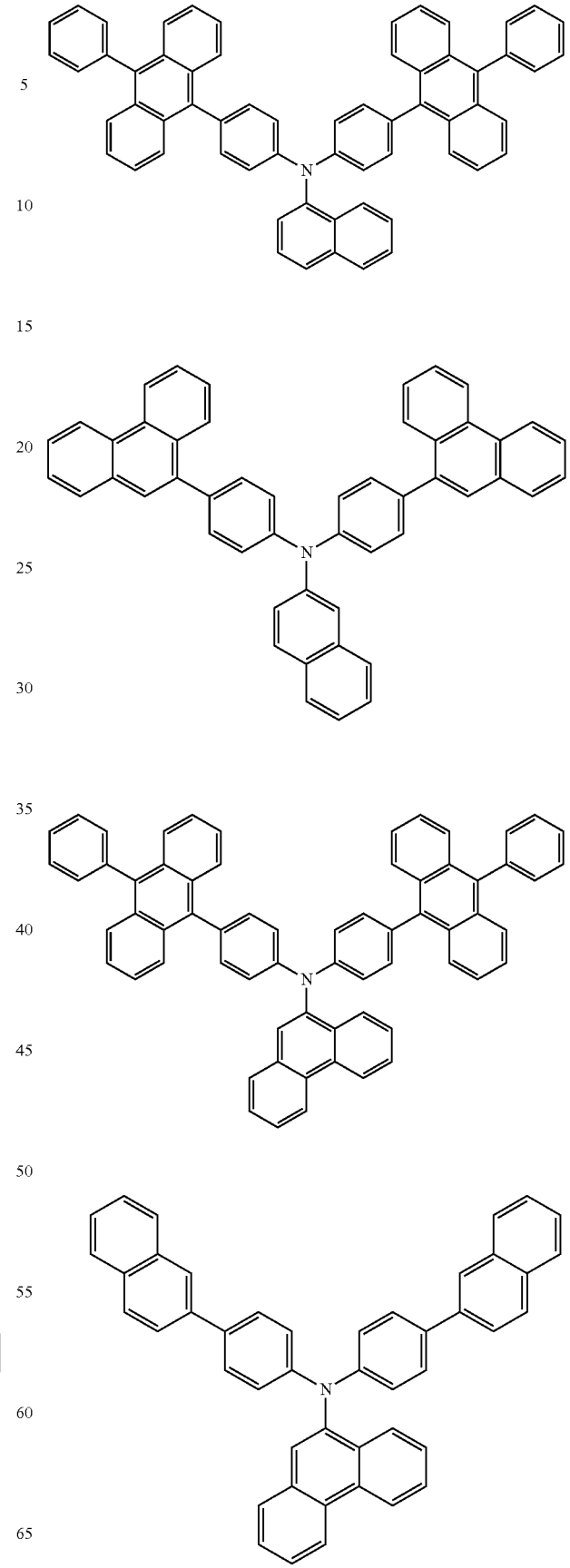

81
-continued
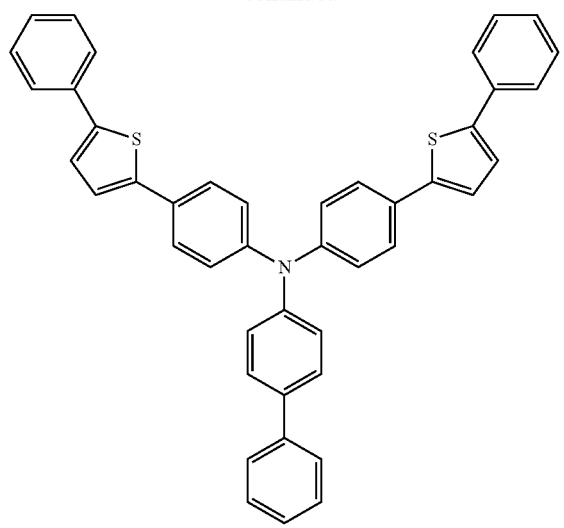
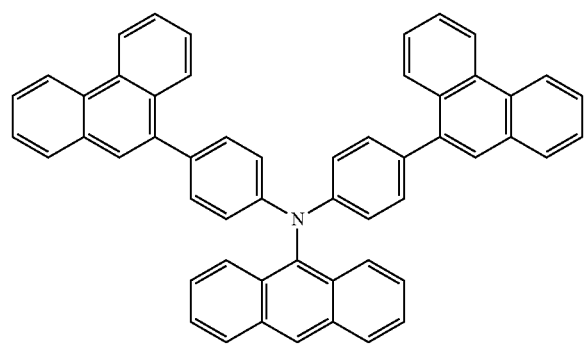
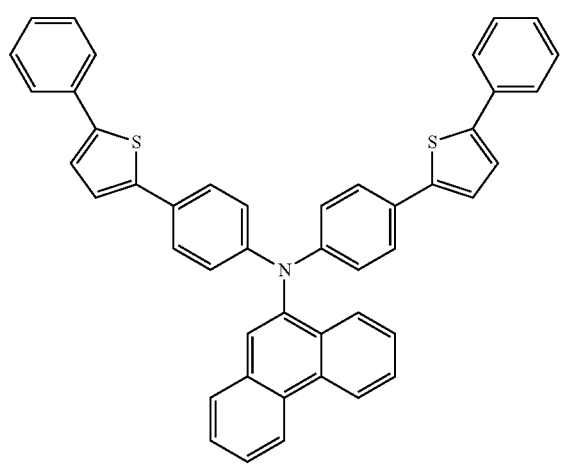
82
-continued
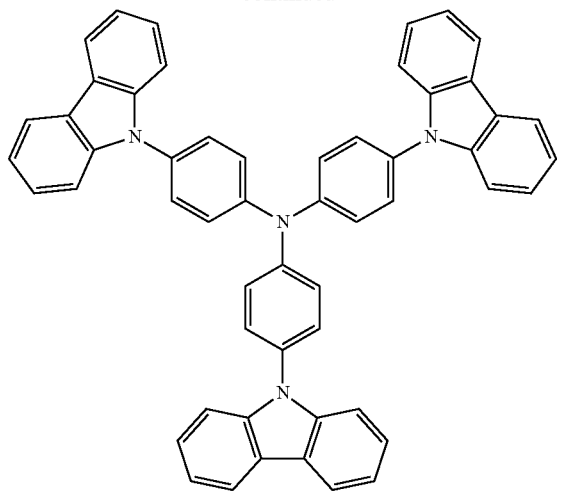
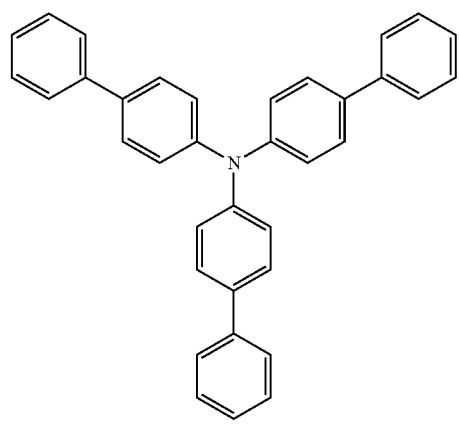
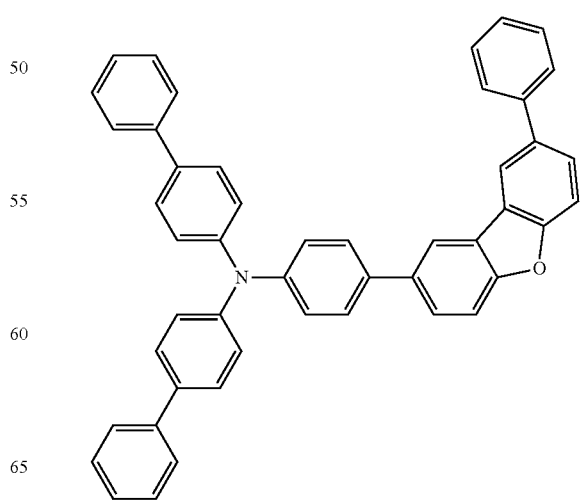

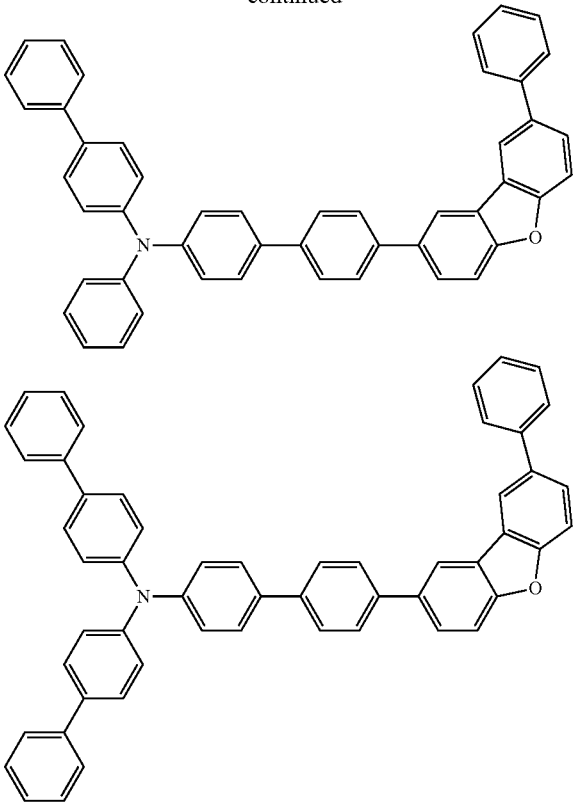

The hole-transporting layer of the organic EL device according to one embodiment of the invention may have a two-layer structure of a first hole-transporting layer (nearer to the anode) and a second hole-transporting layer (nearer to the cathode).

The thickness of the hole-transporting layer is not particularly restricted, but preferably 10 to 200 nm.

In the organic EL device according to one embodiment of the invention, a layer comprising an acceptor material may be connected to the anode side of the hole-transporting layer or the first hole-transporting layer. As a result, a lowering in driving voltage or a decrease in production cost can be expected.

As the acceptor material, a compound represented by the following formula (K) is preferable.

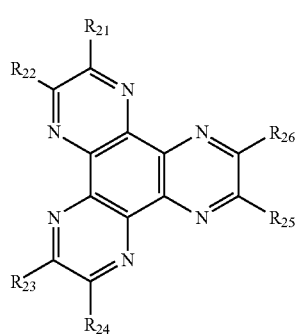

(K)

In the formula (K), $R_{21}$ to $R_{26}$, which may be the same or different, are independently a cyano group, $—CONH_2$, a carboxyl group or $—COOR_{27}$ ($R_{27}$ is an alkyl group including 1 to 20 carbon atoms or a cycloalkyl group including 3 to 20 carbon atoms); provided that, one or two pairs of $R_{21}$ and $R_{22}$; $R_{23}$ and $R_{24}$; and $R_{25}$ and $R_{26}$ may be bonded to each other to form a group represented by $—CO—O—CO—$.

As $R_{27}$, a methyl group, an ethyl group, an n-propyl group, an isopropyl group, an n-butyl group, an isobutyl group, a t-butyl group, a cyclopentyl group, a cyclohexyl group or the like can be given.

The thickness of the layer that comprises an acceptor material is not particularly limited, but preferably 5 to 20 nm.

(n/p Doping)

In the hole-transporting layer or the electron-transporting layer mentioned above, as described in the Japanese Patent No. 3695714, the carrier injecting performance can be adjusted by doping (n) of a donor material or doping (p) of an acceptor material.

As representative examples of the n-doping, a method in which an electron-transporting material is doped with a metal such as Li and Cs can be mentioned. As the represented example of the p-doping, a method in which a hole-transporting material is doped with an acceptor material such as $F_4TCNQ$ (2,3,5,6-tetrafluoro-7,7,8,8-tetracyanoquinodimethane) can be given.

(Spacing Layer)

The spacing layer is a layer provided between the fluorescent emitting layer and the phosphorescent emitting layer in order to prevent diffusion of excitons generated in the phosphorescent emitting layer to the fluorescent emitting layer when the fluorescent emitting layer and the phosphorescent emitting layer are stacked or in order to adjust the carrier balance. Further, the spacing layer can be provided between the plural phosphorescent emitting layers.

Since the spacing layer is provided between the emitting layers, the material for the spacing layer is preferably a material having both electron-transporting properties and hole-transporting properties. In order to prevent diffusion of the triplet energy in adjacent phosphorescent emitting layers, it is preferred that the spacing layer have a triplet energy of 2.6 eV or more. As the material used for the spacing layer, the same material as those used in the above-mentioned hole-transporting layer can be given.

(Barrier Layer)

It is preferred that the organic EL device according to one embodiment of the invention have a barrier layer such as an electron-barrier layer, a hole-barrier layer and a triplet barrier layer in a part that is adjacent to the emitting layer. Here, the electron-barrier layer is a layer that serves to prevent leakage of electrons from the emitting layer to the hole-transporting layer, and the hole-barrier layer is a layer that serves to prevent leakage of holes from the emitting layer to the electron-transporting layer.

The triplet barrier layer prevents diffusion of triplet excitons generated in the emitting layer to the surrounding layers, and has a function of preventing energy deactivation of triplet excitons on molecules on the electron-transporting layer other than the emitting dopant by confining the triplet excitons within the emitting layer.

When the triplet barrier layer is provided, in the phosphorescent emitting device, the following is considered. If the triplet energy of the phosphorescent emitting dopant is taken as $E^T_d$ and the triplet energy of the compound used as the triplet barrier layer is taken as $E^T_{TB}$, if the energy relationship $E^T_d < E^T_{TB}$ is satisfied, in respect of energy, the triplet excitons of the phosphorescent emitting dopant is confined (i.e. the triplet excitons cannot be moved to other molecules), whereby the energy deactivation route other than emission on the dopant is cut off, leading to efficient emission. However, even when the relationship $E^T_d < E^T_{TB}$ is established, if the energy difference $\Delta E^T = E^T_{TB} - E^T_d$ is small, it is thought that, in an environment at around room temperature where the device is actually driven, due to thermal energy of the surrounding area, the triplet excitons can move to other molecules by endothermically overcoming this energy difference $\Delta E^T$. In particular, in the case of phosphorescent emission that has a longer exciton life as compared with fluorescent emission, effects of the endothermic move of excitons relatively tend to appear. Relative to the thermal energy at room temperature, a larger energy difference $\Delta E^T$ is preferable. The energy difference $\Delta E^T$ is further preferably 0.1 eV or more, and particularly preferably 0.2 eV or more. On the other hand, in a fluorescent device, as the triplet barrier layer of the TTF device configuration disclosed in WO2010/134350A1, the material for an organic EL device according to one embodiment of the invention can be used.

The electron mobility of the material constituting the triplet barrier layer is desirably $10^{-6}$ cm$^2$/Vs or more in a field intensity range of 0.04 to 0.5 MV/cm. As the method for measuring the electron mobility of an organic material, several methods that include the Time of Flight method are known. Here, the electron mobility means an electron mobility that is determined by the impedance spectroscopy.

The electron mobility of the electron-injecting layer is desirably $10^{-6}$ cm$^2$/Vs or more in a field intensity range of 0.04 to 0.5 MV/cm. The reason is that, by this electron mobility, injection of electrons from the cathode to the electron-transporting layer is promoted, and as a result, injection of electrons to adjacent barrier layer and emitting layer is promoted, enabling the device to be driven at a lower voltage.

The organic EL device according to one embodiment of the invention can be used as an electronic device including a display element such as an organic EL panel module; a display such as a TV, a mobile phone and a PC; and emitting devices such as lightings and lights for automobiles or the like.

EXAMPLES

Example 1

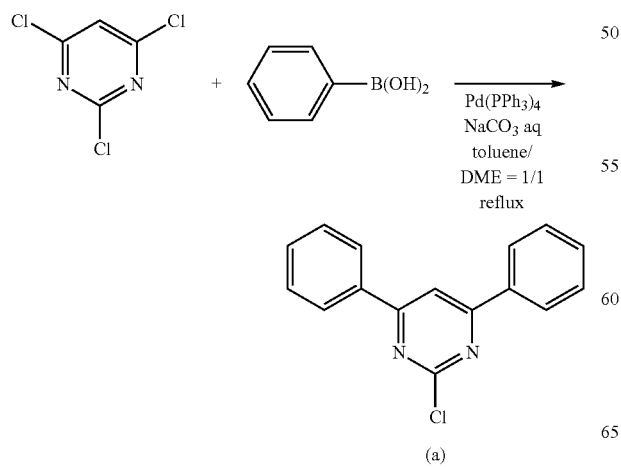

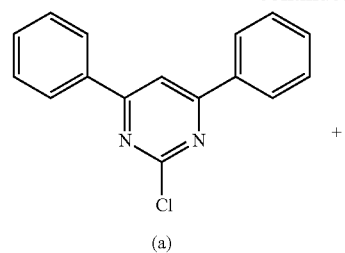

(a)

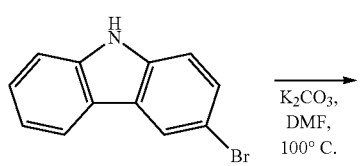

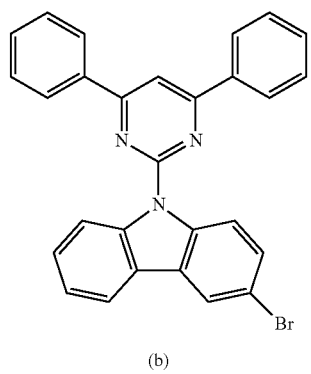

(b)

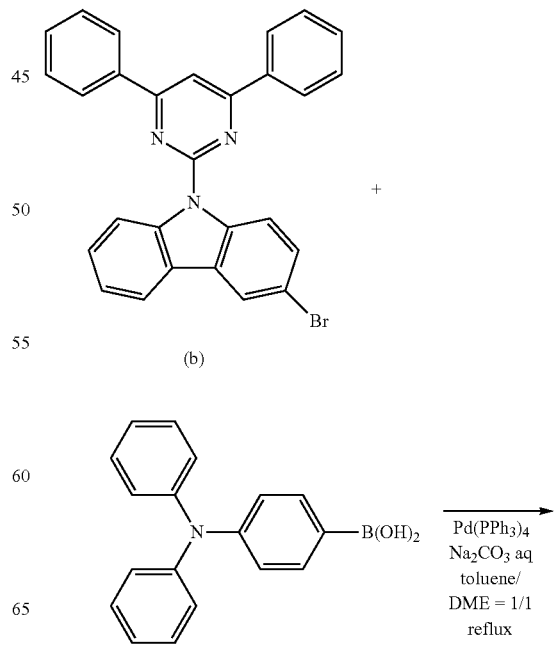

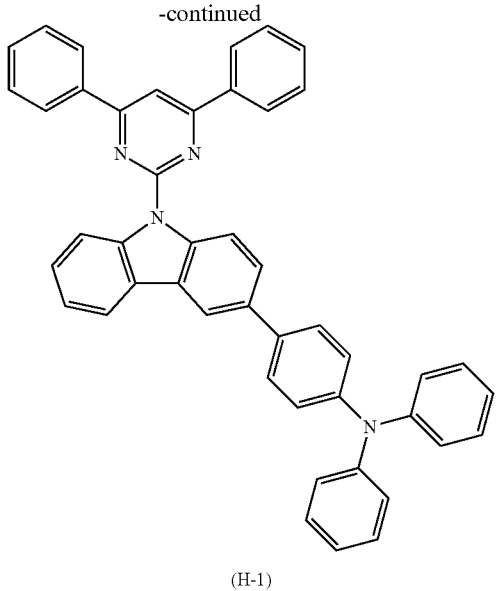

(H-1)

In an argon atmosphere, in a 500 mL-three-neck flask, 2,4,6-trichloropyrimidine (5 g, 27.3 mmol), phenylboronic acid (6.7 g, 54.9 mmol), tetrakistriphenylphosphine palladium (1.26 g, 1.09 mmol), dimethoxyethane (DME, 100 mL) and an aqueous 2M sodium carbonate solution (82 mL, 164 mmol) were added. The resultant was allowed to react while heating under reflux for 8 hours. After cooling the reaction liquid to room temperature, an aqueous layer was removed by separation, and an organic layer was dried with magnesium sulfate. Insoluble matters were removed by filtration, and the organic solvent was distilled off under reduced pressure. The resulting residues were purified by silica gel column chromatography, whereby an intermediate (a) (5.6 g, yield 76.9%) was obtained.

In an argon atmosphere, in a 300 mL-three-neck flask, intermediate (a) (5.3 g, 20 mmol), 3-bromocarbazole (5.17 g, 21 mmol), potassium carbonate (3.32 g, 24 mmol) and dimethylformamide (DMF, 50 mL) were added. The resultant was allowed to react while heating under reflux at 100° C. for 8 hours. After cooling the reaction liquid to room temperature, insoluble matters were removed by filtration, and the organic solvent was distilled off under reduced pressure. The resulting residues were purified by silica gel column chromatography, whereby an intermediate (b) (9.3 g, yield 97.6%) was obtained.

In an argon atmosphere, in a 100 mL-three-neck flask, intermediate (b) (2.4 g, 5 mmol), diphenylaminophenylboronic acid (1.4 g, 5 mmol), tetrakistriphenylphosphine palladium (120 mg, 0.1 mmol), dimethoxyethane (DME, 10 mL), toluene (10 mL) and an aqueous 2M sodium carbonate solution (7.5 mL, 15 mmol) were added. The resultant was heated under reflux for 8 hours. After cooling the reaction liquid to room temperature, an aqueous layer was removed by separation, and an organic layer was dried with magnesium sulfate. Insoluble matters were removed by filtration, and the organic solvent was distilled off under reduced pressure. The resulting residues were purified by silica gel column chromatography, whereby an intended product H-1 (2.1 g, yield 65.5%) was obtained.

For the resulting compound, a HPLC analysis and a FD-MS analysis were conducted. The results of these analyses are shown below.

HPLC: purity 99.5%
FD-MS: calcd for C46H32N4=640.77.
found m/z=641 (M+100).

Example 2

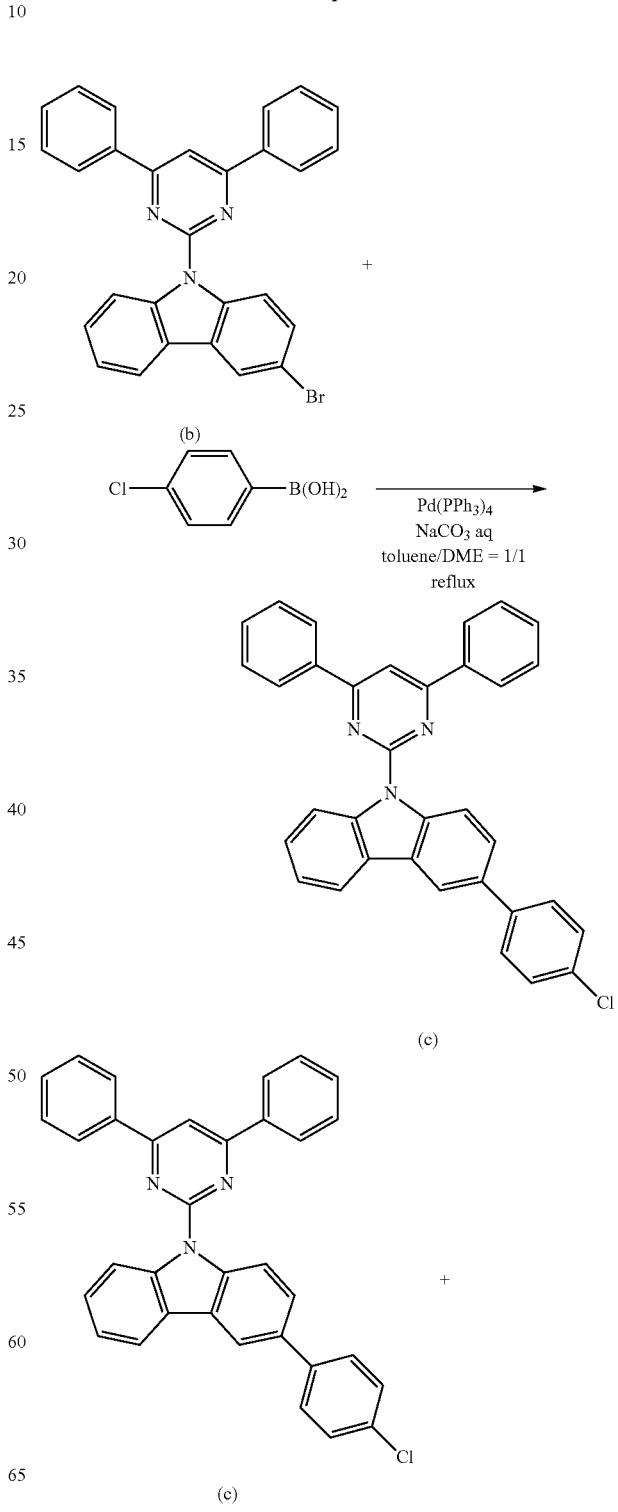

Example 3

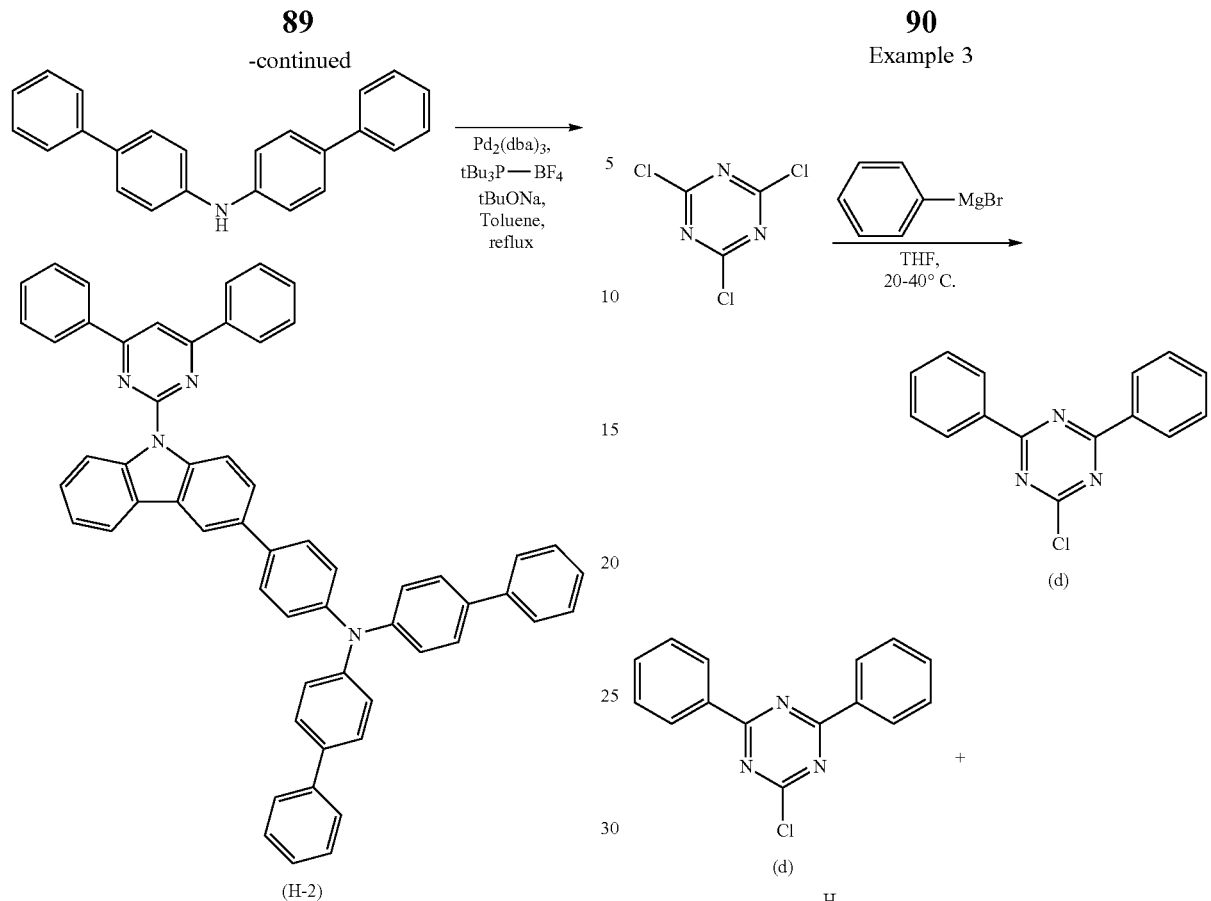

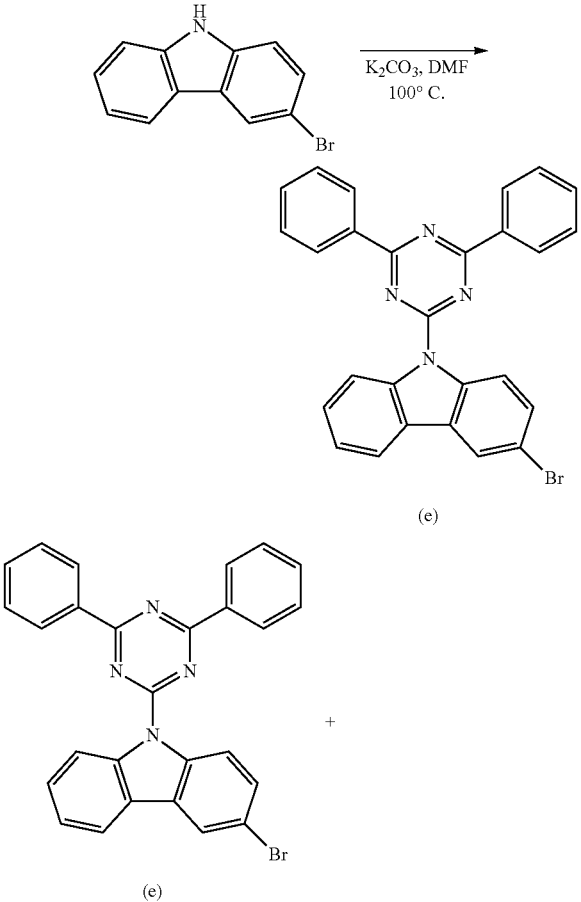

In an argon atmosphere, in a 300 mL-three-neck flask, intermediate (b) (6.9 g, 14.5 mmol), 4-chlorophenylboronic acid (2.38 g, 15.2 mmol), tetrakistriphenylphosphine palladium (335 mg, 0.29 mmol), dimethoxyethane (DME, 30 mL), toluene (30 mL) and an aqueous 2M sodium carbonate solution (22 mL, 44 mmol) were added. The resultant was allowed to react while heating under reflux for 8 hours. After cooling the reaction liquid to room temperature, an aqueous layer was removed by separation, and an organic layer was dried with magnesium sulfate. Insoluble matters were removed by filtration, and the organic solvent was distilled off under reduced pressure. The resulting residues were purified by silica gel column chromatography, whereby an intermediate (c) (6.56 g, yield 89.1%) was obtained.

In an argon atmosphere, in a 100 mL-three-neck flask, intermediate (c) (2 g, 3.9 mmol), bisphenylamine (1.25 g, 3.9 mmol), tris(dibenzylideneacetone)dipalladium (71 mg, 0.078 mmol), tri-t-butylphosphonium tetrafluoroborate (87 mg, 0.3 mmol), sodium t-butoxide (0.52 g, 5.5 mmol) and xylene anhydride (20 mL) were added in sequence. The resultant was heated under reflux for 8 hours.

After cooling the reaction liquid to room temperature, insoluble matters were removed by filtration, and the organic solvent was distilled off under reduced pressure. The resulting residues were purified by silica gel column chromatography, whereby H-2 (2 g, yield 64.7%) was obtained.

For the resulting compound, a HPLC analysis and a FD-MS analysis were conducted. The results of the analyses are shown below.

HPLC: purity 99.6%
FD-MS: calcd for C58H40N4=792.96.
found m/z=793 (M+100).

-continued

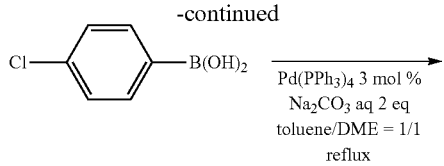

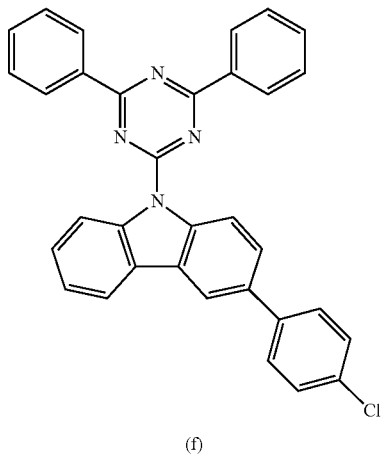

(f)

+

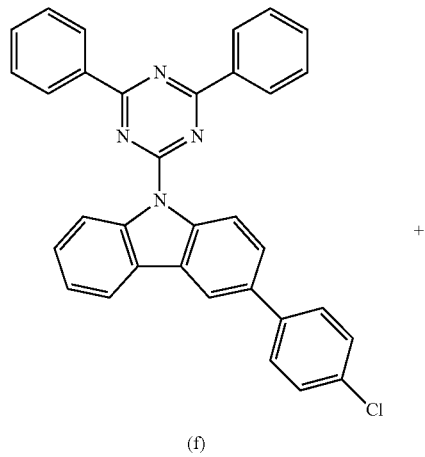

(f)

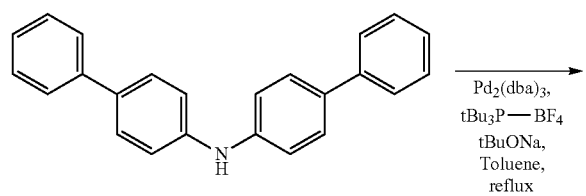

-continued

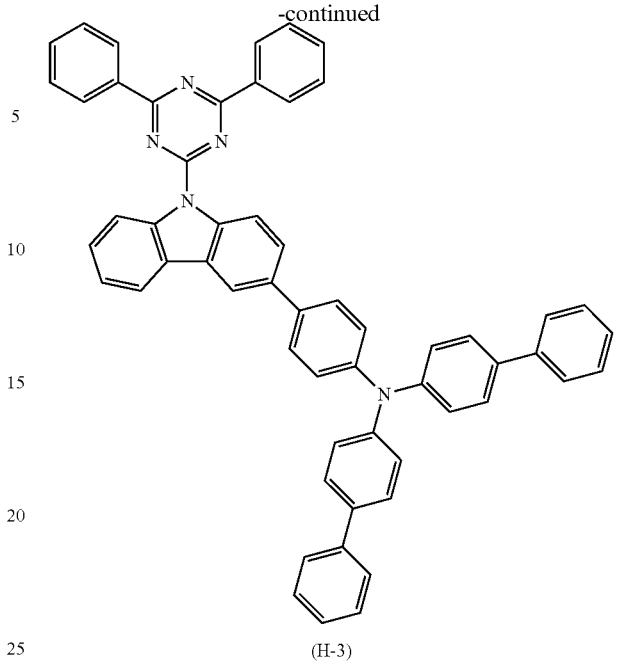

(H-3)

In an argon atmosphere, in a 500 mL-three-neck flask, 2,4,6-trichlorotriazine (47.2 g, 256 mmol) and dehydrated tetrahydrofuran (THF, 470 ml) were placed. While keeping the temperature of the reaction liquid at 20 to 40° C., 1M-phenylmagenisum bromide (640 ml, 640 mmol) was added dropwise for 30 minutes, followed by stirring for 16 hours. Subsequently, while keeping the temperature of the reaction liquid at 5 to 15° C., 150 ml of ion exchange water was added dropwise. A reaction product was extracted with ethyl acetate, and an organic layer was dried with magnesium sulfate. Insoluble matters were removed by filtration, and the organic solvent was distilled off under reduced pressure. The resulting residues were purified by silica gel column chromatography, whereby an intermediate (d) (22.7 g, yield 33%) was obtained.

In an argon atmosphere, in a 300-mL-three-neck flask, intermediate (d) (5.3 g, 20 mmol), 3-bromocarbazole (5.17 g, 21 mmol), potassium carbonate (3.32 g, 24 mmol) and dimethylformamide (DMF, 50 mL) were added. The resultant was heated under reflux at 100° C. for 8 hours. After cooling the reaction liquid to room temperature, insoluble matters were removed by filtration, and the organic solvent was distilled off under reduced pressure. The resulting residues were purified by silica gel column chromatography, whereby an intermediate (e) (8.9 g, yield 93.2%) was obtained.

In an argon atmosphere, in a 300-mL-three-neck flask, intermediate (e) (6.9 g, 14.5 mmol), 4-chlorophenylboronic acid (2.38 g, 15.2 mmol), tetrakistriphenylphosphine palladium (335 mg, 0.29 mmol), dimethoxyethane (DME, 30 mL), toluene (30 mL) and an aqueous 2M sodium carbonate solution (22 mL, 44 mmol) were added. The resultant was allowed to react under reflux for 8 hours. After cooling the reaction liquid to room temperature, an aqueous layer was removed by separation and an organic layer was dried with magnesium sulfate. Insoluble matters were removed by filtration, and the organic solvent was removed under reduced pressure. The resulting residues were purified by silica gel column chromatography, whereby an intermediate (f) (6.45 g, yield 87.4%) was obtained.

In an argon atmosphere, in a 100-mL-three-neck flask, intermediate (f) (2 g, 3.9 mmol), bisbiphenylamine (1.3 g, 3.9 mmol), tris(dibenzylideneacetone)dipalladium (71 mg, 0.078 mmol), tri-t-butylphosphonium tetrafluoroborate (0.09 g, 0.3 mmol), sodium t-butoxide (0.52 g, 5.5 mmol) and xylene anhydride (20 mL) were sequentially added. The resultant was heated under reflux for 8 hours.

After cooling the reaction liquid to room temperature, insoluble matters were removed by filtration, and the organic solvent was distilled off under reduced pressure. The resulting residues were purified by silica gel column chromatography, whereby H-3 (2.3 g, yield 74.3%) was obtained.

For the obtained compound, a HPLC analysis and a FD-MS analysis were conducted. The results of these analyses are shown below.

HPLC: purity 99.5%

FD-MS: calcd for C57H39N5=793.95.

found m/z=794 (M+100).

Example 4

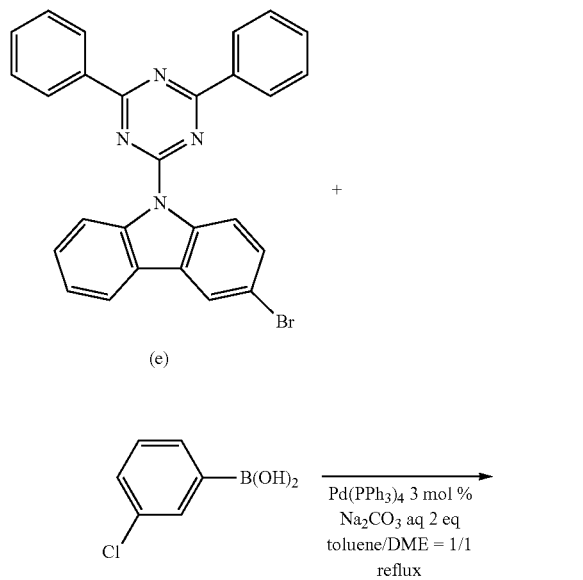

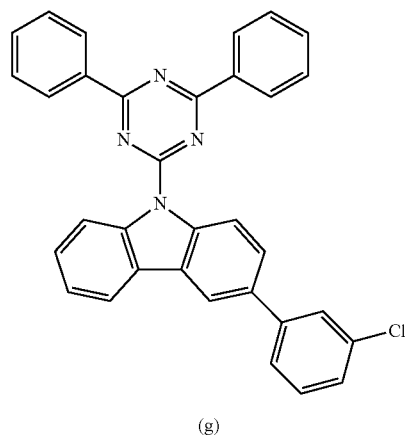

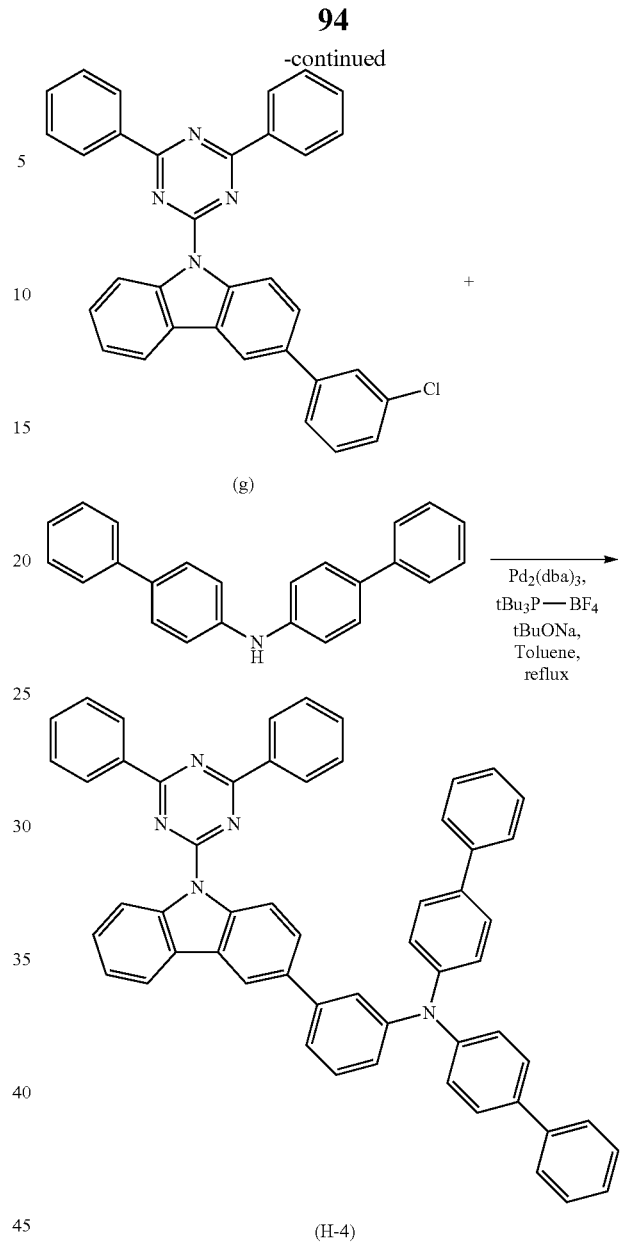

In an argon atmosphere, in a 300-mL-three-neck flask, intermediate (e) (6.9 g, 14.5 mmol), 3-chlorophenylboronic acid (2.38 g, 15.2 mmol), tetrakistriphenylphosphine palladium (335 mg, 0.29 mmol), dimethoxyethane (DME, 30 mL), toluene (30 mL) and an aqueous 2M sodium carbonate solution (22 mL, 44 mmol) were added. The resultant was allowed to react under reflux for 8 hours. After cooling the reaction liquid to room temperature, an aqueous layer was removed by separation and an organic layer was dried with magnesium sulfate. Insoluble matters were removed by filtration, and the organic solvent was removed under reduced pressure. The resulting residues were purified by silica gel column chromatography, whereby intermediate (g) (6.3 g, yield 85.4%) was obtained.

In an argon atmosphere, in a 100-mL-three-neck flask, intermediate (g) (2 g, 3.9 mmol), bisbiphenylamine (1.3 g, 3.9 mmol), tris(dibenzylideneacetone)dipalladium (71 mg, 0.078 mmol), tri-t-butylphosphonium tetrafluoroborate (0.09 g, 0.3 mmol), sodium t-butoxide (0.52 g, 5.5 mmol) and xylene anhydride (20 mL) were sequentially added. The resultant was heated under reflux for 8 hours.

After cooling the reaction liquid to room temperature, insoluble matters were removed by filtration, and the organic solvent was distilled off under reduced pressure. The resulting residues were purified by silica gel column chromatography, whereby HA (2.2 g, yield 71.1%) was obtained.

For the obtained compound, a HPLC analysis and a FD-MS analysis were conducted. The results of the analyses are shown below.

HPLC: purity 99.5%

FD-MS: calcd for C57H39N5=793.95.

found m/z=794 (M+100).

Example 5

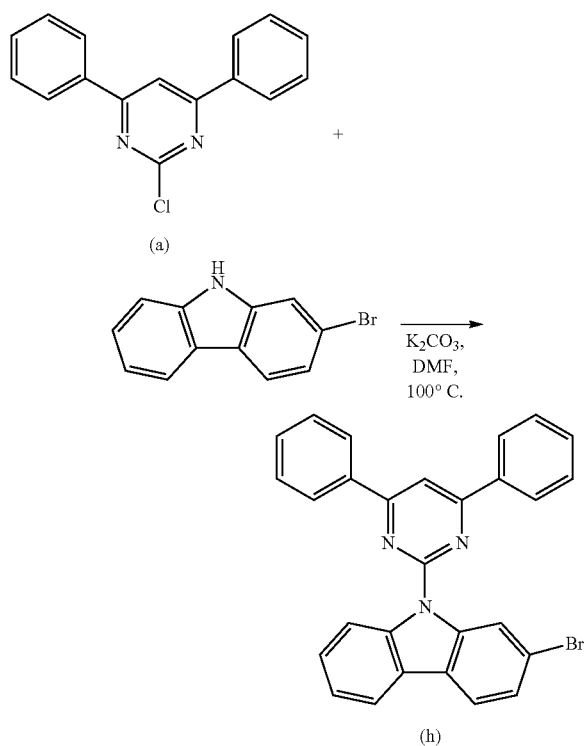

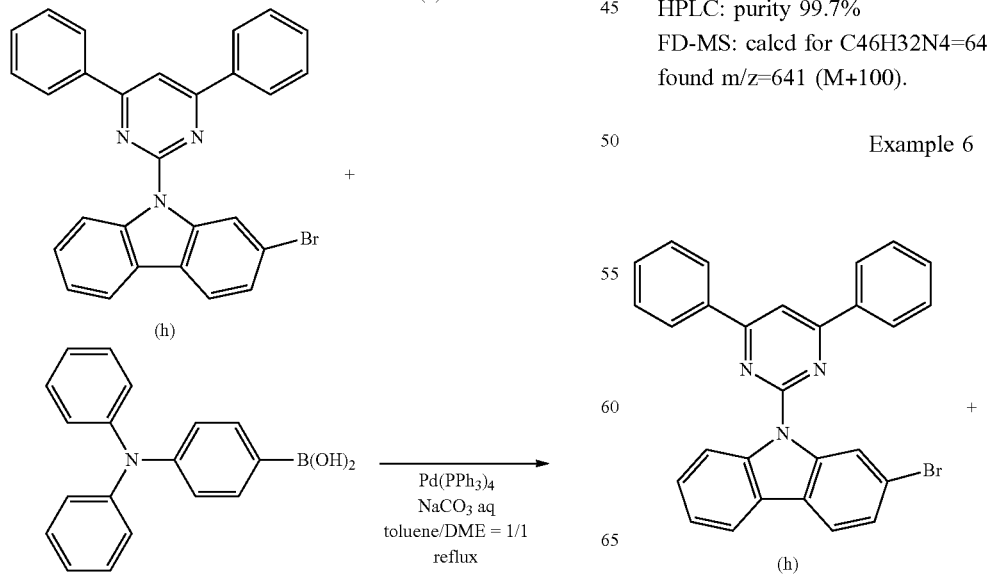

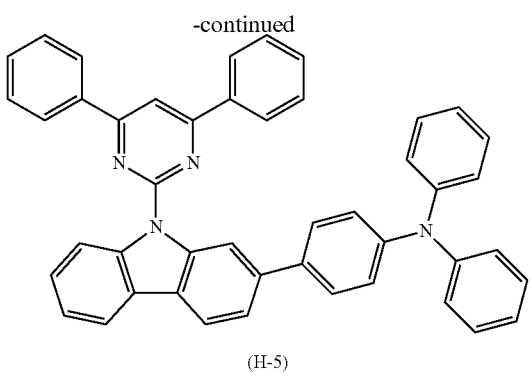

(H-5)

In an argon atmosphere, in a 300-mL-three-neck flask, intermediate (a) (5.6 g, 21 mmol), 2-bromocarbazole (5.43 g, 22.1 mmol), potassium carbonate (3.48 g, 25.2 mmol), dimethylformamide (DMF, 50 mL) were added, and the resultant was heated under reflux at 100° C. for 8 hours. After cooling the reaction liquid to room temperature, insoluble matters were removed by filtration, and the organic solvent was removed under reduced pressure. The resulting residues were purified by silica gel column chromatography, whereby intermediate (h) (9.0 g, yield 90%) was obtained.

In an argon atmosphere, in a 100-mL-three-neck flask, intermediate (h) (2.4 g, 5 mmol), diphenylaminophenylboronic acid (1.4 g, 5 mmol), tetrakistriphenylphosphine palladium (120 mg, 0.1 mmol), dimethoxyethane (DME, 10 mL), toluene (10 mL) and an aqueous 2M sodium carbonate solution (7.5 mL, 15 mmol) were added. The resultant was allowed to react while heating under reflux for 8 hours. After cooling the reaction liquid to room temperature, an aqueous layer was removed by separation and an organic layer was dried with magnesium sulfate. Insoluble matters were removed by filtration, and the organic solvent was removed under reduced pressure. The resulting residues were purified by silica gel column chromatography, whereby an intended product H-5 (2.0 g, yield 62.4%) was obtained.

For the obtained compound, a HPLC analysis and a FD-MS analysis were conducted. The results of these analyses are shown below.

HPLC: purity 99.7%

FD-MS: calcd for C46H32N4=640.77.

found m/z=641 (M+100).

Example 6

-continued

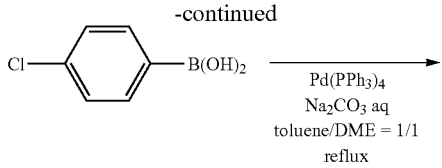

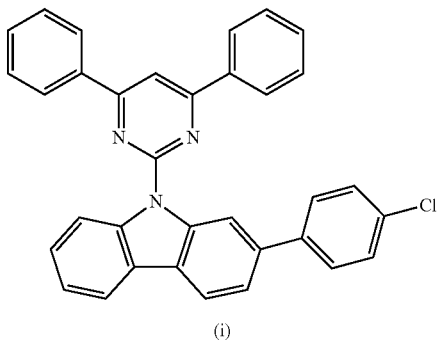

(i)

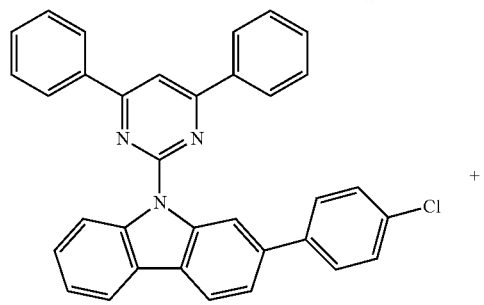

(i)

+

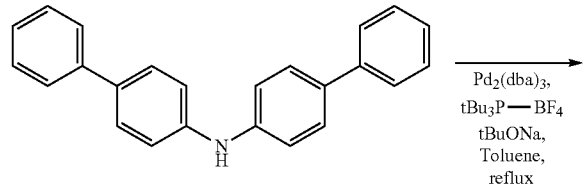

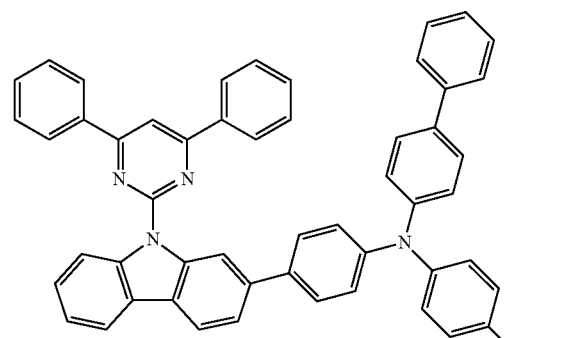

(H-6)

In an argon atmosphere, in a 300-mL-three-neck flask, intermediate (h) (6.6 g, 13.9 mmol), 4-chlorophenyloboronic acid (2.28 g, 14.6 mmol), tetrakistriphenylphosphine palladium (323 mg, 0.28 mmol), dimethoxyethane (DME, 30 mL), toluene (30 mL) and an aqueous 2M sodium carbonate solution (22 mL, 44 mmol) were added, and the resultant was allowed to react while heating under reflux for 8 hours. After cooling the reaction liquid to room temperature, an aqueous layer was removed by separation and an organic layer was dried with magnesium sulfate. Insoluble matters were removed by filtration and the organic solvent was removed under reduced pressure. The resulting residues were purified by silica gel column chromatography, whereby intermediate (i) (6.4 g, yield 90.6%) was obtained.

In an argon atmosphere, in a 100-mL-three-neck flask, intermediate (i) (2 g, 3.9 mmol), bisbiphenylamine (1.3 g, 3.9 mmol), tris(dibenzylideneacetone)dipalladium (70 mg, 0.078 mmol), tri-t-butylphosphonium tetrafluoroborate (0.09 g, 0.3 mmol), sodium t-butoxide (0.52 g, 5.5 mmol) and xylene anhydride (20 mL) were added in sequence, and the resultant was heated under reflux for 8 hours.

After cooling the reaction liquid to room temperature, insoluble matters were removed by filtration, and the organic solvent was distilled off under reduced pressure. The resulting residues were purified by silica gel column chromatography, whereby H-6 (2.1 g, yield 67.9%) was obtained.

For the obtained compound, a HPLC analysis and a FD-MS analysis were conducted. The results of these analyses are shown below.

HPLC: purity 99.6%

FD-MS: calcd for C58H40N4=792.96.

found m/z=793 (M+100).

Example 7

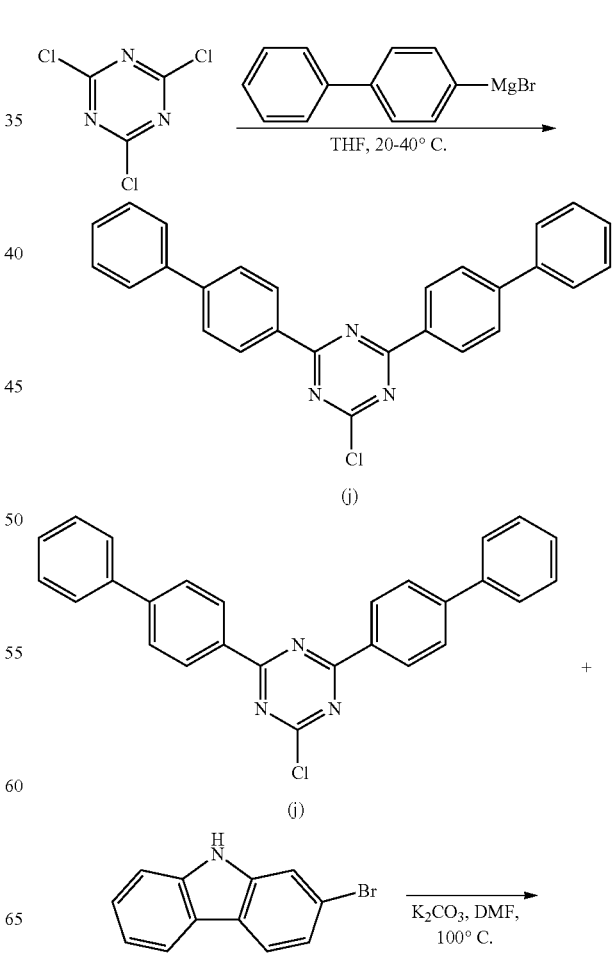

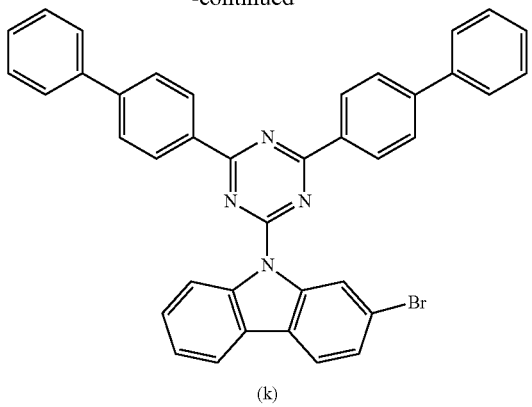

(k)

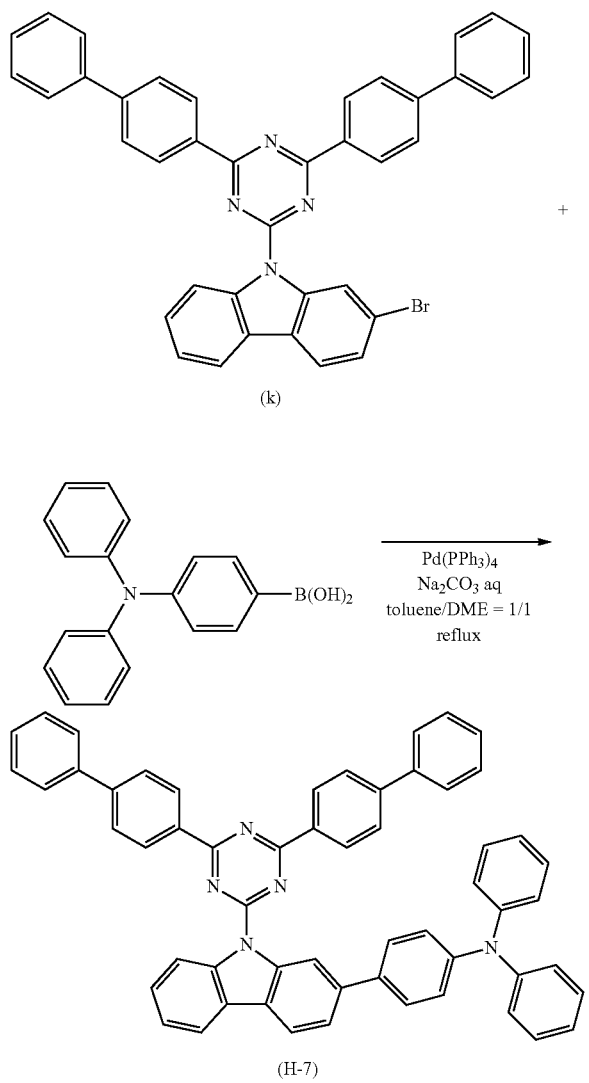

In an argon atmosphere, in a 500 mL-three-neck flask, 2,4,6-trichlorotriazine (47.2 g, 256 mmol) and dehydrated tetrahydrofuran (THF, 470 ml) were placed. While keeping the temperature of the reaction liquid at 20 to 40° C., 1M-biphenylmagnesium bromide (640 ml, 640 mmol) was added dropwise for 30 minutes, followed by stirring for 16 hours. Then, while keeping the temperature of the reaction liquid at 5 to 15° C., 150 ml of ion exchange water was added dropwise. A reaction product was extracted with ethyl acetate and an organic layer was dried with magnesium sulfate. Insoluble matters were removed by filtration, and the organic solvent was removed under reduced pressure. The resulting residues were purified by silica gel column chromatography, whereby intermediate (j) (32.7 g, yield 30%) was obtained.

In an argon atmosphere, in a 300 mL-three-neck flask, intermediate (j) (5.6 g, 21 mmol), 2-bromocarbazole (5.43 g, 22.1 mmol), potassium carbonate (3.48 g, 25.2 mmol) and dimethylformamide (DMF, 50 mL) were added. The resultant was heated under reflux at 100° C. for 8 hours. After cooling the reaction liquid to room temperature, insoluble matters were removed by filtration, and the organic solvent was removed under reduced pressure. The resulting residues were purified by silica gel column chromatography, intermediate (k) (10.9 g, yield 82.4%) was obtained.

In an argon atmosphere, in a 100 mL-three-neck flask, intermediate (k) (3.15 g, 5 mmol), diphenylaminophenylboronic acid (1.4 g, 5 mmol), tetrakistriphenylphosphine palladium (120 mg, 0.1 mmol), dimethoxyethane (DME, 10 mL), toluene (10 mL) and an aqueous 2M sodium carbonate solution (7.5 mL, 15 mmol) were added. The resultant was allowed to react for 8 hours while heating under reflux. After cooling the reaction liquid to room temperature, an aqueous layer was removed by separation, and an organic layer was dried with magnesium sulfate. Insoluble matters were removed by filtration, and the resulting residues were purified by silica gel column chromatography, whereby an intended product H-7 (2.1 g, yield 52.9%) was obtained.

For the obtained compound, a HPLC analysis and a FD-MS analysis were conducted. The results of these analyses are shown below.

HPLC: purity 99.5%
FD-MS: calcd for C57H39N5=793.95.
found m/z=794 (M+).

Example 8

Production of Organic EL Device

A glass substrate of 25 mm by 75 mm by 1.1 mm thick with an ITO transparent electrode (manufactured by GEOMATEC Co., Ltd.) was subjected to ultrasonic cleaning with isopropyl alcohol for 5-minutes, and then subjected to UV-ozone cleaning for 30 minutes.

The cleaned glass substrate with a transparent electrode was mounted in a substrate holder of a vacuum vapor deposition apparatus. First, the following electron-accepting compound (C–1) was deposited on the surface where transparent electrode lines were formed so as to cover the transparent electrode, thereby to form a 5 nm-thick C-1 film. Subsequently, on this C-1 film, the following aromatic amine derivative (X1) was deposited as the first hole-transporting material to obtain a 50 nm-thick first hole-transporting layer. Subsequent to the formation of the first hole-transporting layer, as a second-transporting material, the following aromatic amine derivative (X2) was deposited to form a 10 nm-thick second hole-transporting layer.

Further, on this second hole-transporting layer, the aromatic amine derivative (H-1) obtained in Example 1 was deposited, whereby a 45 nm-thick emitting layer was formed. Simultaneously, as a phosphorescent emitting material, the following compound (D3) was co-deposited. The concentration of the compound D3 was 8.0 mass %. This co-deposition layer functions as the emitting layer.

Subsequent to the formation of the emitting layer, the following compound (ET2) was formed into a 30 nm-thick film. This ET1 film functions as the electron-transporting layer.

Subsequently, LiF was formed into a 1 nm-thick film as an electron-injecting electrode (cathode) at a film-formation speed of 0.1 Å/min. On this LiF film, metal Al was deposited to form a metal cathode in a thickness of 80 nm, whereby an organic EL device was fabricated.

The luminous efficiency of the obtained organic EL device was measured at an initial luminance of 2000 cd/m², at room temperature and by DC constant current driving. The results are shown in Table 1.

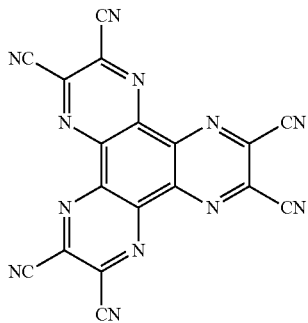

C-1

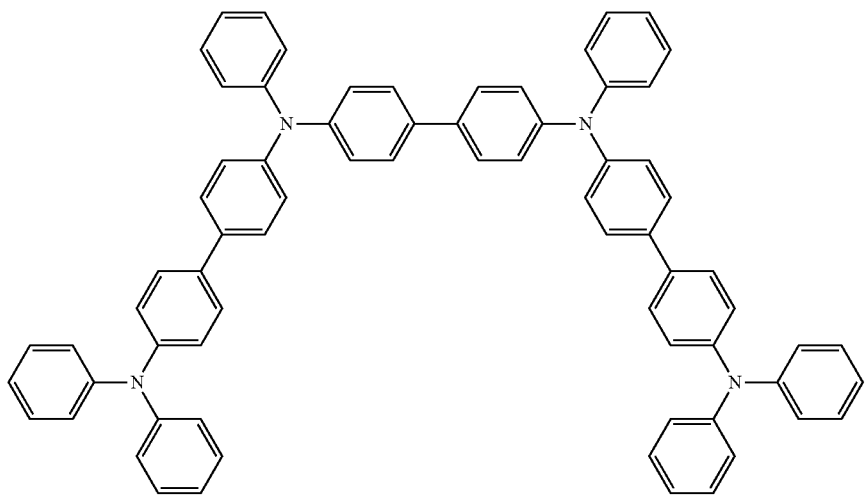

X1

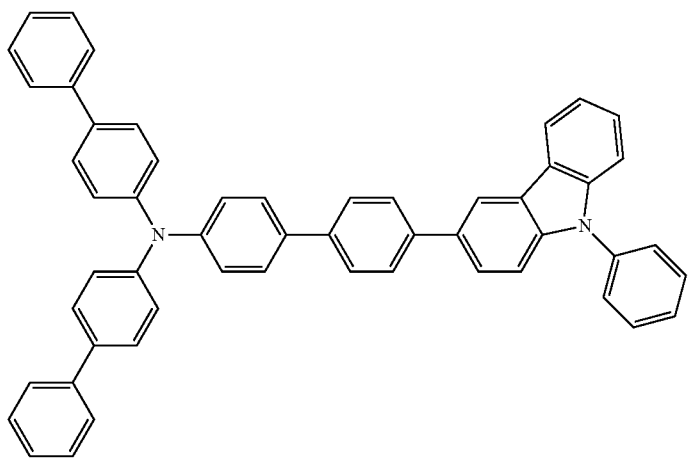

X2

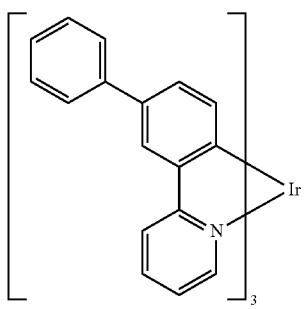

D3

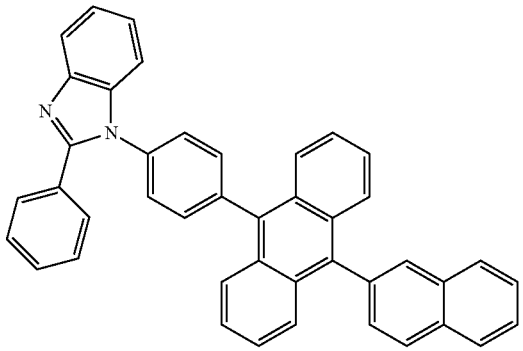

ET2

Examples 9 to 12 and Comparative Examples 1 to 3

Organic EL devices were fabricated and evaluated in the same manner as in Example 8, except that, as the material for the emitting layer, compounds shown in Table 1 were used instead of H-1. The results are shown in Table 1.

The compounds used in Comparative Examples 1 to 3 are as follows.

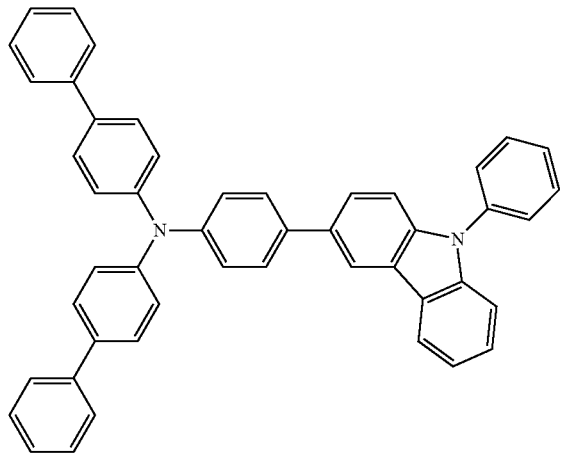

Exp1

-continued

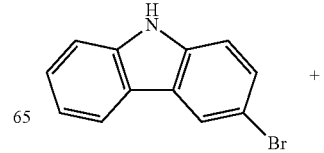

Exp3

TABLE 1

|  |  | Material for emitting layer | Driving voltage (V) | Luminous efficiency (cd/A) |
|---|---|---|---|---|
| Examples | 8 | H-1 | 2.9 | 55 |
|  | 9 | H-2 | 2.9 | 57 |
|  | 10 | H-3 | 2.9 | 55 |
|  | 11 | H-4 | 2.9 | 50 |
|  | 12 | H-6 | 2.9 | 52 |
| Comp. Ex. | 1 | Exp1 | 2.9 | 5 |
|  | 2 | Exp2 | 3.1 | 35 |
|  | 3 | Exp3 | 3.1 | 16 |

From Table 1, it can be understood that the organic EL devices using the aromatic amine derivatives of the invention in the emitting layer had a higher luminous efficiency as compared with the devices of Comparative Examples. In Comparative Example 1, emission from the electron-transporting material was observed. The reason therefor is assumed to be as follows. The hole-transporting properties of the comparative compound was large, and as a result, holes were injected from the emitting layer to the electron-transporting layer.

Example 13

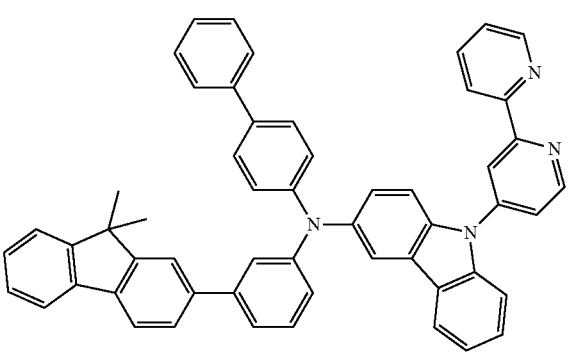

Exp2

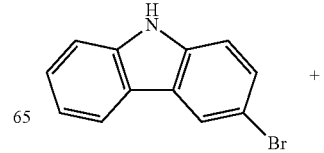

+

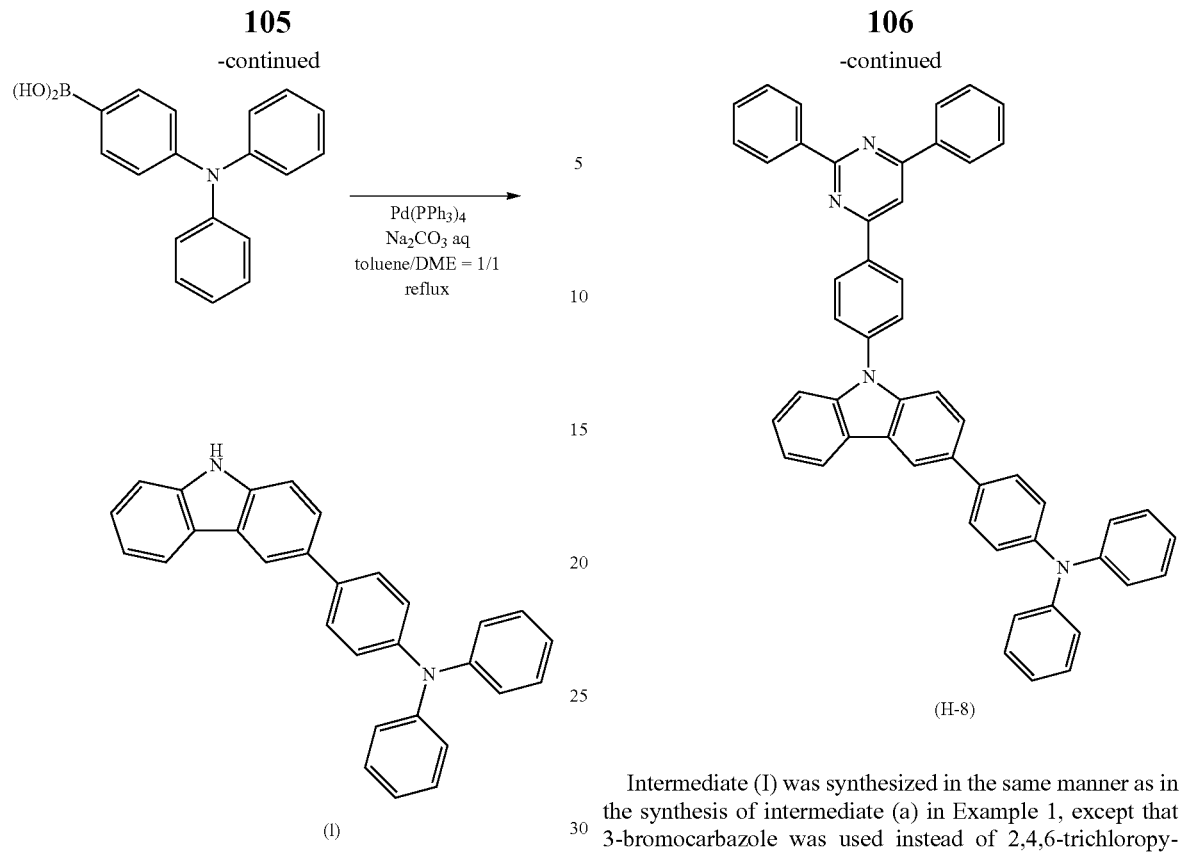

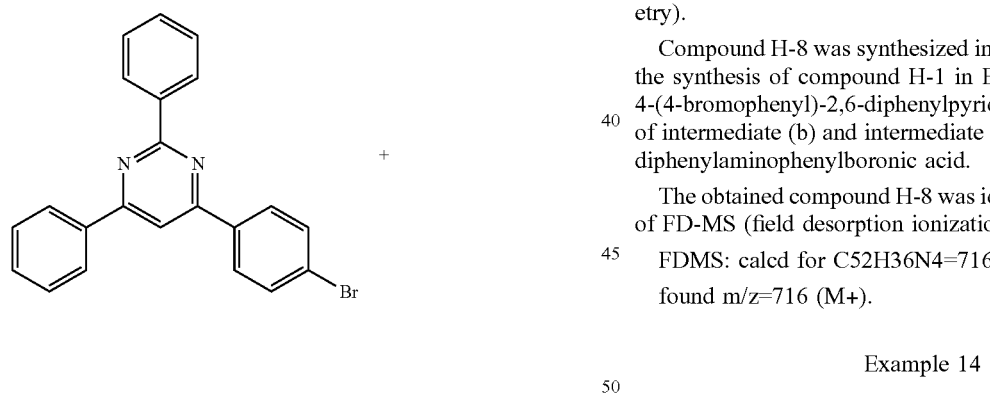

Intermediate (I) was synthesized in the same manner as in the synthesis of intermediate (a) in Example 1, except that 3-bromocarbazole was used instead of 2,4,6-trichloropyrimidine and diphenylaminophenylboronic acid was used instead of phenylboronic acid.

The obtained intermediate (I) was identified by an analysis of FD-MS (field desorption ionization mass spectrometry).

Compound H-8 was synthesized in the same manner as in the synthesis of compound H-1 in Example 1, except that 4-(4-bromophenyl)-2,6-diphenylpyridine was used instead of intermediate (b) and intermediate (I) was used instead of diphenylaminophenylboronic acid.

The obtained compound H-8 was identified by an analysis of FD-MS (field desorption ionization mass spectrometry).

FDMS: calcd for C52H36N4=716.

found m/z=716 (M+).

Example 14

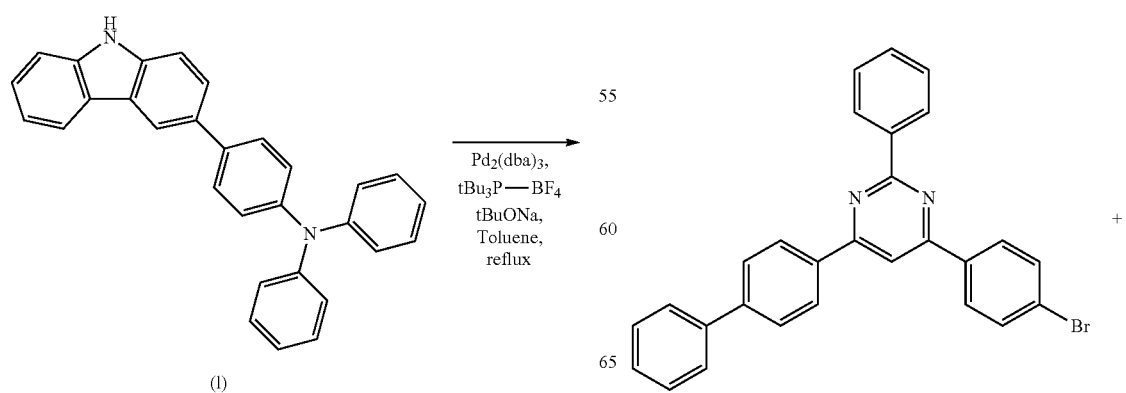

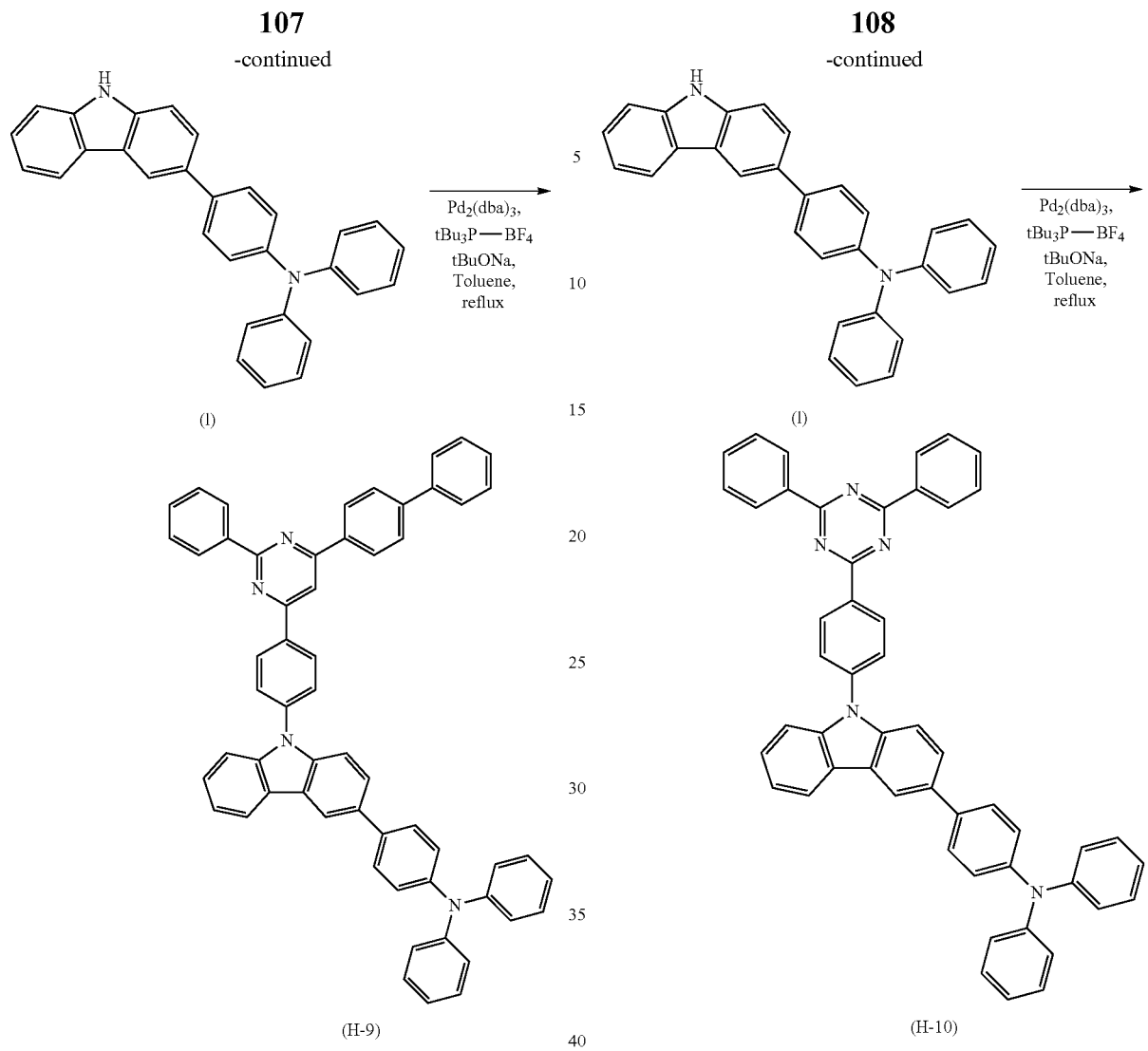

(H-9)

(H-10)

Compound H-9 was synthesized in the same manner as in the synthesis of compound H-1 in Example 1, except that 6-biphenyl-4-(4-bromophenyl)-2-phenylpyrimidine was used instead of intermediate (b) and intermediate (I) was used instead of diphenylaminophenylboronic acid.

The obtained compound H-9 was identified by an analysis of FD-MS (field desorption ionization mass spectrometry). The results are shown below.

FDMS: calcd for $C_{58}H_{40}N_4$=792.
found m/z=792 (M+).

Example 15

Compound H-10 was synthesized in the same manner as in the synthesis of compound H-1 in Example 1, except that 2-(4-bromophenyl)-4,6-diphenyltriazine was used instead of intermediate (b) and intermediate (I) was used instead of diphenylaminophenylboronic acid.

The obtained compound H-10 was identified by an analysis of FD-MS (field desorption ionization mass spectrometry). The results are shown below.

FDMS: calcd for $C_{51}H_{35}N_5$=717.
found m/z=717 (M+).

Example 16

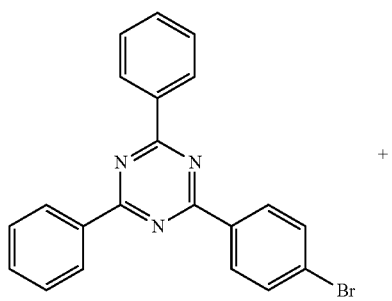

+

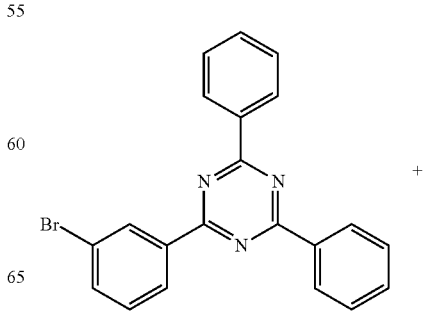

+

-continued

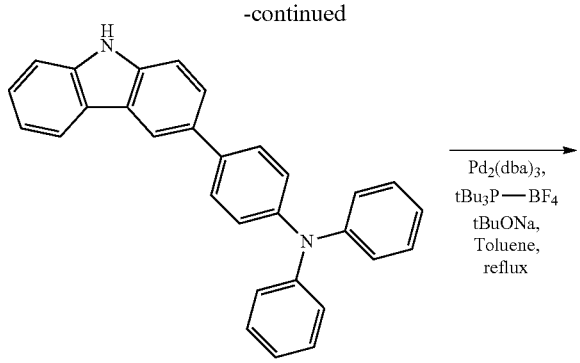

(I)

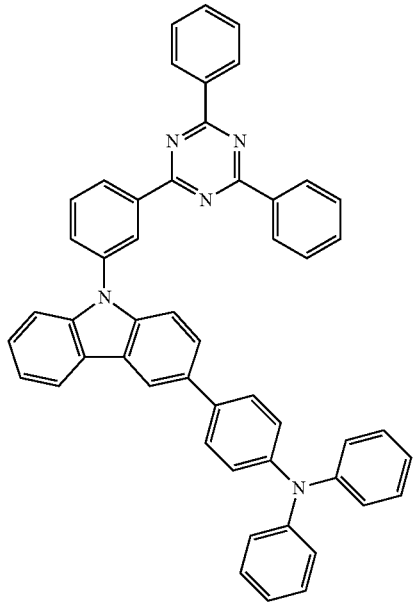

(H-11)

Compound H-11 was synthesized in the same manner as in the synthesis of compound H-1 in Example 1, except that 2-(3-bromophenyl)-4,6-diphenyltriazine was used instead of intermediate (b) and intermediate (I) was used instead of diphenylaminophenylboronic acid.

The obtained compound H-11 was identified by an analysis of FD-MS (field desorption ionization mass spectrometry). The results are shown below.

FDMS: calcd for C51H35N5=717.
found m/z=717 (M+).

Example 17

Production of Organic EL Device

A glass substrate of 25 mm by 75 mm by 1.1 mm thick with an ITO transparent electrode (manufactured by GEO-MATEC Co., Ltd.) was subjected to ultrasonic cleaning with isopropyl alcohol for 5 minutes, and then subjected to UV-ozone cleaning for 30 minutes. The thickness of the ITO transparent electrode was 130 nm.

The cleaned glass substrate with a transparent electrode was mounted in a substrate holder of a vacuum vapor deposition apparatus. First, the following compound (HI-1) was deposited on the surface where transparent electrode lines were formed so as to cover the transparent electrode, thereby to form a 5 nm-thick HI-1 film that serves as a hole-injecting layer.

Subsequently, on this hole-injecting layer, as a first hole-transporting material, the following compound HT-1 was deposited to form an 80 nm-HT-1 film, thereby to form a first hole-transporting layer.

Subsequently, on this first hole-transporting layer, the following compound HT-2 was deposited to form a 15 nm-thick HT film, whereby a second hole-transporting layer was formed.

Subsequently, on this second hole-transporting layer, compound BH-1 (host material) and BD-1 (dopant material) were co-deposited, thereby forming a 25 nm-thick co-deposition film. The concentration of the compound BD-1 was 5.0 mass %. This co-deposition film functions as the emitting layer.

Subsequently, on this emitting layer, compound H-3 that had been prepared was deposited to form a 20 nm-thick H-3 film, thereby forming a first electron-transporting layer.

Subsequently, on the first electron-transporting layer, the following compound ET-2 was deposited to form a 5 nm-thick ET-2 film, thereby forming a second electron-transporting layer.

Subsequently, on this second electron-transporting layer, LiF was formed into a 1 nm-thick LiF film as an electron-injecting electrode (cathode) at a film-formation speed of 0.01 nm/sec. On this LiF film, metal Al was deposited to form a metal Al film in a thickness of 80 nm, thereby to form a metal Al cathode, whereby an organic EL device was fabricated.

The materials used for the fabrication of the organic EL devices are shown below.

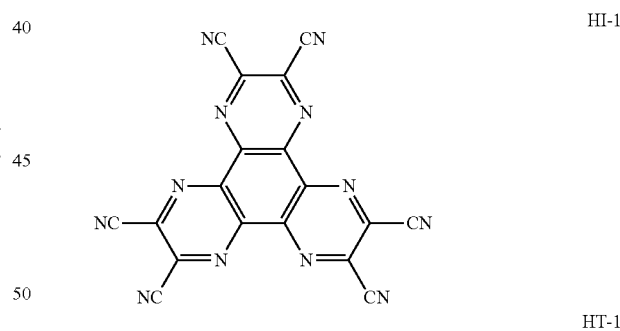

HI-1

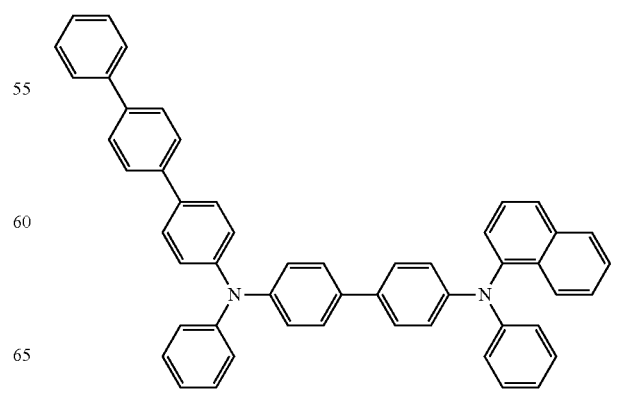

HT-1

-continued

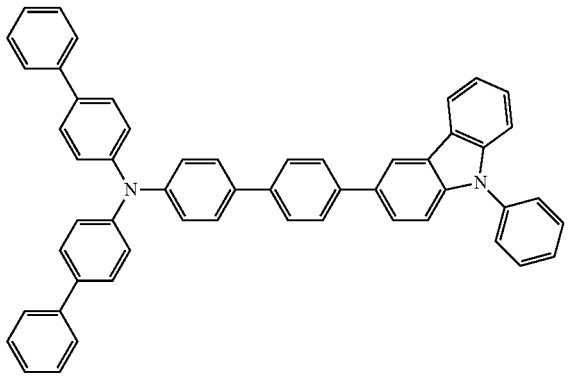

HT-2

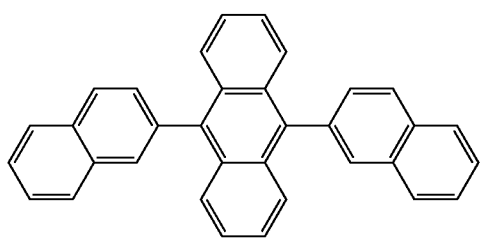

BH-1

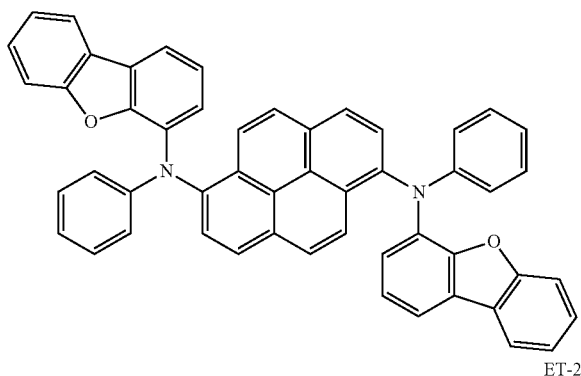

ET-2

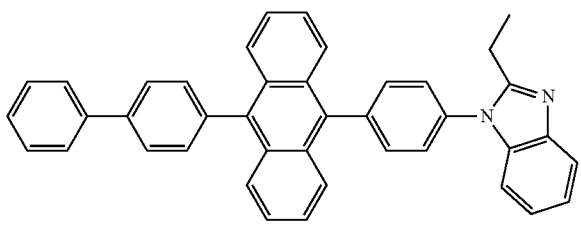

(Evaluation of Organic EL Device)

The luminous efficiency of the obtained organic EL device was measured at room temperature and by DC constant current driving (current density: 10 mA/cm$^2$). Further, a LT80 luminance life by DC constant current driving (current density: 50 mA/cm$^2$) (time that elapsed until the initial luminance was reduced to 80% at constant current driving) was measured. The results are shown in Table 2.

Example 18 and Comparative Example 4

Organic EL devices were fabricated and evaluated in the same manner as in Example 17, except that compounds shown in Table 2 were used instead of compound H-3. The results are shown in Table 2.

Compound H-11 in Table 2 was the compound prepared in Example 16, and compound Exp4 was the compound shown below.

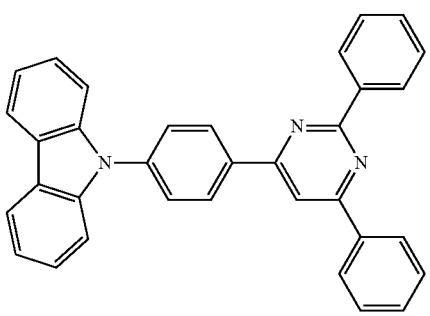

Exp4

TABLE 2

| | First electron-transporting layer | Luminous efficiency (cd/A) | LT80% (h) |
|---|---|---|---|
| Example 17 | H-3 | 7.4 | 210 |
| Example 18 | H-11 | 7.0 | 180 |
| Comp. Ex. 4 | Exp4 | 4.5 | 60 |

INDUSTRIAL APPLICABILITY

The organic EL device of the invention can be utilized for a planar emitting body such as a flat panel display of a wall-hanging television, a copier, a printer, a back light of a liquid crystal display, or a light source in instruments or the like, a sign board, a signal light or the like.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The Japanese application specification claiming priority under the Paris Convention are incorporated herein by reference in its entirety.

The invention claimed is:

1. An aromatic amine derivative represented by the following formula (1):

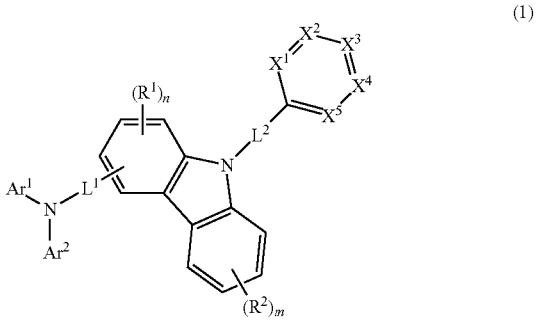

(1)

wherein in the formula (1),

Ar$^1$ and Ar$^2$ are independently a substituted or unsubstituted aryl group including 6 to 60 ring carbon atoms;

L$^1$ is a substituted or unsubstituted arylene group including 6 to 60 ring carbon atoms;

L$^2$ is a single bond or a substituted or unsubstituted arylene group including 6 to 60 ring carbon atoms;

R$^1$ and R$^2$ are independently a substituted or unsubstituted aryl group including 6 to 60 ring carbon atoms, a substituted or unsubstituted alkyl group including 1 to 50 carbon atoms, a substituted or unsubstituted heteroaryl group including 5 to 30 ring atoms, a substituted or unsubstituted alkoxy group including 1 to 50 carbon atoms, a substituted or unsubstituted aryloxy group including 6 to 60 ring carbon atoms, a halogen atom or a cyano group;

n is an integer of 0 to 3;

m is an integer of 0 to 4;

when plural R$^1$s are present, the plural R$^1$s may be the same or different;

when plural R$^2$s are present, the plural R$^2$s may be the same or different;

X$^1$ to X$^5$ are independently a nitrogen atom or CR$^3$; provided that at least two of X$^1$ to X$^5$ are a nitrogen atom;

R$^3$ is a hydrogen atom, a substituted or unsubstituted aryl group including 6 to 60 ring carbon atoms, a substituted or unsubstituted alkyl group including 1 to 50 carbon atoms, a substituted or unsubstituted alkoxy group including 1 to 50 carbon atoms, a substituted or unsubstituted aryloxy group including 6 to 60 ring carbon atoms, a halogen atom or a cyano group; and when plural R$^3$s are present, the plural R$^3$s may be the same or different.

2. The aromatic amine derivative according to claim 1, wherein two of X$^1$ to X$^5$ are a nitrogen atom.

3. The aromatic amine derivative according to claim 1, wherein L$^2$ is a single bond.

4. The aromatic amine derivative according to claim 1, wherein three of X$^1$ to X$^5$ are a nitrogen atom.

5. The aromatic amine derivative according to claim 1, wherein Ar$^1$ and Ar$^2$ do not comprise a fluorene structure.

6. The aromatic amine derivative according to claim 1, that is represented by the following formula (1-1) or (1-2):

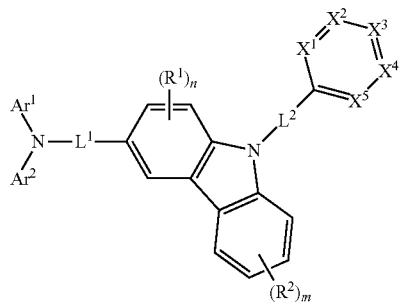

(1-1)

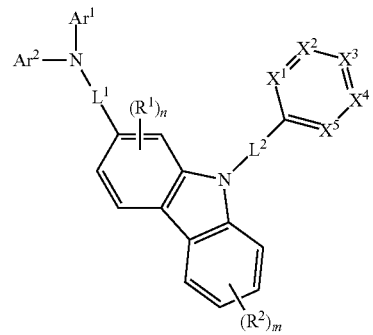

(1-2)

wherein in the formulas (1-1) and (1-2), Ar$^1$, Ar$^2$, L$^1$, L$^2$, R$^1$, R$^2$, n, m, X$^1$ to X$^5$ and R$^3$ are as defined in the formula (1).

7. A material for an organic electroluminescent device comprising the aromatic amine derivative according to claim 1.

8. An organic electroluminescence device comprising:
an anode;
a cathode; and
one or more organic layers including an emitting layer between the anode and the cathode,
wherein at least one of the organic layers comprises the aromatic amine derivative according to claim 1.

9. The organic electroluminescence device according to claim 8, wherein the aromatic amine derivative is contained in the emitting layer.

10. The organic electroluminescence device according to claim 8, wherein the emitting layer comprises a phosphorescent emitting material.

11. The aromatic amine derivative according to claim 1, wherein n is 0 and m is 0.

12. The aromatic amine derivative according to claim 1, wherein L$^1$ is a substituted or unsubstituted arylene group including 6 to 20 ring carbon atoms.

13. The aromatic amine derivative according to claim 12, wherein L$^1$ is selected from the group consisting of a substituted or unsubstituted phenylene group, a substituted or unsubstituted biphenylene group and a substituted or unsubstituted fluorenylene group.

14. The aromatic amine derivative according to claim 1, wherein L$^1$ is selected from:

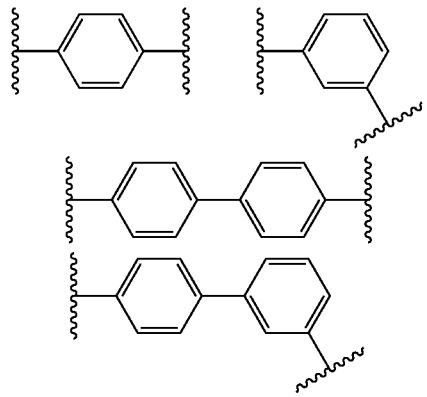

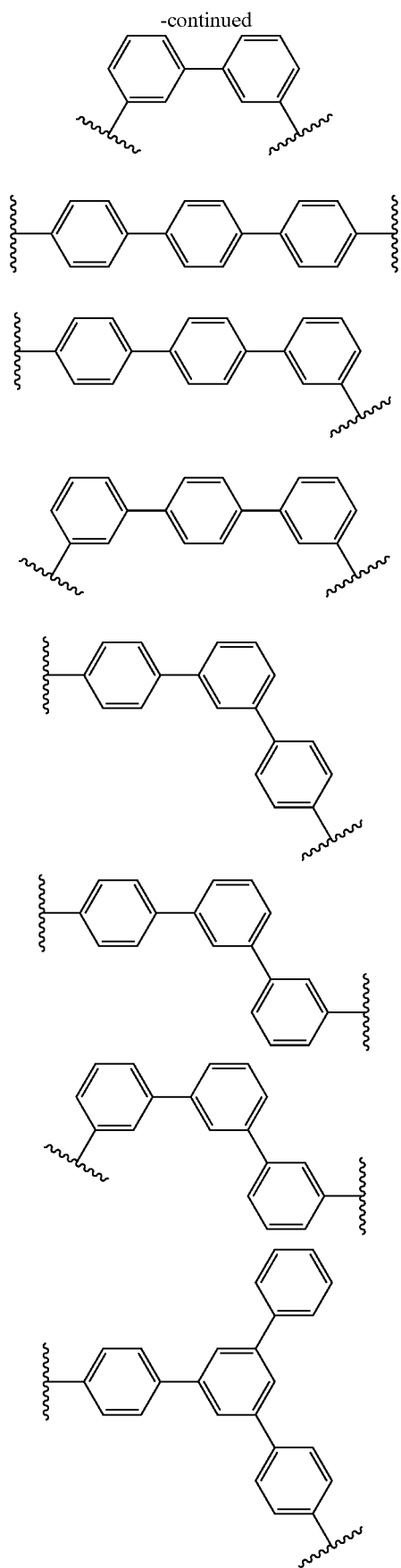
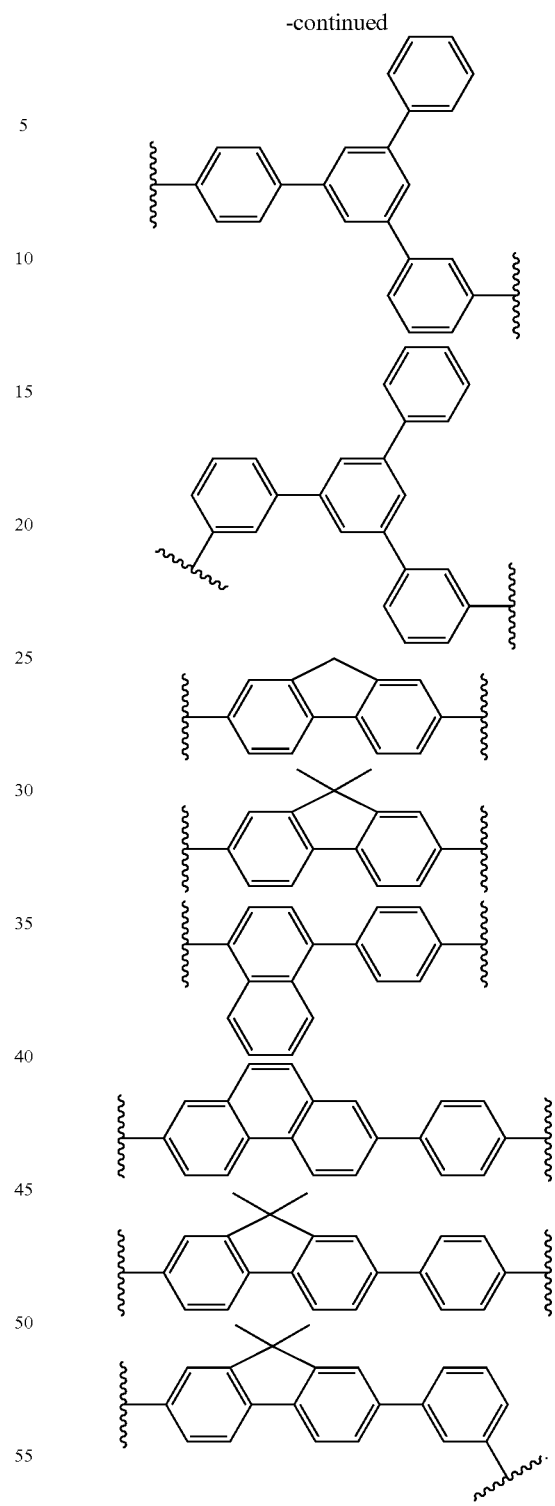

15. The aromatic amine derivative according to claim 1, wherein Ar¹ and Ar² are a substituted or unsubstituted aryl group including 6 to 60 ring carbon atoms.

16. The aromatic amine derivative according to claim 1, wherein R¹ and R² are independently a substituted or unsubstituted aryl group including 6 to 60 ring carbon atoms.

17. The aromatic amine derivative according to claim 1, wherein R¹ and R² are selected from the group consisting of a substituted or unsubstituted phenyl group, a substituted or unsubstituted biphenyl group, a substituted or unsubstituted napthyl group, and a substituted or unsubstituted terphenyl group.

18. The aromatic amine derivative according to claim 1, wherein R³ is a substituted or unsubstituted aryl group including 6 to 60 ring carbon atoms.

19. The aromatic amine derivative according to claim 1, wherein at least one combination of X¹ and X³; X¹ and X⁵; or X¹, X³ and X⁵ are a nitrogen atom.

20. The aromatic amine derivative according to claim 1, wherein L¹ is a substituted or unsubstituted arylene group including 6 to 20 ring carbon atoms; Ar¹ and Ar² are a substituted or unsubstituted aryl group including 6 to 60 ring carbon atoms; R¹ and R² are independently a substituted or unsubstituted aryl group including 6 to 60 ring carbon atoms; and R³ is a substituted or unsubstituted aryl group including 6 to 60 ring carbon atoms.

21. The aromatic amine derivative according to claim 1, wherein n is 0 and m is 0; L¹ is selected from:

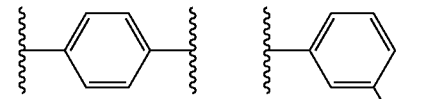

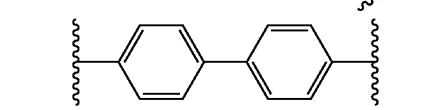

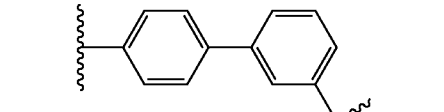

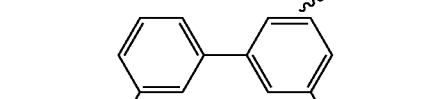

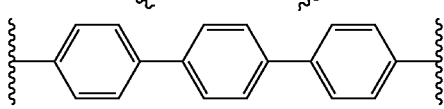

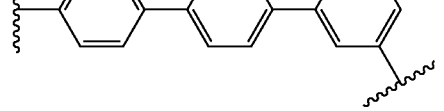

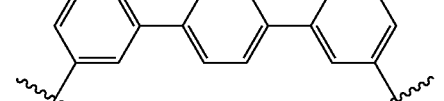

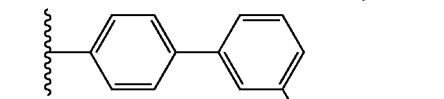

-continued

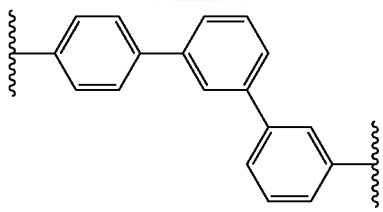

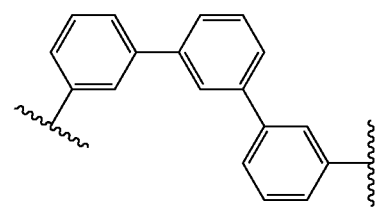

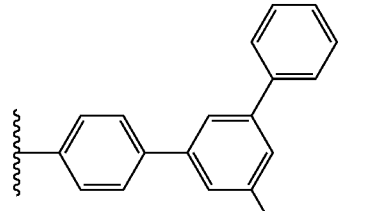

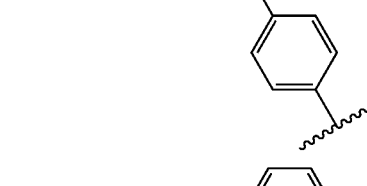

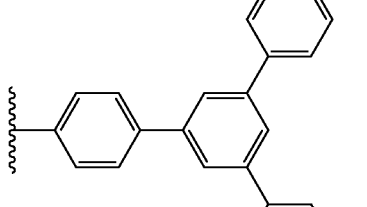

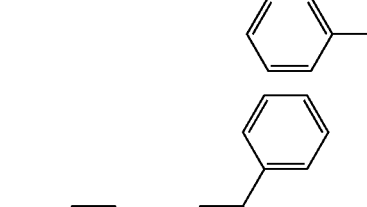

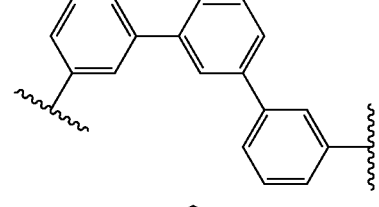

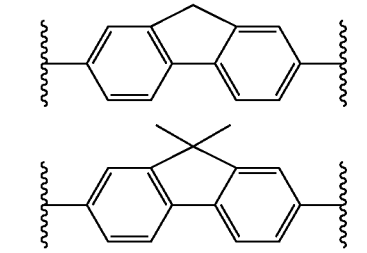

-continued
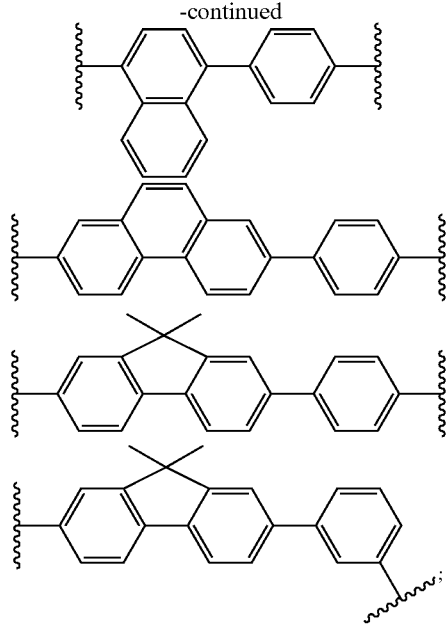
Ar$^1$ and Ar$^2$ are a substituted or unsubstituted aryl group including 6 to 60 ring carbon atoms;
and R$^3$ is a substituted or unsubstituted aryl group including 6 to 60 ring carbon atoms.
* * * * *